(12) United States Patent
Wood et al.

(10) Patent No.: US 11,993,788 B2
(45) Date of Patent: May 28, 2024

(54) COMPOSITION COMPRISING B REGULATORY CELLS

(71) Applicant: Oxford University Innovation Limited, Oxford (GB)

(72) Inventors: Kathryn J. Wood, Oxford (GB); Sushma Shankar, Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 879 days.

(21) Appl. No.: 16/610,534

(22) PCT Filed: May 3, 2018

(86) PCT No.: PCT/GB2018/051192
§ 371 (c)(1),
(2) Date: Nov. 4, 2019

(87) PCT Pub. No.: WO2018/203072
PCT Pub. Date: Nov. 8, 2018

(65) Prior Publication Data
US 2020/0087624 A1 Mar. 19, 2020

(30) Foreign Application Priority Data
May 5, 2017 (GB) ..................................... 1707238

(51) Int. Cl.
*C12N 5/0781* (2010.01)
*A61K 35/17* (2015.01)
*C07K 16/28* (2006.01)
*G01N 33/50* (2006.01)

(52) U.S. Cl.
CPC ............ *C12N 5/0635* (2013.01); *A61K 35/17* (2013.01); *C07K 16/2803* (2013.01); *C07K 16/2866* (2013.01); *C07K 16/2875* (2013.01); *C07K 16/2878* (2013.01); *C07K 16/2887* (2013.01); *G01N 33/5091* (2013.01); *C07K 2317/31* (2013.01); *C12N 2501/2302* (2013.01); *C12N 2501/2304* (2013.01); *C12N 2501/231* (2013.01); *C12N 2501/2321* (2013.01); *C12N 2501/52* (2013.01); *C12N 2501/599* (2013.01); *G01N 2800/24* (2013.01); *G01N 2800/26* (2013.01); *G01N 2800/50* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 5,817,516 | A | 10/1998 | Kehry et al. |
| 8,444,973 | B2 | 5/2013 | Tedder et al. |
| 9,228,171 | B2 | 1/2016 | Arya et al. |
| 9,260,530 | B2 | 2/2016 | Tedder et al. |
| 2011/0135666 | A1 | 1/2011 | Aso et al. |
| 2012/0308563 | A1 | 2/2012 | Bevier |
| 2012/0052059 | A1 | 3/2012 | Rothstein et al. |
| 2013/0136754 | A1 | 1/2013 | Lacapra et al. |
| 2013/0309229 | A1* | 11/2013 | Yang ........................ A61P 37/02 424/173.1 |
| 2014/0065118 | A1 | 3/2014 | Tedder et al. |
| 2015/0110737 | A1 | 1/2015 | Lei et al. |
| 2016/0152951 | A1 | 1/2016 | Radhakrishnan et al. |
| 2019/0352607 | A1* | 11/2019 | Suga .................... C12N 5/0635 |
| 2021/0122727 | A1* | 4/2021 | Schafer ................ C07D 401/04 |

FOREIGN PATENT DOCUMENTS

| CN | 106220740 A | 12/2016 |
| WO | 2010/034103 A1 | 4/2010 |
| WO | 2016/100932 A1 | 6/2016 |

OTHER PUBLICATIONS

Liu et al ( United European Gastroenter. J, 2015, v.3 N.5 PA12, Abstract OP034.*
Mohanram et al ( J of Immunol, 2016, v.197, pp. 2316-2324.*
Cai et al (Chinese Medicine, 2016, v.11, pp. 1-13.*
International Search Report & Written Opinion for WO2018/203072 (PCT/GB2018/051192), dated Oct. 8, 2018, pp. 1-17.
Shankar, S: "Ex vivo expansion of human IL-10+ B cells with regulatory function (PHD thesis).", EThos E-theses online service Bodleian Libraries—University of Oxford., Dec. 31, 2016 (Dec. 31, 2016).
Aharon Kessel et al: "Human CD19+CD25high B regulatory cells suppress proliferation of CD4+ T cells and enhance Foxp3 and CTLA-4 expression in T-regulatory cells", Autoimmunity Reviews, vol. 11, No. 9, Jul. 1, 2012 (Jul. 1, 2012), pp. 670-677.
Claudia Mauri et al: "The expanding family of regulatory B cells", International Immunology, vol. 27, No. 10, Jun. 12, 2015 (Jun. 12, 2015) , pp. 479-486.
Shankar et al: Ex vivo expanded human CD19+CD25+CD71+TIM-1+ B regulatory cells can prolong allograft survival in a humanized mouse model of Skin Transplantation and Are Dependent on TIM-1-Mediated Regulation of STAT3 Signaling, 2018 American Transplant Congress, Jun. 2-6, 2018 , Seattle, WA American Journal of Transplantation, Jun. 5, 2018 (Jun. 5, 2018).
Anushruti Sarvaria et al: "B cell regulation in cancer and anti-tumor immunity", Cellular & Molecular Immunology, vol. 14, No. 8, Jun. 19, 2017 (Jun. 19, 2017), pp. 662-674.
Octavio Aravena et al: "TIM-I defines a human regulatory B cell population that is altered in frequency and function in systemic sclerosis patients", Arthritis Research & Therapy, vol. 19, No. 1. Jan. 19, 2017 (Jan. 19, 2017).

(Continued)

*Primary Examiner* — Michail A Belyavskyi
(74) *Attorney, Agent, or Firm* — Thomas|Horstemeyer, LLP

(57) ABSTRACT

The present invention relates to an expanded population of human Breg cells having the phenotype CD19+CD73-CD71+CD25+TIM-1+ and methods for producing the cell population of the invention. The invention also relates to pharmaceutical compositions comprising the cell populations of the invention and their use in the treatment of immune-mediated disorders.

20 Claims, 42 Drawing Sheets

(56) References Cited

OTHER PUBLICATIONS

International Preliminary Report on Patentability for WO2018/203072 (PCT/GB2018/051192), dated Nov. 5, 2019, pp. 1-11.
Newell, K.A., et al., J Clin Invest, 2010. 120(6): p. 1836-47.
Sagoo, P., et al., J Clin Invest, 2010. 120(6): p. 1848-61.
Blair, P.A., et al., Immunity, 2010. 32(1): p. 129-40.
Iwata, Y., et al., Blood, 2011. 117(2): p. 530-41.
Rebollo-Mesa, I., et al., Am J Transplant, 2016.
Carter, N.A., et al., J Immunol, 2011. 186(10): p. 5569-79.
Watanabe, R., et al., J Immunol, 2010. 184(9): p. 4801-9.
DiLillo, D.J., et al., J Immunol, 2011. 186(4): p. 2643-54.
Lee, K.M., et al., Eur J Immunol, 2014. 44(6): p. 1728-36.
Rosser, E.C., et al., Nat Med, 2014. 20(11): p. 1334-9.
Tang, A., et al., Int J Cancer, 2016.
Tadmor, T., et al., Cancer Immunol Immunother, 2011. 60(5): p. 609-19.
Liu, J., et al., PLoS One, 2014. 9(2): p. e89236.
Mohanram, V., et al., J Immunol, 2016. 197(6): p. 2316-24.
Yoshizaki, A., et al., Nature, 2012. 491(7423): p. 264-8.
Mauri, C., et al., J Exp Med, 2003. 197(4): p. 489-501.
Mauri, C., L.T. Mars, and M. Londei, Nat Med, 2000. 6(6): p. 673-9.
Rosser, E.C. and C. Mauri, Immunity, 2015. 42(4): p. 607-12.
Van de Veen, W., et al., J Allergy Clin Immunol, 2013. 131(4): p. 1204-12.
Lemoine, S., et al., J Autoimmun, 2011. 36(3-4): p. 228-38.
Ding, Q., et al., J Clin Invest, 2011. 121(9): p. 3645-56.
Yeung, M.Y., et al., Am J Transplant, 2015. 15(4): p. 942-53.
Xiao, S., et al., Proc Natl Acad Sci U S A, 2012. 109(30): p. 12105-10.
Xiao, S., et al., J Immunol, 2015. 194(4): p. 1602-8.
Blair, P.A., et al., J Immunol, 2009. 182(6): p. 3492-502.
Wang, R.X., et al., Nat Med, 2014. 20(6): p. 633-41.
Shen, P., et al., Nature, 2014. 507(7492): p. 366-70.
De Masson, A., et al., Blood, 2015. 125(11): p. 1830-9.
Silva, H.M., et al., Mol Med, 2012. 18: p. 733-43.
Yang, C., et al., PLoS One, 2013. 8(5): p. e64159.
Carter, N.A., E.C. Rosser, and C. Mauri, Arthritis Res Ther, 2012. 14(1): p. R32.
Sicard, A., et al., (2016) Nano Letters 16(1):297-308.
Koenig et al., 2016, Transplantation 100(7):1460-1464.
Tedder, T. F., 2015, J Immunol. 194:1395-1401.
15th Beaune Seminar in Transplant Research, Programme, May 21-22, 2015.
Stolp, J. et al., Jun. 2014 "Uncovering the Role of Immune Regulatory B Cells in a Mouse Model of Transplant Tolerance." American Journal Of Transplantation 14:267-267; Supplement:3, Meeting Abstract: D2674.
Kalampokis et al., 2013, Arthritis Research & Therapy 15(Suppl 1):S1.
UK Search Report for GB 1707238.0, dated Feb. 12, 2018, pp. 1-6.
S. Shankar et al., "Ex vivo-expanded human CD19+TIM-1+ regulatory B cells suppress immune responses in vivo and are dependent upon the TIM-1/STAT3 axis", Nature Communications | (2022) 13:3121 | https://doi.org/10.1038/s41467-022-30613-z | www.nature.com/naturecommunications, pp. 1-19.

* cited by examiner

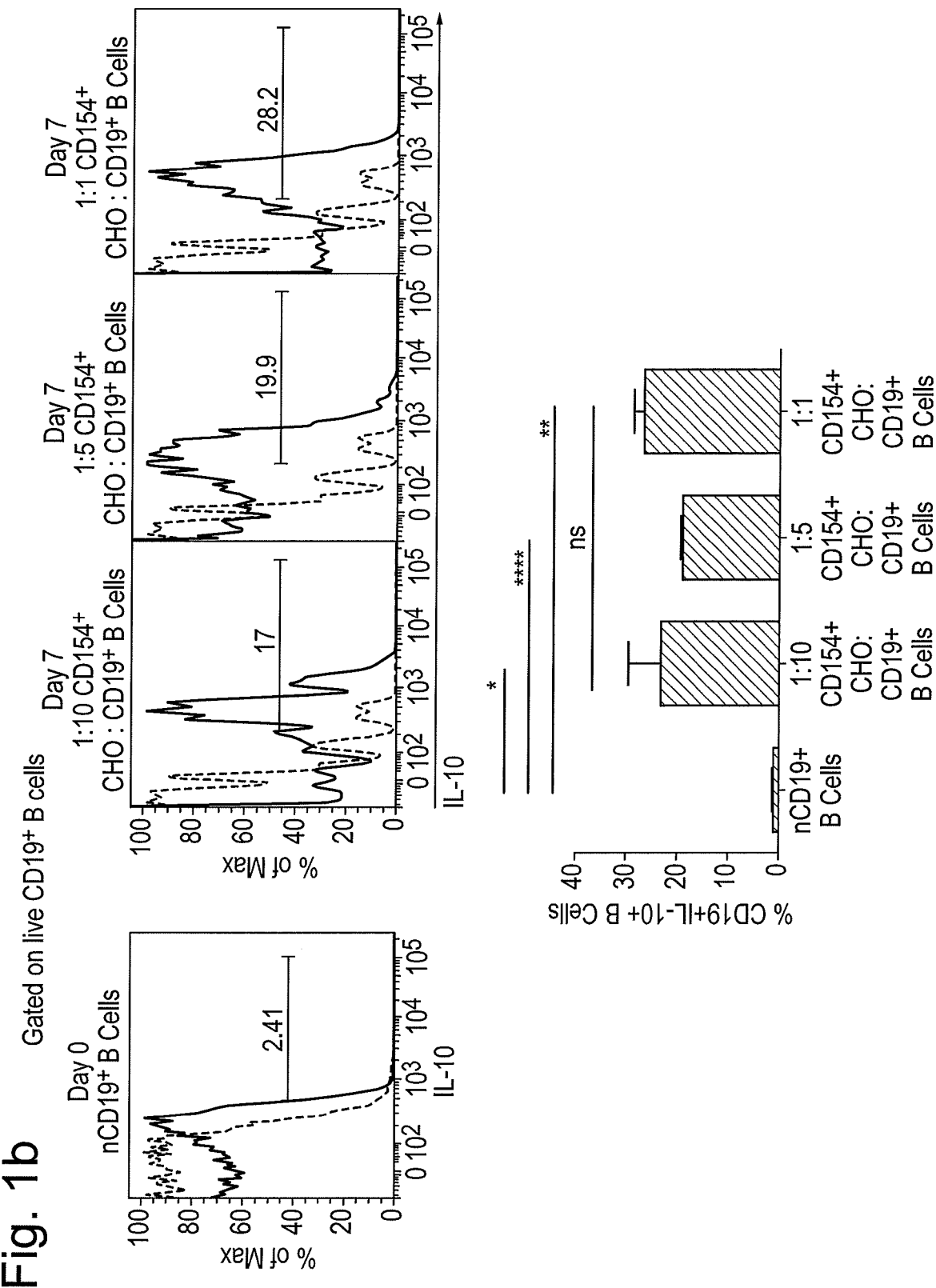

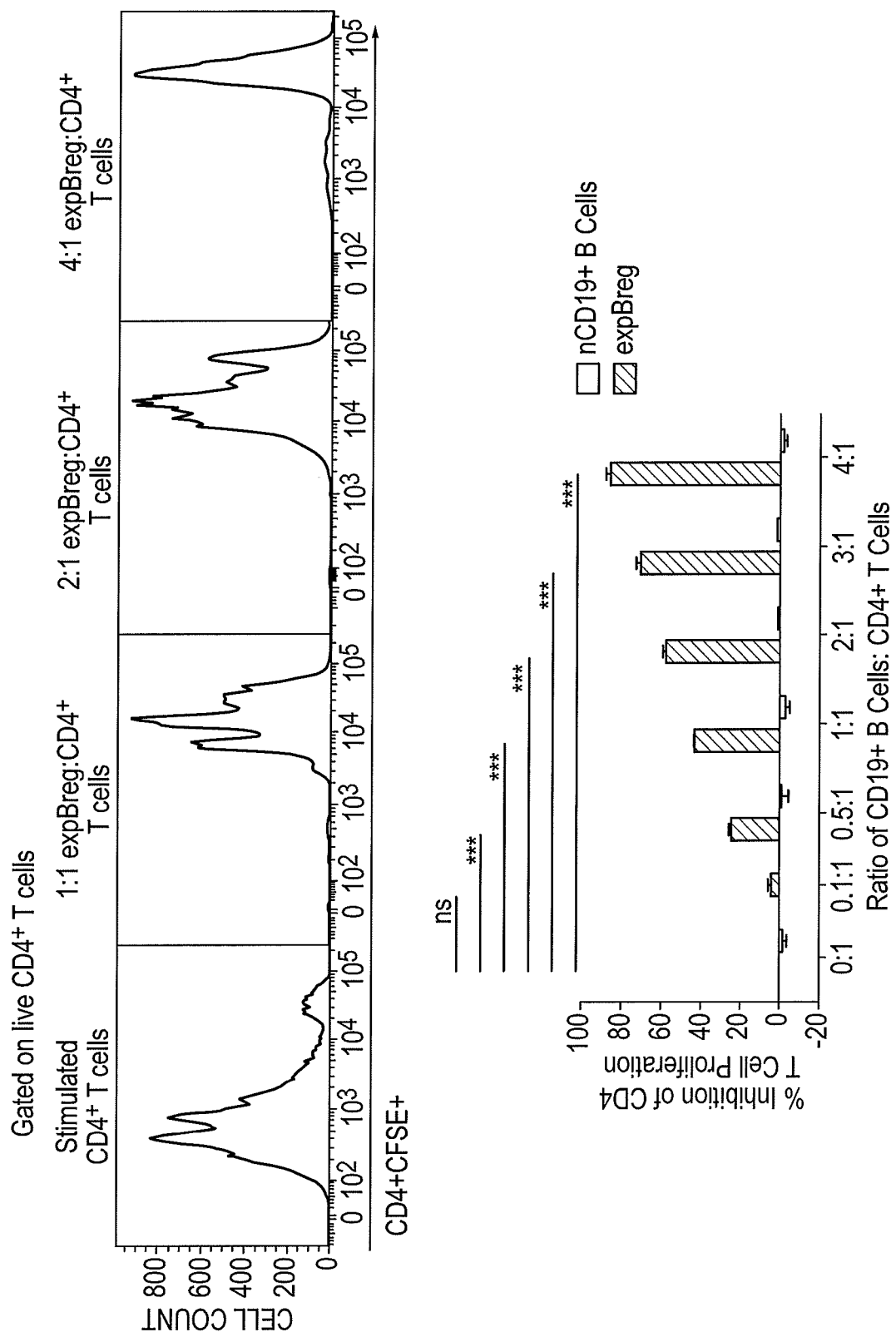

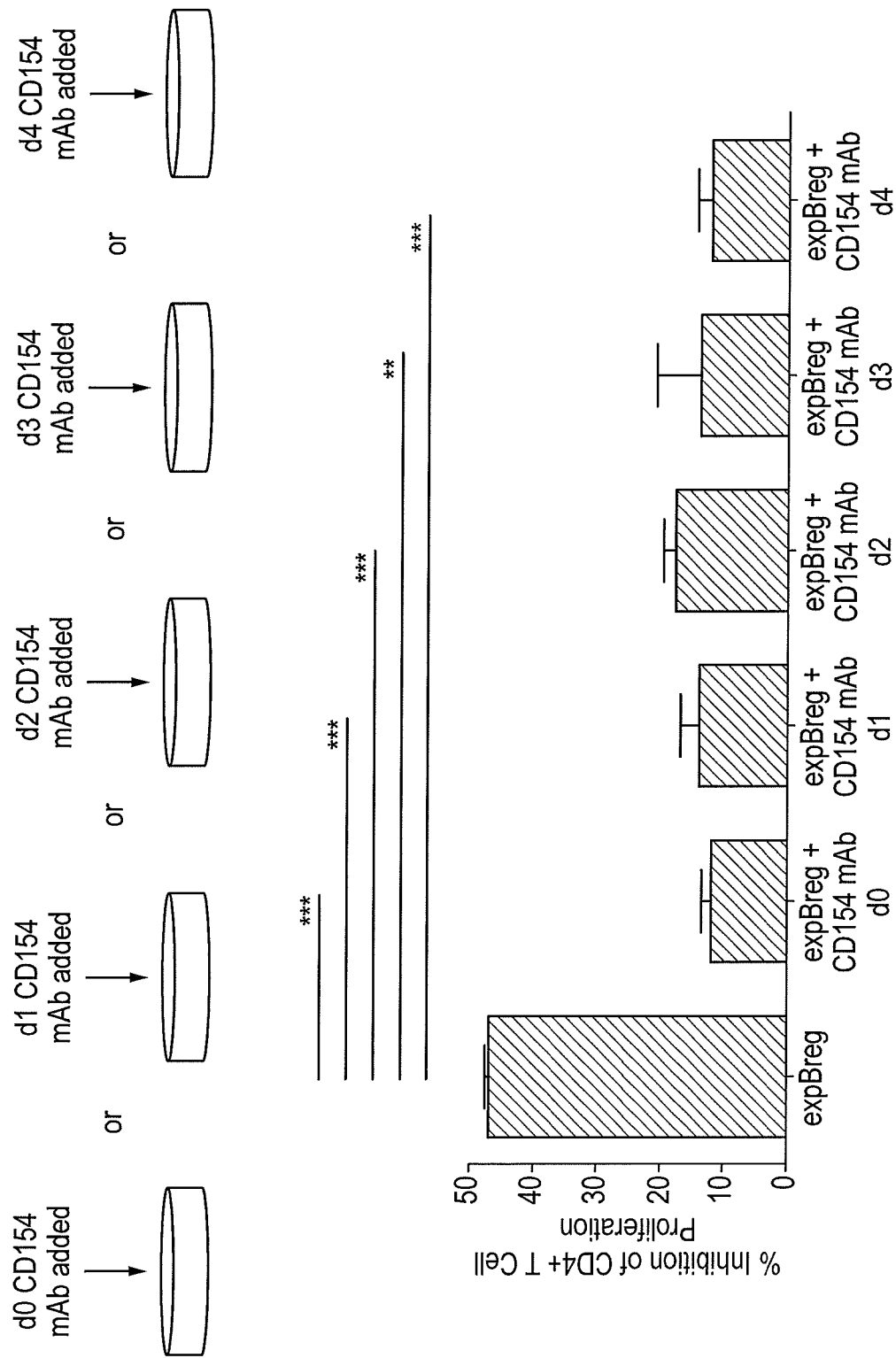

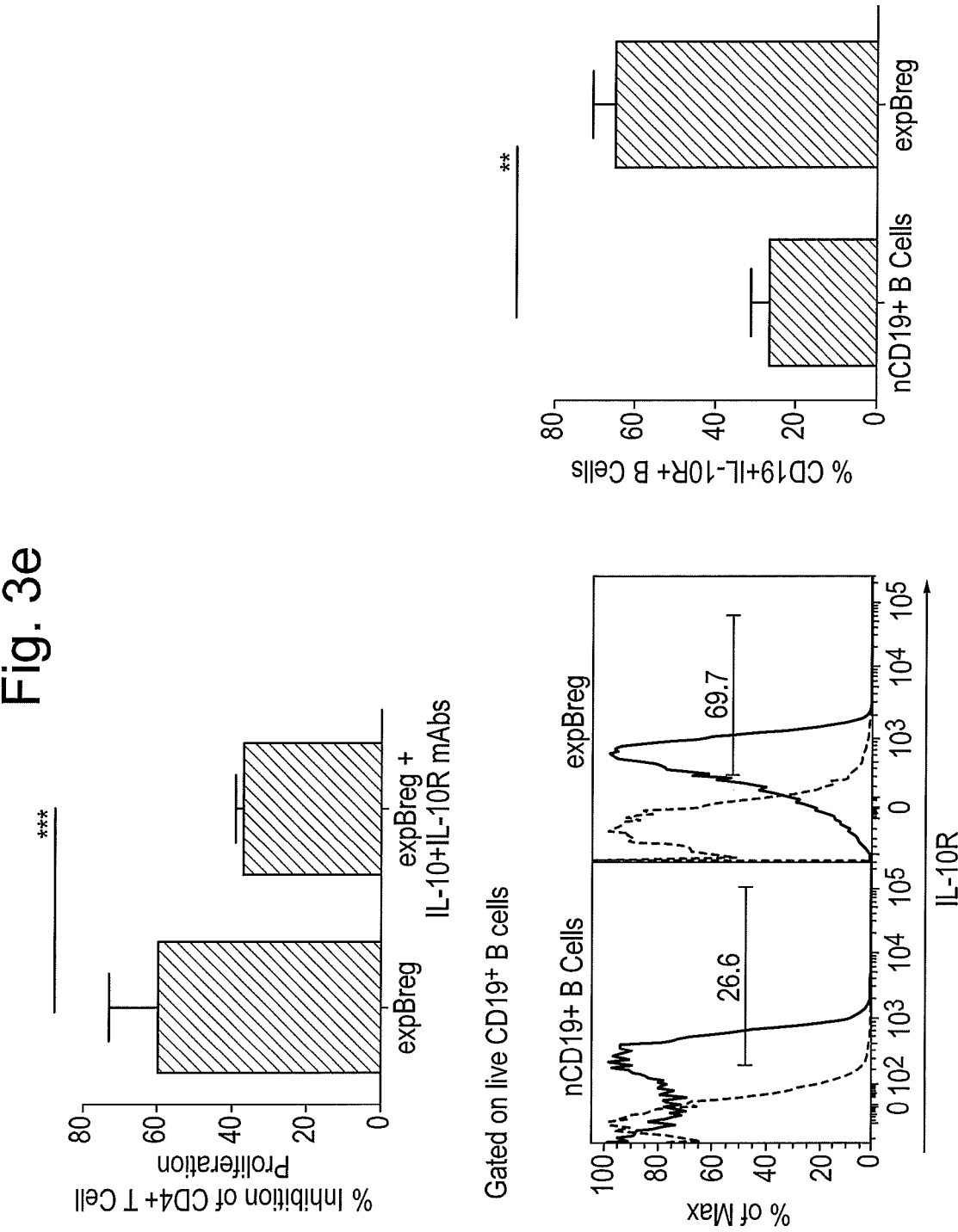

Gated on live CD19+ B cells

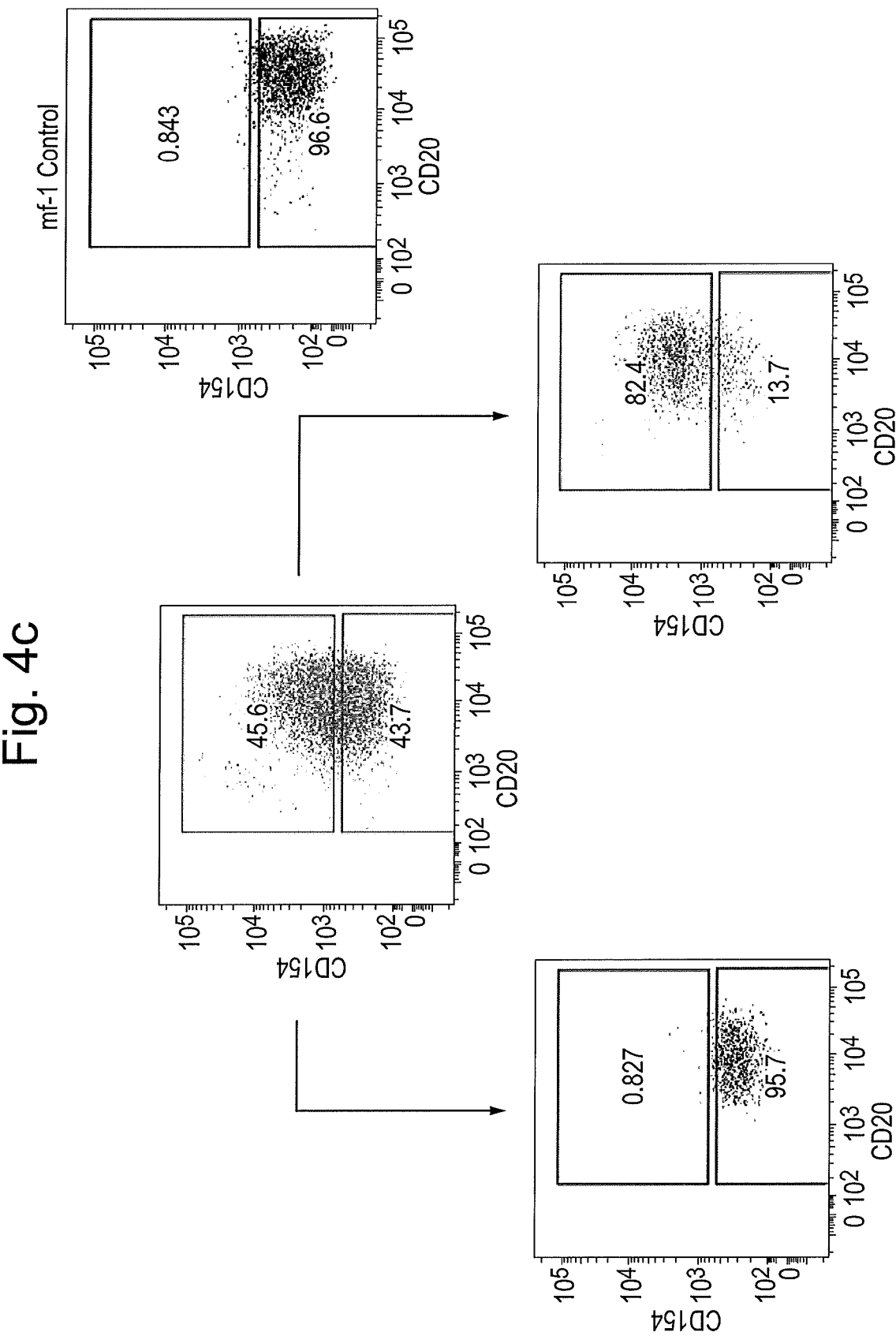

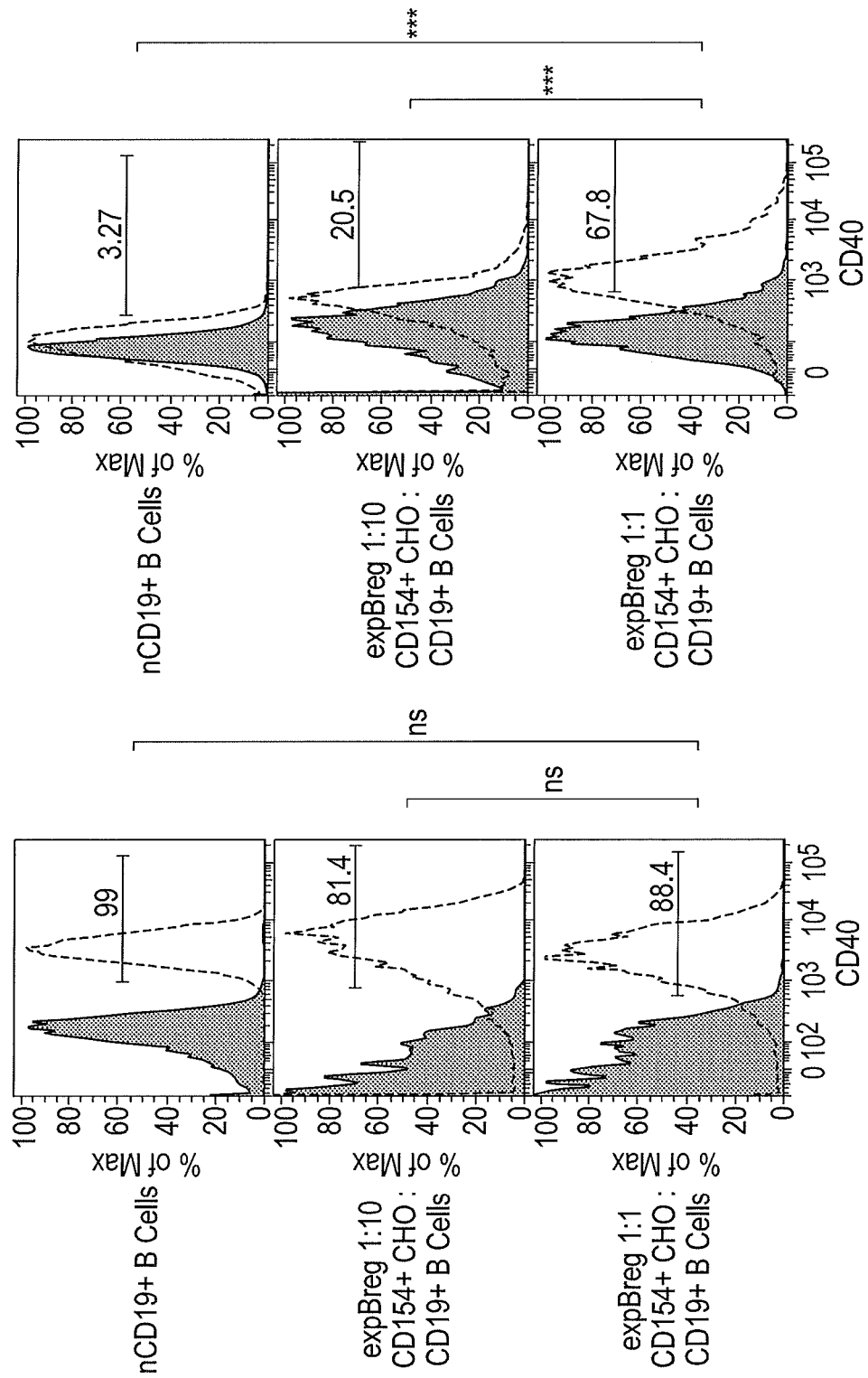

Gated on live huCD45+CD20+ B cells

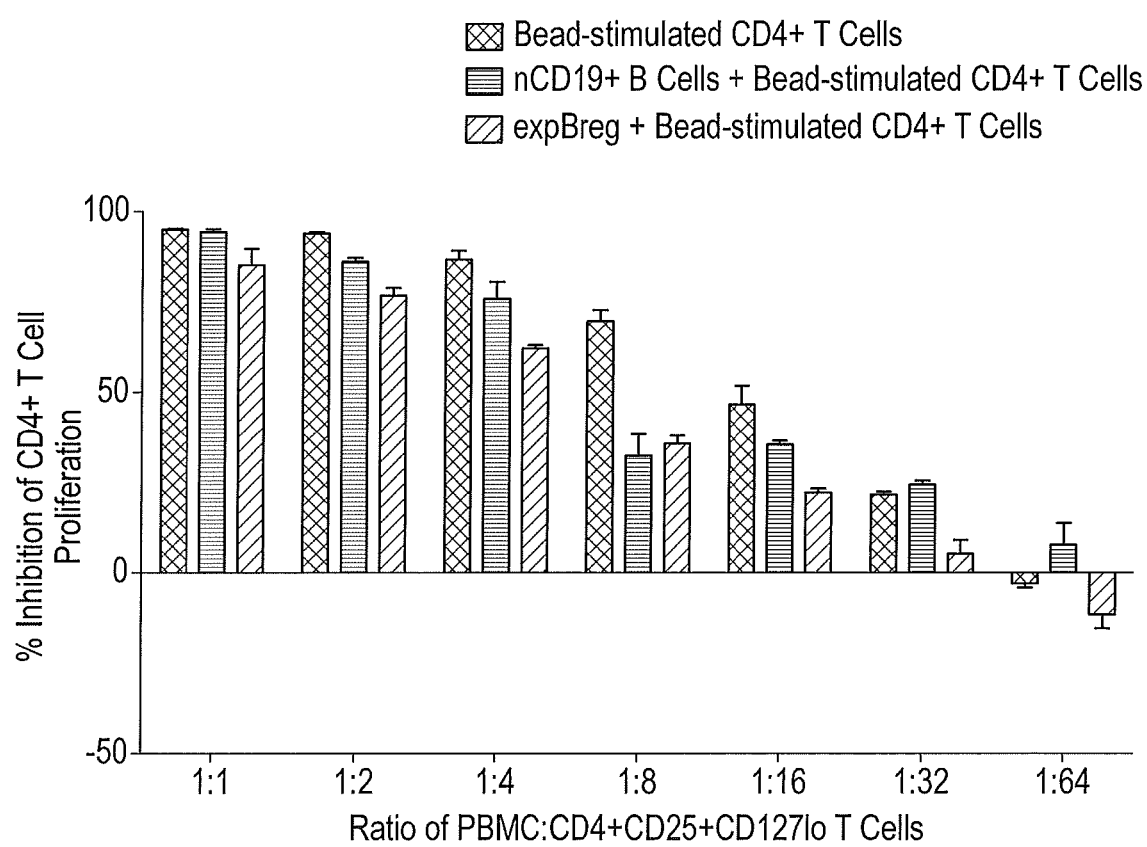

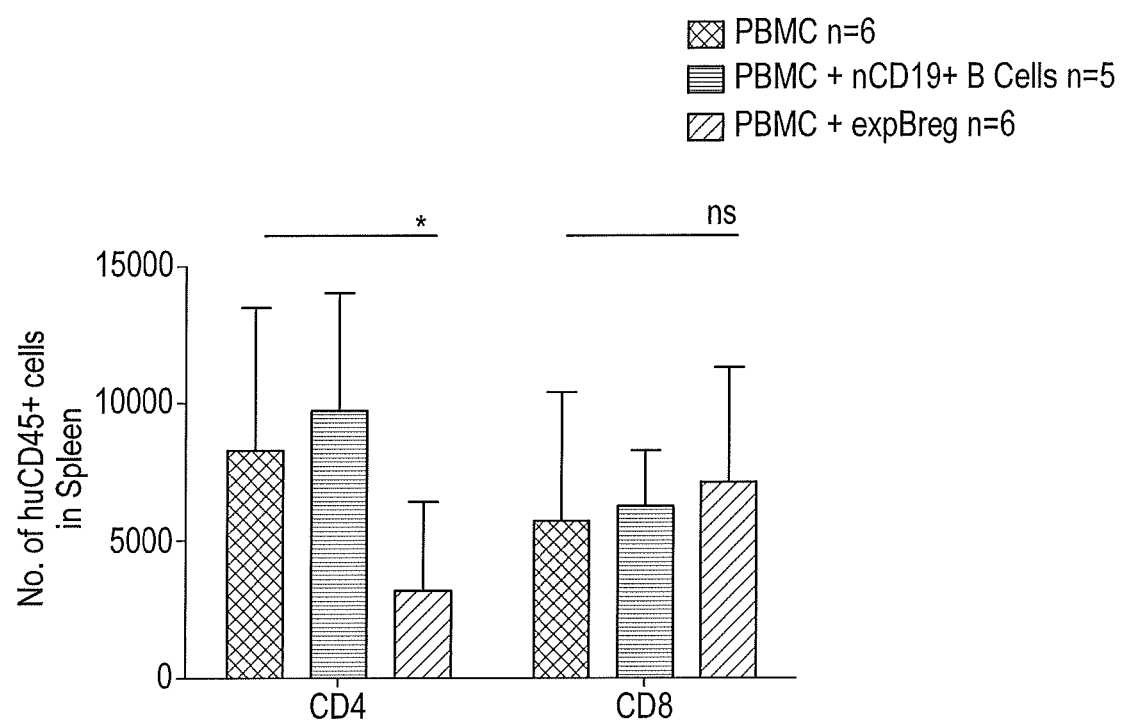

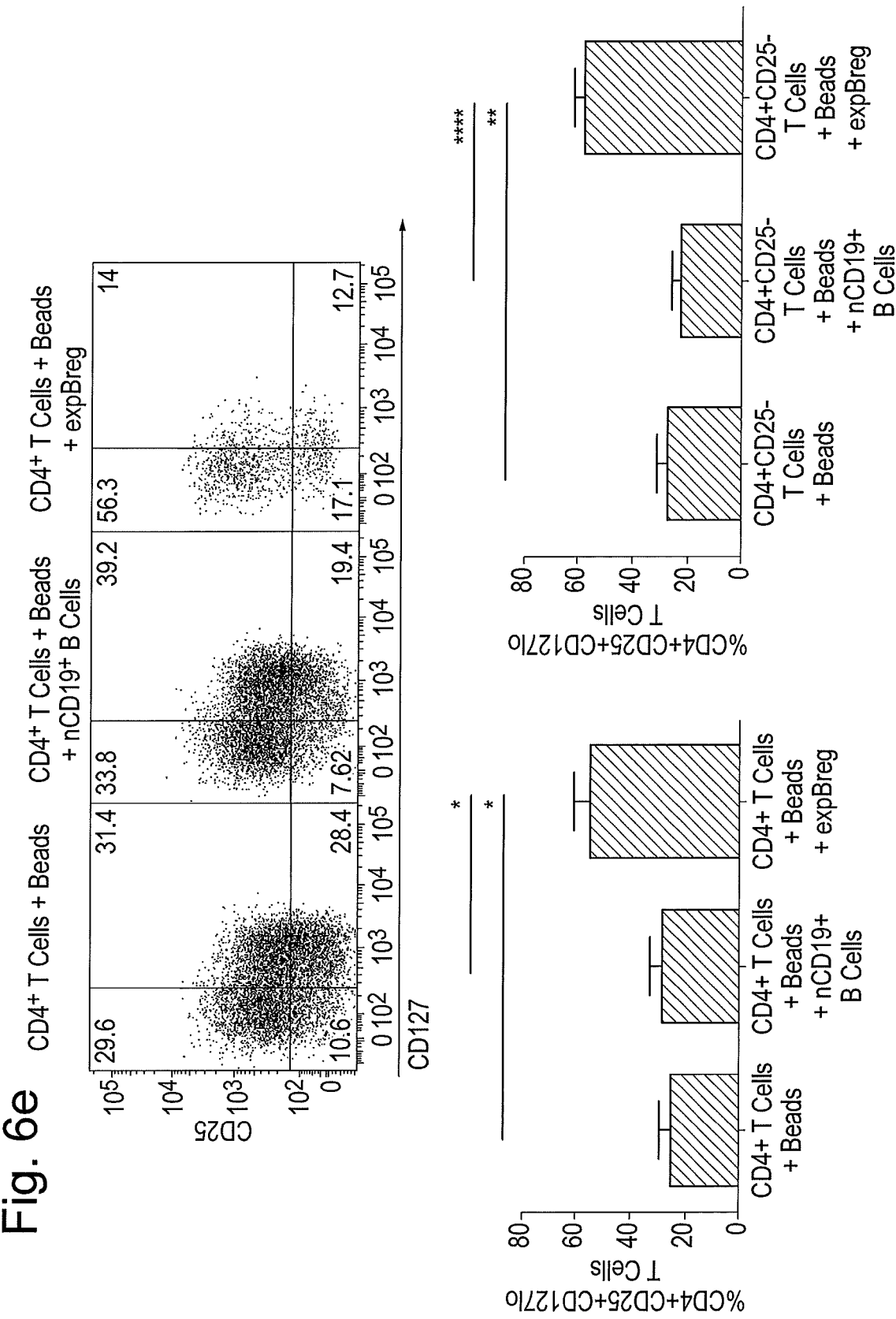

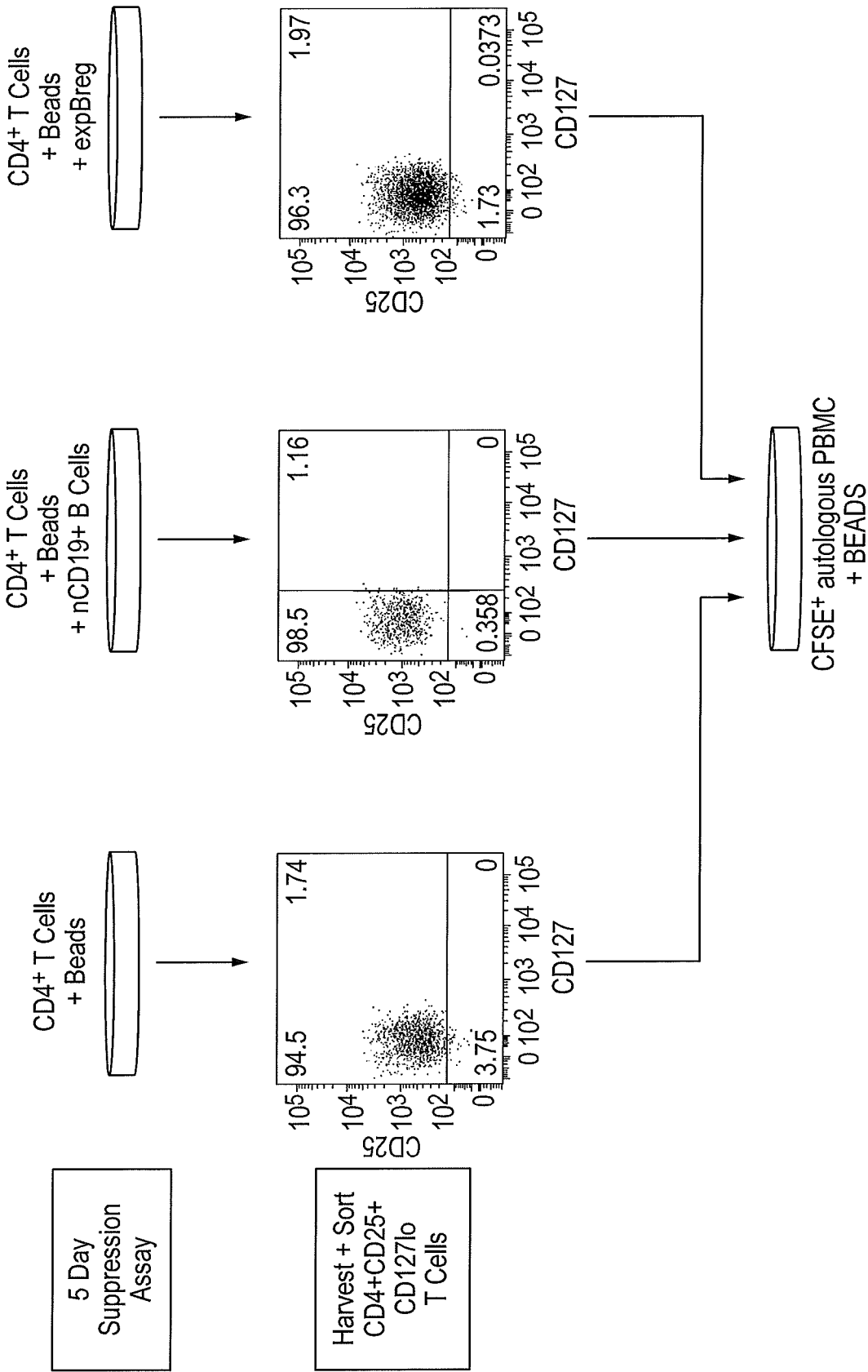

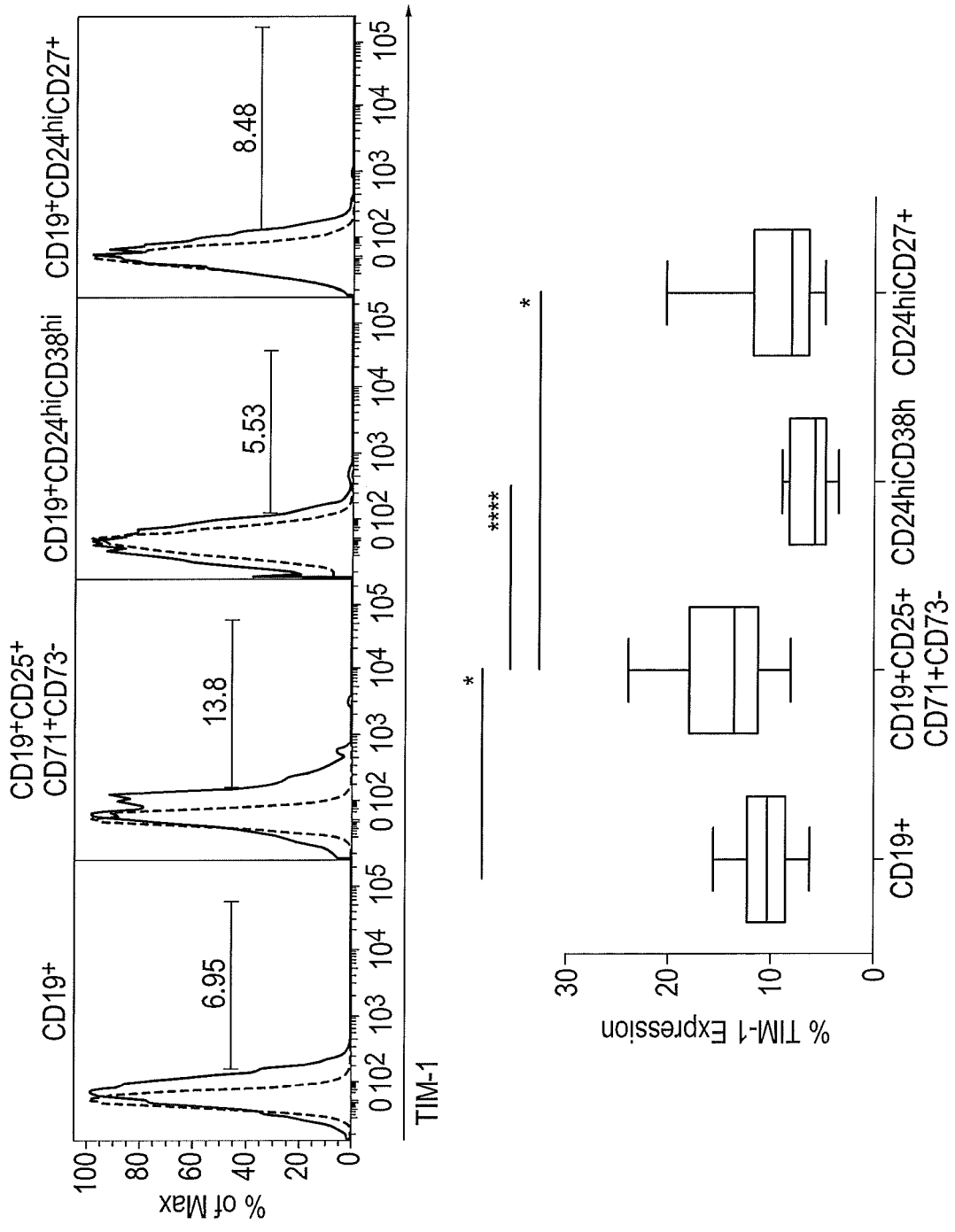

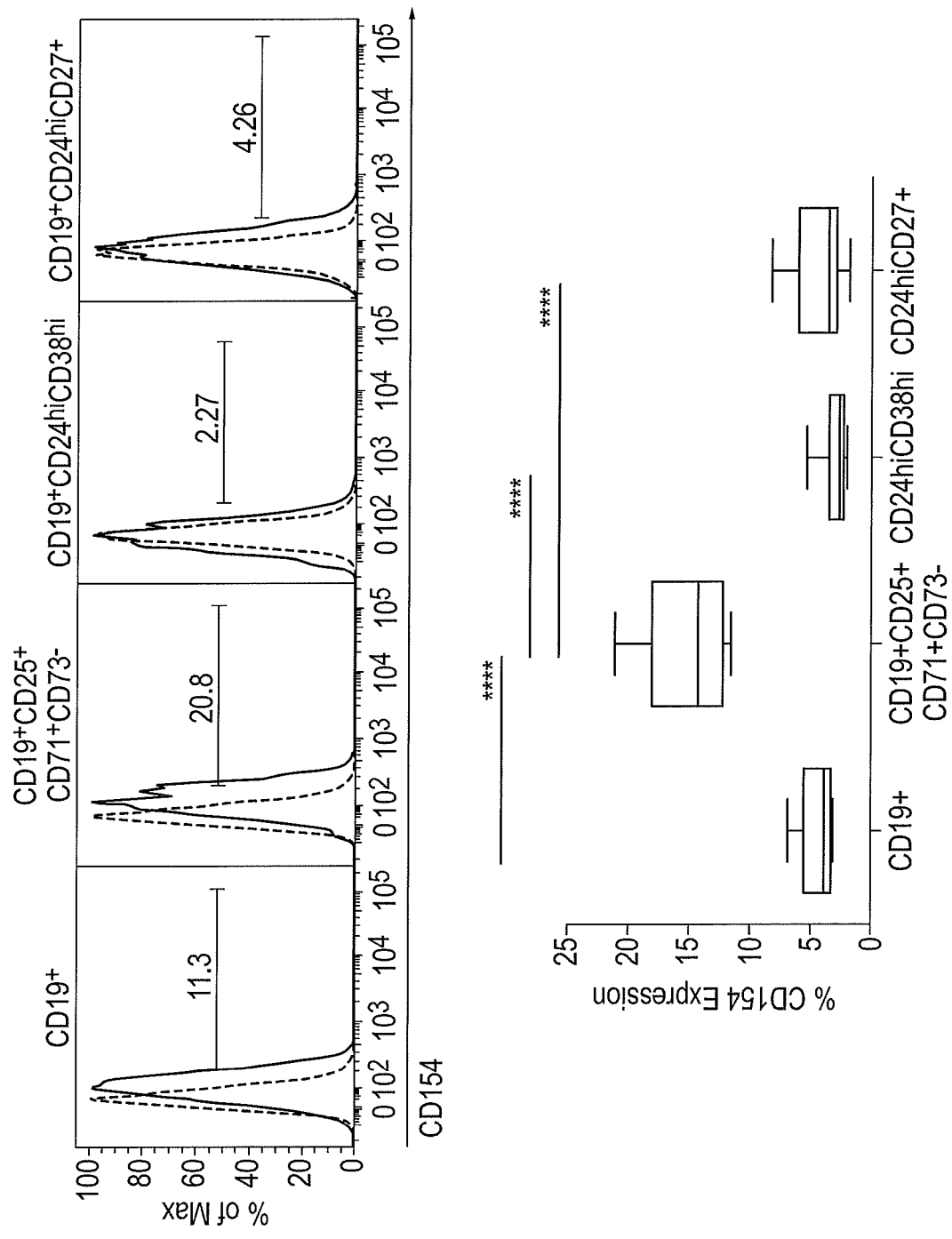

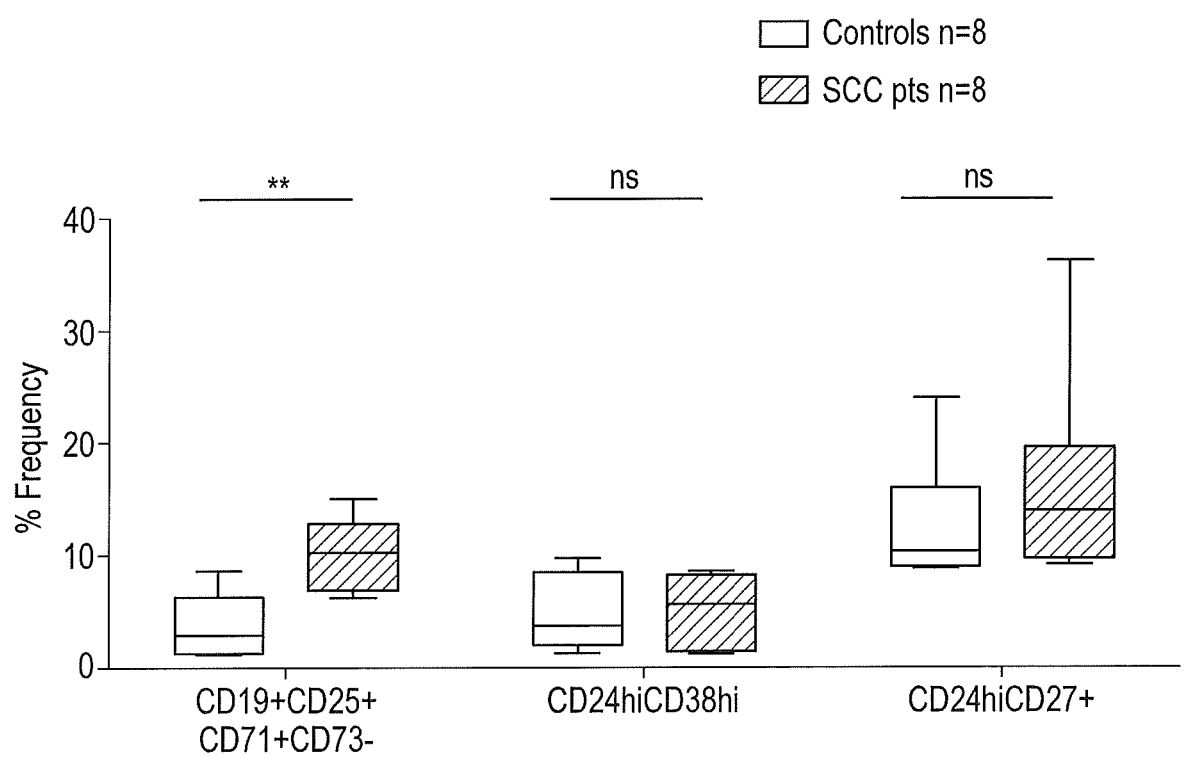

Gated on CD19+CD73- B cells

| | Sample | % | Gate |
|---|---|---|---|
| ☐⊞ | B cell test_L4-5 STAINED.fcs | 62.9 | CD154+ |
| ⊡⊞ | B cell test_CHO STAINED.fcs | 26 | CHO |
| ⊡⊞ | B cell test_CHO UNSTAINED.fcs | 25.7 | CHO |

COMPOSITION COMPRISING B REGULATORY CELLS

CROSS-REFERENCE TO RELATED APPLICATIONS

This application is the National Stage of International Application No. PCT/GB2018/051192, filed May 3, 2018, which claims priority to GB 1707238.0, filed May 5, 2017, which are entirely incorporated herein by reference.

FIELD OF THE INVENTION

The present invention relates to an expanded population of human Breg cells having the phenotype $CD19^+CD73^-CD71^+CD25^+TIM\text{-}1^+$ and methods for producing the cell population of the invention. The invention also relates to pharmaceutical compositions comprising the cell populations of the invention and their use in the treatment of immune-mediated disorders.

BACKGROUND TO THE INVENTION

The importance of $IL\text{-}10^+$ B regulatory cells (Breg) in both health and disease has rapidly become evident over the last decade [1-5]. Breg are able to control immune responses in animal models of transplantation and autoimmunity [6-10] whilst excessive regulation by Breg may contribute to the development of carcinoma and diseases such as Human Immunodeficiency Virus (HIV-1) [11-14]. Despite the successful expansion of mouse Breg [15-17], the rarity of human Breg in peripheral blood and difficulties with characterisation [3, 4, 18] mean that in vivo investigation and the potential for human Breg as a clinical therapy remain elusive.

SUMMARY OF THE INVENTION

The present inventors demonstrate for the first time, ex vivo expansion of human B cells with in vivo regulatory function. These Breg cells were able to significantly prolong human allograft survival in a humanized mouse model of skin transplantation, and were associated with an increase in percentage of human $CD4^+CD25^+CD127^{lo}$ Treg within the allograft. The present Inventors have characterized a novel mechanism by which TIM-1 regulates the response of the expanded Breg cells to autocrine IL-10 and modulates downstream suppressive function. Furthermore, a significant increase in $CD19^+CD73^-CD25^+CD71^+$ B cells was identified in peripheral blood of human subjects with squamous cell carcinoma of the skin (SCC), unlike other human Breg subsets, when compared to healthy controls.

The present invention provides an isolated population of cells, wherein the population comprises human Breg cells, having the phenotype $CD19^+CD73^-CD71^+CD25^+TIM\text{-}1^+$. In some embodiments of the invention at least 50% of the human Breg cells in the cell population express CD19 and at least 50% of the human Breg cells in the cell population do not express CD73 and at least 50% of the human Breg cells in the cell population express CD71 and at least 50% of the human Breg cells in the cell population express CD25 and at least 50% of the human Breg cells in the cell population express TIM-1. The invention further provides pharmaceutical compositions comprising the isolated population of cells of the invention and a pharmaceutically acceptable carrier.

The present invention also encompasses the cell populations or pharmaceutical compositions of the invention for use in a method of modulating the immune response in an individual in need thereof or for use in a method of treatment of an immune-mediated disorder.

The present invention further provides a method for producing a human Breg cell population comprising:
 isolating human $CD19^+$ B cells;
 culturing said $CD19^+$ B cells in the presence of a CD40 agonist and at least one cytokine or growth factor for at least 3 days;
 harvesting the Breg cells so produced.

Also encompasses by the present invention are expanded human Breg cell populations obtained by the methods of the invention.

The present invention also provides:
 A method of assessing Breg cell function in a subject, the method comprising:
  quantifying the number and/or percentage of human B cells having a phenotype $CD73^-CD71^+CD25^+$, $TIM\text{-}1^+$, $CD154^+$, $CD73^-CD71^+CD25^+CD154^+$, $CD73^-CD71^+CD25^+TIM\text{-}1^+$, or $CD73^-CD71^+CD25^+TIM\text{-}1^+CD154^+$ in a sample obtained from the subject; and
  comparing the number and/or percentage of human B cells having the phenotype $CD73^-CD71^+CD25^+$, $TIM\text{-}1^+$, $CD154^+$, $CD73^-CD71^+CD25^+CD154^+$, $CD73^-CD71^+CD25^+TIM\text{-}1^+$, or $CD73^-CD71^+CD25^+TIM\text{-}1^+CD154^+$ in the subject sample to the number of human B cells having the phenotype $CD73^-CD71^+CD25^+$, $TIM\text{-}1^+CD154^+$, $CD73^-CD71^+CD25^+CD154^+$, $CD73^-CD71^+CD25^+TIM\text{-}1^+$, or $CD73^-CD71^+CD25^+TIM\text{-}1^+CD154^+$ in a control;
 wherein a significantly larger number and/or percentage of human Breg cells having the phenotype $CD73^-CD71^+CD25^+$, $TIM\text{-}1^+CD154^+$, $CD73^-CD71^+CD25^+CD154^+$, $CD73^-CD71^+CD25^+TIM\text{-}1^+$, or $CD73^-CD71^+CD25^+TIM\text{-}1^+CD154^+$ in the patient sample compared to the control indicates increased Breg cell function in the subject.

A method of assessing Breg cell function in a subject, the method comprising:
  isolating human $CD73^-CD71^+CD25^+$, $TIM\text{-}1^+CD154^+$, $CD73^-CD71^+CD25^+CD154^+$, $CD73^-CD71^+CD25^{+TIM\text{-}}1^+$, or $CD73^-CD71^+CD25^+TIM\text{-}1^+CD154^+$ Breg cells from the subject;
  measuring the function of the Breg cells so isolated.

A method of assessing Breg function in a subject, the method comprising:
  isolating human $CD19^+$ B cells from a subject;
  culturing said $CD19^+$ B cells in the presence of a CD40 agonist and at least one cytokine or growth factor for at least 3 days;
  determining the phenotype and/or the function of the Breg cells so produced.

A method for monitoring the progression or regression of a disease in a subject, the method comprising:
  isolating a first sample of human $CD19^+$ B cells from the subject;
  culturing said $CD19^+$ B cells in the presence of a CD40 agonist and at least one cytokine or growth factor for at least 3 days;
  determining the phenotype and/or function of the Breg cells so produced;
  isolating a second sample of human $CD19^+$ B cells from the subject;

culturing said CD19$^+$ B cells in the presence of a CD40 agonist and at least one cytokine or growth factor for at least 3 days;

determining the phenotype and/or function of the Breg cells so produced;

comparing the phenotype and/or function of the Breg cells produced from the first sample of human CD19$^+$ B cells isolated from the subject with the phenotype and/or function of the Breg cells produced from the second sample of human CD19$^+$ B cells isolated from the subject;

wherein an increase in the number and/or percentage of Breg cells having a phenotype of CD73$^-$CD71$^+$CD25$^+$, TIM-1$^+$CD154$^+$, CD73$^-$CD71$^+$CD25$^+$CD154$^+$, CD73$^-$CD71$^+$CD25$^+$TIM-1$^+$, or CD73$^-$CD71$^+$CD25$^+$TIM-1$^+$CD154$^+$ or an increase in the Breg cell function indicates a regression of the disease in the subject.

A method for monitoring a subject's response to a treatment, the method comprising:

isolating human CD19$^+$ B cells from the subject prior to treatment;

culturing said CD19$^+$B cells in the presence of a CD40 agonist and at least one cytokine or growth factor for at least 3 days;

determining the phenotype and/or function of the Breg cells so produced;

isolating human CD19$^+$ B cells from the subject after treatment;

culturing said CD19$^+$ B cells in the presence of a CD40 agonist and at least one cytokine or growth factor for at least 3 days;

determining the phenotype and/or function of the Breg cells so produced;

comparing the phenotype and/or function of the Breg cells produced from the human CD19$^+$ B cells isolated from the subject before treatment with the phenotype and/or function of the Breg cells produced from the human CD19$^+$ B cells isolated from the subject after treatment;

wherein an increase in the number and/or percentage of Breg cells having a phenotype of CD73$^-$CD71$^+$CD25$^+$, TIM-1$^+$CD154$^+$, CD73$^-$CD71$^+$CD25$^+$CD154$^+$, CD73$^-$CD71$^-$CD25$^+$TIM-1$^+$, or CD73$^-$CD71$^+$CD25$^+$TIM-1$^+$CD154$^+$ or an increase in the Breg cell function indicates a positive response to the treatment in the subject.

A method of diagnosing, monitoring or predicting cancer or infection in a patient sample comprising:

comparing the number and/or percentage of human B cells having the phenotype CD73$^-$CD71$^+$CD25$^+$, TIM-1$^+$CD154$^+$, CD73$^-$CD71$^+$CD25$^+$CD154$^+$, CD73$^-$CD71$^+$CD25$^+$TIM- 1$^+$, or CD73$^-$CD71$^+$CD25$^+$TIM-1$^+$CD154$^+$ in the patient sample to the number and/or percentage of human B cells having said phenotype in a control;

wherein a larger number and/or percentage of human B cells having the phenotype CD73$^-$CD71$^+$CD25$^+$, TIM-1$^+$CD154$^+$, CD73$^-$CD71$^+$CD25$^+$CD154$^+$, CD73$^-$CD71$^+$CD25$^+$TIM- 1$^+$, or CD73$^-$CD71$^+$CD25$^+$TIM-1$^+$CD154$^+$ in the patient sample compared to the control indicates the patient has cancer, the patient has a more aggressive or advanced cancer or the patient is more likely to develop cancer; or indicates the patient has an infection, the patient has a more aggressive or advanced infection or the patient is more likely to develop an infection, compared to the control.

The present invention also provides an antibody that binds to TIM-1 on the surface of Breg cells for use in the treatment of cancer or infection;

an antibody that binds to IL-10R on the surface of Breg cells for use in the treatment of cancer or infection;

an antibody that binds to CD40 on the surface of Breg cells for use in the treatment of cancer or infection;

an antibody that binds to CD154 on the surface of Breg cells for use in the treatment of cancer or infection;

a bispecific antibody or antigen-binding fragment thereof that binds to TIM-1 and CD154, or TIM-1 and CD20, or CD154 and CD20, on the surface of Breg cells for use in the treatment of cancer or infection;

a tri-specific antibody or antigen-binding fragment thereof that binds to TIM-1, CD154 and CD20 on the surface of Breg cells for use in the treatment of cancer or infection;

a multi-specific antibody or antigen-binding fragment thereof that binds to TIM-1 and/or CD154 and any one of CD20, CD19, IL-10R, CD40, CD25, CD71, CD39, CD122 or B7-H4, or combinations thereof, on the surface of Breg cells for use in the treatment of cancer or infection.

Figure 1A:
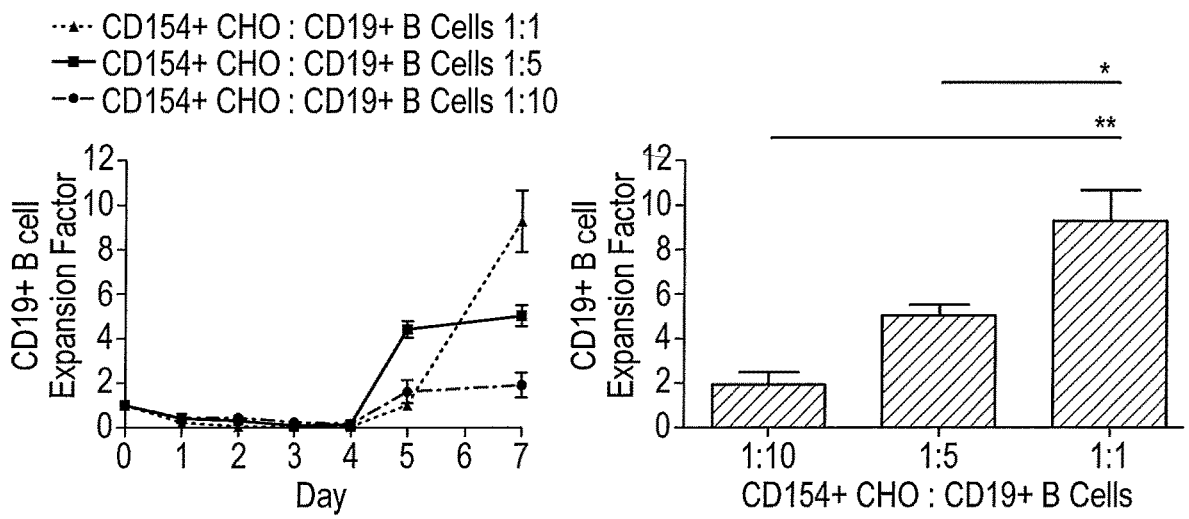
FIG. 1. Human CD19$^+$TIM-1$^+$ B regulatory cells can be generated ex vivo and express IL-10 (expBreg). (a) Greatest expansion of human CD19$^+$ B cells is achieved with a 1:1 CD154$^+$ CHO cell-CD19$^+$ B cell ratio, in the presence of IL-2, IL-4 and IL-10 for 7 days. Expansion factor is ratio of the number of live CD19$^+$ B cells at each day to the original number of live CD19+ B cells on day 0 (expansion factor at day 0=1). Purity of CD19$^+$ B cells >96% in all experiments. *p<0.05, **p<0.005, paired t-test. Data represent 3 independent experiments using CD19$^+$ B cells from 3 different human donors. (b) % Expression of IL-10 by CD19$^+$ B cells is increased following 7-day expansion, compared to autologous unstimulated CD19$^+$ B cells (nCD19$^+$ B cells). Representative histograms of IL-10 expression by live CD19$^+$ B cells are shown. Dashed line, isotype controls; solid line, CD19$^+$IL-10$^+$ B cells. *p<0.05, p<0.005, p<0.0005, paired t-test. Data represent 3 independent experiments using CD19$^+$ B cells from 3 different human donors. (c) >200 fold expansion of human CD19$^{+F}$IL-10$^+$ B cells is achieved at 1:1 CD154$^+$ CHO cell to CD19$^+$ B cell ratio for 7 days. Expansion factor is the ratio of the number of live CD19$^{+F}$IL-10$^+$ B cells at each day to the original number of live CD19$^+$IL-10$^+$ B cells on day 0 (expansion factor at day 0=1). *p<0.0001, paired t-test. Data represent 3 independent experiments using CD19$^+$ B cells from 3 different human donors. (d) expBreg suppress proliferation and inflammatory cytokine expression of autologous CD4$^+$ T cells in vitro. Autologous CD4$^+$CFSE$^+$ T cells were cultured with anti-CD3/CD28 beads for up to 5 days +/– expBreg or nCD19$^+$ B cells in increasing ratios. 0:1 represents stimulated CD4$^+$ T cell control in absence of B cells. % Inhibition of proliferation is an expression of Division Index of live CD4$^+$CFSE$^+$ T cells at day 5 relative to that of the stimulated CD4$^+$ T cell control 0:1. Representative histograms of live CD4$^+$CFSE$^+$ T cells, CD4$^+$IFNy$^+$ and CD4$^+$INFa$^+$ T cells are shown. Dashed line, isotype controls; solid lines, cytokine staining. *p<0.0001, paired t-test. Data represent 5 independent experiments using CD19$^+$ B cells from 5 different human donors. (e) expBreg are CD19$^+$CD73$^+$CD71$^+$CD25$^+$TIM-1$^+$. % Expression of the common gamma chain (yCR), CD25, CD122, CD71 and TIM-1 are up-regulated and CD73 is down-regulated by expBreg compared to nCD19+ B cells. Representative FACS plots of live CD19+ B cells demonstrate expBreg phenotype. Dashed line, fluorescence-minus-one (mf–1) control; solid line, TIM-1 staining. p<0.005, ***p<0.0001, paired t-test. Error bars represent Mean +/– SD. Data are representative of 5 independent experiments using CD19+ B cells from 5 different human donors.

Solid line, CD4+ T cells alone; dotted line, CD4+ T cells+ CD154-blocked-expBreg; dashed line, CD4+ T cells+exp-Breg. *p<0.05, paired t-test. (d) When CD154 expressed by expBreg is blocked, TIM-1 expression is unchanged. Mean fluorescence intensity (MFI) of CD73, CD71, CD25 and TIM-1 of expBreg and CD154-blocked-expBreg is shown. *p<0.05, **p<0.005, paired t-test. (e) IL-21 increases suppressive potency of expBreg. rhIL-21 was added to the last 48 hrs of the 7-day expBreg expansion co-culture with CD154+ CHO cells and cytokines IL-2, IL-4 and IL-10, and suppression of resulting expBreg (IL-21-stimulated exp-Breg) was assessed; Alternatively, rhIL-21 was directly added to the 5-day suppression assay comprising expBreg, CD4+ T cells and anti-CD3/CD28 beads. *p<0.05, paired t-test. (f) Suppressive potency of expBreg is dependent on level of CD154 expression by CHO cells. CD154+CHO cells were FACS-sorted to isolate the higher and lowest 10% of CD154+CHO cells, denoted as CD154$^{hi}$ and CD154$^{lo}$ CHO cells. Purities >96%. CD154$^{hi}$ CHO or CD154$^{lo}$ CHO cells were then co-cultured with polyclonal CD19+B cells and cytokines IL-2, IL-4 & IL-10 for 7 days. Suppressive capacity of resulting expBreg was examined. Graph illustrating difference in suppressive potency of expBreg cells which were generated with CD154$^{lo}$ CHO cells or CD154$^{hi}$ CHO cells. *p<0.05, paired t-test. (g) CHO cells express significantly higher levels of CD154 molecules per cell when compared to L4.5 cells. Representative histograms of live CHO and L4.5 cells are shown. Red line, unstained CHO cells; green line, CD154-antibody-stained L4.5 cells; blue line, CD154-antibody-stained CHO cells. (h) expBreg generated with CD154+CHO cells can suppress CD4+ T cell proliferation but expBreg generated with L4.5 cells are not suppressive. Representative histograms of live CD4+CFSE+ T cells are shown. Red line, CD4+ T cells alone; blue line, CD4+ T cells+expBreg. (i) expBreg can suppress proliferation of autologous CD8+ T cells. expBreg were co-cultured with CFSE+ peripheral blood mononuclear cells (PBMC) and anti-CD3/CD28 beads for 5 days. Representative histograms of live CD4+ CFSE+ T cells and CD8+ CFSE+ T cells are shown. Red line, CD4+ T cells or CD8+ T cells alone; blue line, CD4+ T cells or CD8+ T cells+expBreg; paired t-test. Data are representative of 3 independent experiments with 3 different human donors.

DETAILED DESCRIPTION OF THE INVENTION

The present invention relates to an isolated population of cells, wherein the population comprises human Breg cells, having a phenotype as described herein. We also describe herein methods of producing such human Breg cell populations comprising isolating human CD19+ B cells, culturing the CD19+ B cells in the presence of a CD40 agonist and at least one cytokine or growth factor for at least 3 days and harvesting the Breg cells so produced. We further describe the use of such human Breg cell populations in modulating the immune response in an individual in need thereof or in the treatment of an immune-mediated disorder.

Cell Populations

The present invention relates to an isolated population of cells, wherein the population comprises human Breg cells having a phenotype. The phenotype may be CD19+CD73−CD71+CD25+TIM-1+ or CD19+CD73+CD71+CD25+CD154+. In preferred embodiments, the phenotype may be CD19+CD73−CD71+CD25+TIM-1+CD154+.

The phenotype of human Breg cells is typically characterised by determining whether the cells express or do not express certain markers. Typically, expression of certain cell-surface markers on the human Breg cells may be determined by staining using fluorochrome-coupled antibodies specific for selected cell-surface markers, followed by flow cytometry. Typically, expression of certain intracellular markers may be determined by staining after permeabilisation of the cells using fluorochrome-coupled antibodies specific for intracellular markers, followed by flow cytometry. Examples of markers that may be detected using these typical methods include CD19, CD73, CD71, CD25, TIM-1, CD39, CD24, CD38, CD127, pSTAT3, CD20, CD4, CD8, γCR, CD27, CD138, CD1d, CD5, CD21, LAP, IL-10, TNFα, IFNγ, CD154, CD40, IL-10R, CD122, CD10, CD45.

One of skill is readily able using the methods described above to accurately determine whether cells are positive or negative for a particular marker. A cell population has a positive phenotype (X+) wherein at least 40%, 50%, 60%, 65%, 70%, 75%, 80%, 85%, 90%, 95%, 96%, 97% or 98% of the cells in the cell population express that particular marker. In some preferred embodiments between 40-90% of the cells in the cell population express that particular marker. Preferably, between 70-90% of the cells in the cell population express that particular marker. Preferably, at least 70% of the cells in the cell population express that particular marker. A cell population has a negative (X−) phenotype wherein more than 40%, 50%, 60%, 65%, 70%, 75%, 80%, 85%, 90%, 95%, 96%, 97% or 98% of cells in the cell population do not express that marker. In some preferred embodiments between 40-90% of the cells in the cell population do not express that particular marker. Preferably, between 70-90% of the cells in the cell population do not express that particular marker. Preferably, at least 70% of the cells in the cell population do not express that particular marker.

Where the expression of multiple markers is determined to define the phenotype, at least 40%, 50%, 60%, 65%, 70%, 75%, 80%, 85%, 90%, 95%, 96%, 97% or 98% of the cells in the overall cell population express/do not express each marker. In some preferred embodiments between 40-90% of the cells in the cell population express/do not express that particular marker. Preferably, between 70-90% of the cells in the cell population express/do not express that particular marker. Preferably, at least 40% of the cells in the cell population express/do not express that particular marker.

The present invention provides an isolated population of cells, wherein the population comprises human Breg cells, having the phenotype CD19+CD73−CD71+CD25+TIM-1+. In one embodiment at least 40%, typically at least 50%, such as between 50-90%, of the cells in the cell population express CD19 and at least 40%, typically at least 50%, such as between 50-90%, of the cells in the cell population do not express CD73 and at least 40%, typically at least 50%, such as between 50-90%, of the cells in the cell population express CD71 and at least 40%, typically at least 50%, such as between 50-90%, of the cells in the cell population express CD25 and at least 40%, typically at least 50%, such as between 50-90%, of the cells in the cell population express TIM-1. In a preferred embodiment at least 60%, typically at least 70%, such as between 70-90%, of the cells in the cell population express CD19 and at least 60%, typically at least 70%, such as between 70-90%, of the cells in the cell population do not express CD73 and at least 60%, typically at least 70%, such as between 70-90%, of the cells in the cell population express CD71 and at least 60%, typically at least 70%, such as between 70-90%, of the cells in the cell population express CD25 and at least 60%, typically at least 70%, such as between 70-90%, of the cells in the cell population express TIM-1. In a particularly preferred embodiment at least 60% of the cells in the cell population express CD19 and at least 60% of the cells in the cell population do not express CD73 and at least 60% of the cells in the cell population express CD71 and at least 60% of the cells in the cell population express CD25 and at least 60% of the cells in the cell population express TIM-1. In some embodiments, at least 40%, typically at least 50%, such as between 50-90%, of the cells in the cell population express CD19, CD71, CD25 and TIM-1 and do not express CD73. In some preferred embodiments, at least 60%, typically at least 70%, such as between 70-90%, of the cells in the cell population express CD19, CD71, CD25 and TIM-1 and do not express CD73. The present inventors have found that TIM-1 regulates STAT3 phosphorylation in TIM-1$^+$ Breg cells, thereby controlling Breg function.

The above-described isolated population of human Breg cells having the phenotype CD19$^+$CD73$^-$CD71$^+$CD25$^+$TIM-1$^+$, may further express CD154, CD39 or IL-10R, or CD154 and IL-10R, or CD154 and CD39, or CD39 and IL-10R, or CD154, CD39 and IL-10R. In preferred embodiments, the above-described isolated population of human Breg cells having the phenotype CD19$^+$CD73$^-$CD71$^+$CD25$^+$TIM-1$^+$, further expresses CD154. In some embodiments the isolated population of human Breg cells has the phenotype CD19$^+$CD73$^-$CD71$^+$CD25$^+$TIM-1$^+$CD154$^+$, or CD19$^+$CD73$^-$CD71$^+$CD25$^+$TIM-1$^+$CD39$^+$, or CD19$^+$CD73$^-$CD71$^+$CD25$^+$TIM-1$^+$IL-10R$^+$, or CD19$^+$CD73$^-$CD71$^+$CD25$^+$TIM-1$^+$CD154$^+$IL-10R$^+$, or CD19$^+$CD73$^-$CD71$^+$CD25$^+$TIM-1$^+$CD154$^+$CD39$^+$, or CD19$^+$CD73$^-$CD71$^+$CD25$^+$TIM-1$^+$IL-10R$^+$CD39$^+$, or CD19$^+$CD73$^-$CD71$^+$CD25$^+$TIM-1$^+$CD154$^+$CD39$^+$IL-10R$^+$. In preferred embodiments, the isolated population of human Breg cells has the phenotype CD19$^+$CD73$^-$CD71$^+$CD25$^+$TIM-1$^+$CD154$^+$. In some embodiments, the isolated population of human Breg cells has the phenotype CD19$^+$CD73$^-$CD71$^+$CD25$^+$TIM-1$^+$CD154$^+$CD39$^+$IL-10R$^+$. In accordance with the invention as described above, at least 40%, typically at least 50%, such as between 50-90%, of the cells in the cell population express each of CD19, CD71, CD25, TIM-1 and CD154, CD39 or IL-10R, or CD154 and IL10R, or CD154 and IL-10R, or CD154 and CD39, or CD39 and IL-10R, or CD154, CD39 and IL-10R; and do not express CD73. Preferably, in accordance with the invention as described above, at least 60%, typically at least 70%, such as between 70-90%, of the cells in the cell population express each of CD19, CD71, CD25, TIM-1 and CD154, CD39 or IL-10R, or CD154 and IL10R, or CD154 and IL-10R, or CD154 and CD39, or CD39 and IL-10R, or CD154, CD39 and IL-10R; and do not express CD73. Most preferably, in accordance with the invention as described above, at least 60%, typically at least 70%, such as between 70-90%, of the cells in the cell population express each of CD19, CD71, CD25, TIM-1 and CD154; and do not express CD73. Thus, in preferred embodiments the isolated population of human Breg cells express TIM-1 and CD154. In some embodiments, expression of both TIM-1 and CD154 may be required for the regulatory function of the isolated population of human Breg cells (i.e., suppression of CD4$^+$ T cell proliferation).

In one embodiment, the isolated population of human Breg cells having the phenotype CD19$^+$CD73$^-$CD71$^+$CD25$^+$TIM-1$^+$, further do not express one or more of CD5, CD1d, CD24, CD27, CD21 and/or CD38. Preferably, the isolated population of human Breg cells having the phenotype CD19$^+$CD73$^-$CD71$^+$CD25$^+$TIM-1$^+$, further do not express CD5 and CD1d. Typically the isolated population of human Breg cells having the phenotype CD19$^+$CD73$^-$CD71$^+$CD25$^+$TIM-1$^+$ do not express any of CD5, CD1d, CD24, CD27, CD21 and/or CD38. Therefore, in some embodiments the isolated population of human Breg cells having the phenotype CD19$^+$CD73$^-$CD71$^+$CD25$^+$TIM-1$^+$, further have the phenotype CD5$^-$CD1d$^-$CD24$^-$CD27$^-$CD21$^-$CD38$^-$. In some preferred embodiments the isolated population of human Breg cells has the phenotype CD19$^+$CD73$^-$CD71$^+$CD25$^+$TIM-1$^+$CD5$^-$CD1d$^-$, more preferably CD19$^+$CD73$^-$CD71$^+$CD25$^+$TIM-1$^+$CD154$^+$CD5$^-$CD1d$^-$.

In accordance with the invention as described above, at least 40%, typically at least 50%, such as between 50-90% and preferably 70-90%, of the cells in the cell population express each of CD19, CD71, CD25, TIM-1 and at least 40%, typically at least 50%, such as between 50-90%, and preferably 70-90%, of the cells in the cell population do not express each of CD73, CD5, CD1d, CD24, CD27, CD21 and/or CD38.

In some embodiments the above-described isolated population of human Breg cells having the phenotype CD19$^+$CD73$^-$CD71$^+$CD25$^+$TIM-1$^+$ or CD19$^+$CD73$^-$CD71$^+$CD25$^+$TIM-1$^+$CD154$^+$ further do not express IL-10. Typically less than 50%, 40%, 35%, 30%, 25%, 20%, 15% or 10% of the cells in the cell population express IL-10. Preferably, between 20-40% of the cells in the cell population express IL-10. In a particularly preferred embodiment less than 30% of the cells in the cell population express IL-10. In some embodiments the regulatory function of the isolated population of human Breg cells (i.e., suppression of CD4$^+$ T cell proliferation), is not dependent on IL-10 expression. In some embodiments the isolated population of human Breg cells retains regulatory function when IL-10 is blocked (e.g., using antibodies targeting IL-10 or IL-10R).

In some preferred embodiments, the isolated population of human Breg cells is an expanded population of human Breg cells. The human Breg cells, having a phenotype as described above, may be present in the isolated population of cells at an amount of at least $10^5$, $10^6$, $10^7$, $10^8$ cells/ml.

Methods for Producing the Cell Populations

The present invention also relates to a method for producing a human Breg cell population comprising:
  isolating human CD19$^+$ B cells;
  culturing said CD19$^+$ B cells in the presence of a CD40 agonist and at least one cytokine or growth factor for at least 3 days;
  harvesting the Breg cells so produced.

The method is a method for expanding human B cells. The term "expanding", particularly expanding human B cells, can be considered to include concurrently stimulating the proliferation of the cells and preventing cell death (e.g. through apoptosis). Thus the resulting cell population is an expanded population of human Breg cells. The methods of the inventions consistently results in greater than 50 fold, 100 fold, 150 fold, 200 fold, 250 fold or 300 fold expansion of human Breg cells. Thus, the Breg cells may be produced such that they are present in an amount of at least $10^5$, $10^6$, $10^7$, $10^8$ cells/ml.

The term "isolating" can be considered to refer to isolating cells for use in the methods of the invention from the human body. The cells for use in the methods of the invention may initially comprise a mixture of cell types, but human CD19$^+$ B cells must be present. The human CD19$^+$ B cells may be further isolated or purified from other cell types present. Typically this may be done by gradient centrifugation and subsequent negative selection using a human B cell enrichment kit. Human CD19$^+$ B cells may also be isolated by selecting for specific markers, including cell-surface markers. Methods for isolating human CD19$^+$ B cells from a mixed population of cells would be readily known to those of skill in the art, but may include fluorescence-activated cell sorting (FACS). The starting population of human CD19+ B cells is typically not enriched for IgG and therefore may comprise at least 50%, 60% or preferably at least 70% IgM$^+$ B cells (i.e., IgM-expressing B cells) and at least 50%, 60%, 70% or at least 80% IgD$^+$ B cells (i.e., IgD-expressing B cells). In some embodiments, the starting population of human CD19$^+$ B cells may comprise at least 50% IgM$^+$ B cells and at least 60% IgD$^+$ B cells, preferably at least 70% IgM$^+$ B cells and at least 80% IgD$^+$ B cells.

The cells for use in the methods of the invention may be isolated from a subject. The subject may be a patient, a donor or a recipient. In some embodiments the donor is chosen to be histocompatible with the intended recipient. The cells for use in the methods of the invention may be isolated from various areas of the subject, including the blood, spleen, peritoneal cavity, lymph nodes, bone marrow, skin, urine, tumour, cerebrospinal fluid, synovial fluid, site of autoimmune disease, site of inflammation or site of tissue transplant, the transplanted tissue may be undergoing rejection. Methods for isolating the cells from the subject are readily known by the person skilled in the art and any suitable means may be utilised. The human CD19$^+$ B cells may be isolated from a cell sample, for example, a peripheral blood mononuclear cell (PBMC) population may be isolated from leukocyte cones and human CD19$^+$B cells subsequently further isolated. Alternatively, the human CD19$^+$B cells may be derived from stem cells, including but not limited to B cell stem cells, bone marrow stem cells, embryonic stem cells and induced pluripotent stem cells, which have been appropriately differentiated in vitro to develop into human CD19$^+$ B cells.

The term "culturing" typically refers to mammalian cell culture methods, which are well known to the skilled person. For example, it may refer to incubation of the cells in cell culture medium at about 37° C. and in the presence of about 5% $CO_2$ for a period of time with other chosen additives that could be readily selected by the skilled person, but include different media, buffers, salts, sugars, serum (e.g. FCS), antibiotics or various other components. In the methods of the invention, isolated human CD19$^+$ B cells are cultured in the presence of a CD40 agonist and at least one cytokine or growth factor for at least 3, 4, 5, 6, 7, 8, 9, 10, 15, 20, 30, 40, 50, 60 days, such as between 3-60 days, preferably between 3-7 days.

The CD40 agonist may be CD154, the CD40 ligand, and protein fragments thereof; CD40 antibodies and fragments thereof; mimotopes and other mimetic agents; small molecules; drugs; peptides, polypeptides, proteins, nucleic acids, any other molecules capable of being a CD40 agonist. In one preferred embodiment the CD40 agonist is CD154, or a functional fragment thereof. The CD40 agonists may be expressed on the surface of cells and the CD19$^+$B cells are cultured in the presence of the cells expressing the CD40 agonists or the CD40 agonists may be added to the cell culture medium. In one preferred embodiment the CD40 agonist CD154 is expressed on the surface of cells. Suitable cells that express CD154 or can be genetically modified to express CD154 may be readily selected by the skilled person, but may include CHO cells, fibroblasts, endothelial cells, epithelial cells, keratinocytes, melanocytes, or other mesenchymal or stromal cells. Preferably, the cells are irradiated CHO cells expressing CD154. In some embodiments, the cells are not L4.5 cells. Expression of CD154 may be verified by any suitable means known to the person skilled in the art, for example flow cytometry analysis. Typically, soluble membrane fractions comprising CD154 are not suitable for use in the methods for producing a human Breg cell population described herein.

Thus, in preferred embodiments, the human CD19$^+$B cells may be co-cultured in the presence of cells expressing a CD40 agonist, preferably wherein the CD40 agonist is CD154. The cells may be co-cultured at a ratio of about 0.5:1, 1:1, 1:1.5, 1:2, 1:5 or 1:10 cells expressing a CD40 agonist (e.g. CHO cells) to human CD19$^+$ B cells. Preferably, the cells are co-cultured at a ratio of from about 1:1 to about 1:5 cells expressing a CD40 agonist (preferably CD154) to human CD19$^+$ B cells. Most preferably, the human CD19$^+$ B cells are co-cultured at a ratio of about 1:1 with cells expressing the CD40 agonist CD154.

Furthermore, in preferred embodiments the cells expressing CD154 express high levels of CD154, i.e., have the phenotype CD154$^{hi}$. In some embodiments, the cells expressing CD154 have, on average across the cell population, at least 2000, preferably at least 3000 CD154 molecules per cell. In some embodiments, the cells expressing CD154 have, on average across the cell population, from about 3000 to about 15000 CD154 molecules per cell, preferably from about 3000 to about 10000 CD154 molecules per cell, most preferably from about 3000 to about 8000 CD154 molecules per cell. Typically, the ratio of human CD19$^+$ B cells to cells, such as CHO cells, expressing CD154 and the level of CD154 expression, are important for determining the suppressive function of the Breg cells produced. Typically, fresh cells expressing a CD40 agonist (preferably CD154) are introduced in the co-culture at least every 1, 2, 3, 4, 5, 6, 7, 8, 9 or 10 days, such as at least every 2 days, preferably every 2-3 days.

The term "cytokine" can be considered to refer to a broad class of small proteins that are important in cell signaling, they are typically involved in autocrine, paracrine and endocrine signaling and immunomodulation. Cytokines may include chemokines, interferons, interleukins, lymphokines, and tumor necrosis factors. The term "growth factor" can be considered to refer to a naturally occurring substance capable of stimulating cell growth, proliferation, differentiation and healing, typically involved in cell signaling. Growth factors may include angiopoietin, bone morphogenetic proteins, colony-stimulating factors, epidermal growth factor, ephrins, erythropoeitin, fibroblast growth factor, GDNFs, interleukins, PDGF, thrombopoietin, T-cell growth factor, TGFs, VEGF, Wnt.

In some embodiments the human CD19$^+$ B cells are cultured in the presence of a CD40 agonist and at least one cytokine or growth factor selected from IL-2, IL-4 or IL-10. In some embodiments at least IL-2 is present. In some embodiments at least IL-4 is present. In some embodiments at least IL-10 is present. In some embodiments at least IL-2 and IL-4 are present. In some embodiments at least IL-2 and IL-10 are present. In some embodiments at least IL-4 and IL-10 are present. In some embodiments at least IL-2, IL-4 and IL-10 are present. In some embodiments at least IL-2, IL-4 and IL-10 are present simultaneously. In some embodiments, the human CD19$^+$ B cells are cultured in the presence of IL-2 and IL-10. In some embodiments, the human CD19$^+$ B cells are cultured in the presence of IL-2, IL-4 and IL-10. In some embodiments the human CD19$^+$ B cells are further cultured in the presence of IL-21. In some embodiments, the human CD19$^+$ B cells are cultured in the presence of IL-2, IL-4, IL-10 and IL-21.

In some embodiments the human CD19$^+$ B cells may be cultured in a first incubation in the presence of at least one of IL-2, IL-4 or IL-10, optionally followed by a second incubation in the presence of at least one of IL-2, IL-4 or IL-10 that was not present in the first incubation, optionally followed by a third incubation in the presence of at least one of IL-2, IL-4 or IL-10 that was not present in the first or second incubations. In some embodiments the human CD19$^+$B cells may be cultured in a first incubation in the presence of at least IL-2, IL-4 and IL-10 and in a second incubation in the presence of at least IL-2, IL-4, IL-10 and IL-21.

Suitable concentrations of each cytokine or growth factor can be readily selected by the skilled person and depend on the chosen culture conditions. In some embodiments a B cell survival promoter (e.g. BAFF) is not added to the human CD19$^+$ B cell culture. In some embodiments a calcineurin inhibitor is not added to the human CD19$^+$ B cell culture. In some embodiments IL-21 is not added to the human CD19$^+$ B cell culture. In some embodiments, the human CD19$^+$ B cells are not cultured in the presence of IL-11 and/or IL-6. In some embodiments, the human CD19$^+$ B cells are not cultured in the presence of insulin, cyclosporine A, transferrin and/or CpG oligodeoxynucleotides (CpG ODN) (short single-stranded synthetic DNA molecules comprising a CpG motif). The presence of at least one cytokine or growth factor, preferably each of the cytokines or growth factors present, may be replenished at least every 1, 2, 3, 4, 5, 6, 7, 8, 9, 10 days, such as at least every 2 days, preferably at least every 2-3 days. Such methods of cell culture and exchange of additives are well known to the person skilled in the art.

In a preferred embodiment, the human CD19$^+$ B cells are co-cultured (preferably at a ratio of 1:1) with cells expressing CD154, in the presence of IL-2, IL-4 and IL-10. Preferably the human CD19$^+$ B cells are co-cultured (preferably at a ratio of 1:1) with cells expressing CD154, in the presence of at least IL-2, IL-4 and IL-10, and optionally IL-21, for 3-7 days. In some embodiments the human CD19$^+$ B cells are co-cultured (preferably at a ratio of 1:1) with cells expressing CD154, in the presence of at least IL-2, IL-4 and IL-10 for 4 days and at least IL-2, IL-4, IL-10 and IL-21 for a further two days, wherein IL-2, IL-4 and IL-10 may be present on days 1-4 of the culture and IL-2, IL-4, IL-10 and IL-21 may be present on days 5-7 of the culture. In some embodiments the cells may be co-cultured for longer periods, for example at least 10, 20, 30, 40, 50, or 60 days. In some embodiments, IL-21 is not added to the human CD19$^+$ B cell culture during the culturing step of the methods for producing a human Breg cell population of the invention.

The term "harvesting" may include separating the human Breg cells produced by the methods of the invention from, for example, other cells, media, cell debris, the products of cell growth. Means for harvesting a particular cell population are well known to the person skilled in the art, but may include selecting for expression of cell-surface markers by fluorescence-activated cell sorting (FACS) or for binding to magnetic beads coated with antibodies specific for cell-surface markers. For example, harvesting the Breg cells produced by the methods of the invention may include selection for any of the following markers CD19$^+$, CD73$^-$, CD71$^+$, CD25$^+$, CD154$^+$ and/or TIM-1$^+$. Breg cells may be harvested after at least 3, 4, 5, 6, 7, 8, 9, 10, 12, 15, 20, 30, 40, 50 or 60 days of culturing according to the methods of the invention. Following harvesting, the Breg cells may comprise at least 40%, 50%, 60%, 70%, 80%, 85%, 90%, 95%, 96%, 97%, 98%, 99% or substantially 100% of the resulting cell population. The cell population produced by the methods described herein typically comprises at least 30%, 40% or preferably at least 50% IgM$^+$ cells and at least 50%, 60% or preferably at least 70% IgD$^+$ cells. The cell population produced by the methods described herein may comprise at least 30% IgM$^+$ cells and at least 50% IgD$^+$ cells, preferably at least 50% IgM$^+$ cells and at least 70% IgD$^+$ cells. In some embodiments the human Breg cell population produced using the methods described herein suppresses CD4$^+$ T cell proliferation. Preferably, the human Breg cell population produced using the methods described herein suppresses CD4$^+$ T cell proliferation and CD8$^+$ T cell proliferation.

The present invention also relates to an isolated population of cells, wherein the population comprises human Breg cells produced by the above-described methods of the invention. The human Breg cells produced by the methods of the invention may have the phenotype CD19$^+$CD73$^-$CD71$^+$CD25$^+$TIM-1$^+$, as above described. Preferably, the human Breg cells produced by the methods described herein further have the phenotype CD154$^+$. The human Breg cells produced by the methods described herein may further have the phenotype CD20$^+$CD38$^-$CD138$^-$. Typically, the human Breg cells produced by the methods described herein are not memory or plasma B cells.

In some embodiments, the methods of the invention may further comprise genetically modifying the human CD19$^+$ B cells prior to, during or after expansion, to express or delete, up-regulate or down-regulate a target antibody or antigen, wherein the target antibody or antigen is associated with an immune-mediated disorder. The skilled person is readily capable of selecting appropriate methods for genetically modifying human CD19$^+$ B cells to express or delete, up-regulate or down-regulate a particular target antibody or antigen. Such methods may include transfection of the human CD19$^+$ B cells with nucleic acids suitable for expression, deletion, activation of expression or inhibition of expression of the target antibody or antigen or editing the genome of the human CD19$^+$ B cells to introduce or remove nucleic acids or activate or inhibit endogenous genes suitable for expression, deletion, up-regulation or down-regulation of the target antibody or antigen (e.g. using CRISPR/Cas genome editing techniques).

Genetically modifying the human CD19$^+$ B cells, prior to, during or after expansion, to express, delete, up-regulate or down-regulate a target antibody or antigen that is associated with an immune-mediated disorder, will result in a population of human Breg cells expressing, not expressing, up-regulating or down-regulating the target antibody or antigen. These human Breg cells may also be introduced into a subject having the immune-mediated disorder, to increase regulatory (T) cell populations targeting that target antigen, in order to inhibit the immune response to that target antigen and thus treat the immune-mediated disorder in the subject. These human Breg cells may also be introduced into a subject having the immune-mediated disorder, to decrease or inhibit the effector (T) cell population targeting that target antigen in the subject, in order to inhibit the immune response to that target antigen and thus treat the immune-mediated disorder in the subject. Any immune-mediated disorder could be treated using the populations of genetically-modified human Breg cells expressing, not expressing, up-regulating or down-regulating the target antibody or antigen. Examples of immune-mediated disorders or conditions that may be treated are transplantation, and graft versus host disease (GVHD), and autoimmune diseases including SLE, Rheumatoid Arthritis, Multiple Sclerosis, and Inflammatory bowel disease.

In some embodiments, the methods of the invention result in genetically-modified human Breg cells expressing, not expressing, up-regulating or down-regulating the target antibody or antigen that may be useful, for example, for the enhancement or inhibition of Breg function and stability, for the programmed cell death of Breg, for Breg that are targeted to the site of function (e.g. to a donor organ following transplantation or to an inflamed joint in a subject having arthritis etc.).

In some embodiments, the methods of the invention may further comprise culturing the human $CD19^+$ B cells in the presence of one or more target antibodies or antigens, wherein the target antibody or antigen is associated with an immune-mediated disorder, and as according to the methods described above. Culturing the human $CD19^+$ B cells in the presence of one or more target antibodies or antigens would induce the Breg cells to take up and express the target antibody or antigen or a processed form of the target antibody or antigen. The resulting population of human Breg could then target antigen-specific effector (T) cells and antigen-specific regulatory (T) cells, in order to inhibit the immune response to that target antigen and thus treat the immune-mediated disorder in the subject. The target antibodies or antigens can be derived from human or other mammalian tissue, and can also be comprised of composite structures i.e. Synthetic Particulate Antigens, such as those derived by Thaunat et al (see, e.g., Sicard, A., et al., (2016) "B Cells Loaded with Synthetic Particulate Antigens: A Versatile Platform To Generate Antigen-Specific Helper T Cells for Cell Therapy". Nano Letters 16(1):297-308).

Culturing the human $CD19^+$ B cells in the presence of one or more target antibodies or antigens, wherein the target antibody or antigen is associated with an immune-mediated disorder, will result in a population of human Breg cells expressing the target antibody or antigen or a processed form of the target antibody or antigen. These human Breg cells may also be introduced into a subject having the immune-mediated disorder or condition and target antigen-specific effector (T) cells and antigen-specific regulatory (T) cells, in order to inhibit the immune response to that target antigen and thus treat the immune-mediated disorder or condition in the subject. Any immune-mediated disorder or condition could be treated using the populations of human Breg cells expressing the target antibody or antigen or a processed form of the target antibody or antigen. Examples of immune-mediated disorders or conditions that may be treated are transplantation, and GVHD, and autoimmune diseases including SLE, Rheumatoid Arthritis, Multiple Sclerosis, and Inflammatory bowel disease.

In some embodiments, the methods of the invention result in human Breg cells expressing the target antibody or antigen or a processed form of the target antibody or antigen that may be useful, for example, for the enhancement or inhibition of Breg function and stability, for the programmed cell death of Breg, for Breg that are targeted to the site of function (e.g. to a donor organ following transplantation or to an inflamed joint in a subject having arthritis etc.).

Any target antibody or antigen that is associated with an immune-mediated disorder could be used in any of the methods described herein specifying a target antibody or antigen. Examples of such target antigens include HLA for use following transplantation, citrullinated antigens for use where the subject to be treated has Rheumatoid Arthritis, double-stranded RNA (dsRNA) and single-stranded RNA (ssRNA) for use where the subject to be treated has SLE, and Myelin Oligodendrocyte Glycoprotein (MOG) for use where the subject to be treated has Multiple Sclerosis.

Pharmaceutical Compositions and Use in Treatments

The present invention also relates to pharmaceutical compositions comprising any of the isolated cell populations of the invention and any of the isolated cell populations produced by the methods of the invention.

The term "pharmaceutical composition" may be considered to refer to any composition capable of treating a disease or disorder, alleviating the symptoms of a disease or disorder, treating the underlying cause of a disease or disorder or curing the disease or disorder. The pharmaceutical compositions of the invention may comprise at least 40%, 50%, 55%, 60%, 65%, 70%, 75%, 80%, 85%, 90%, 95%, 96%, 97%, 98%, 99% or substantially 100% of the isolated cell populations of the invention or produced by the methods of the invention. The pharmaceutical compositions of the invention may comprise at least 1 million cells per kilogram weight of the intended recipient subject. Preferably, the pharmaceutical compositions of the invention may comprise 1-10 million cells/kg. Suitable numbers of cells per kilogram weight of the intended recipient subject could be easily determined by the skilled person.

The pharmaceutical compositions of the invention may further comprise a pharmaceutically acceptable carrier. Pharmaceutically acceptable carriers are suitable for in vivo administration to a subject. Examples of pharmaceutically acceptable carriers suitable for use in the compositions of the invention are well known to the skilled person but may include buffer solutions (e.g. phosphate), sugar or carbohydrate solutions (e.g. glucose or sucrose, sorbitol, or dextran), protein solutions (e.g. albumin or serum), cell culture liquids, cell media, culture media, media, gels, emulsions, DMSO, human serum albumin, oils or saline solutions. The pharmaceutical compositions of the invention may further comprise, for example, stabilizers, preservatives, diluents, emulsifiers and lubricants. Suitable additional components of the pharmaceutical compositions of the invention are well known to the skilled person.

In a preferred embodiment, the pharmaceutical compositions of the invention may comprise any of the isolated cell populations of the invention and/or any of the isolated cell populations produced by the methods of the invention; media (e.g., RPMI, RPMI-1640); human serum albumin and DMSO. In some embodiments the pharmaceutical compositions are frozen. Suitable amounts and ratios of each component may be readily determined by the skilled person according to standard protocols known in the art. Suitable methods for freezing the pharmaceutical compositions comprising the isolated cell populations of the invention would also be well-known to the skilled person.

The present invention also relates to the use of the pharmaceutical compositions of the invention, the isolated cell populations of the invention or the isolated cell populations produced by the methods of the invention, as described herein, in modulating the immune response in an individual in need thereof or in the treatment of an immune-mediated disorder or condition, or in the prevention of an immune-mediated disorder or condition.

The pharmaceutical compositions of the invention, the isolated cell populations of the invention or the isolated cell populations produced by the methods of the invention, as described herein, may be administered to an individual in need thereof at a concentration of at least 1 million cells per kilogram weight of the individual, preferably, at a concentration of 1-10 million cells/kg.

The isolated human Breg cell population or pharmaceutical compositions comprising this cell population may be used in a method of treating or preventing development of an immune-mediated disorder or condition, wherein the method comprises administering the isolated human Breg cell population or pharmaceutical compositions comprising this cell population to a second subject in need thereof. In some embodiments the first subject is the second subject in need thereof. In some embodiments the first subject is a donor, optionally a healthy donor, and the second subject is the recipient. In some embodiments the donor is histocompatible with the recipient. Optionally, the human CD19$^+$ B cells isolated from the first subject are genetically modified prior to expansion, thus the resulting human Breg cells administered to the second subject are genetically modified. The pharmaceutical compositions of the invention may be administered at a concentration of at least 1 million cells per kilogram weight of the intended recipient. Preferably, the pharmaceutical compositions of the invention may be administered at a concentration of 1-10 million cells/kg. Suitable concentrations could be easily determined by the skilled person. In some embodiments the human CD19$^+$ B cells isolated from the first subject are stored for future use. Alternatively, the isolated human Breg cell population produced according to the methods of the invention may be stored for future use. The pharmaceutical compositions of the invention may also be suitable for storage for future use. In some embodiments, storage may include freezing of the isolated cell populations or pharmaceutical compositions.

Examples of immune-mediated disorders or conditions that may be treated using the pharmaceutical compositions or the isolated cell populations of the invention are autoimmune disorders, allergic disorders and inflammatory disorders. The term "autoimmune disorder" may be considered to refer to a condition wherein the immune-system of a subject reacts to and attacks the subjects own cells, tissues and/or organs causing damage and/or injury. The term "inflammatory disorder" may be considered to refer to a condition wherein uncontrolled or inappropriate inflammation occurs in a subject causing damage to healthy cells, tissues and/or organs (e.g. chronic inflammation). The term "allergic disorder" may be considered to refer to a condition resulting from hypersensitivity of the immune system to something in the environment that usually causes little or no problem in most people. Such allergic disorders may include hay fever, food allergies, atopic dermatitis, allergic asthma, and anaphylaxis.

Examples of such disorders or conditions include psoriasis, allergic contact dermatitis, inflammatory bowel disease, multiple sclerosis, type I diabetes, rheumatoid arthritis, Graves' disease and thyroiditis, scleroderma/systemic sclerosis, vitiligo, and systemic lupus erythematosus, allergic reactions to drugs, alopecia greata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid and associated skin diseases, cardiomyopathy, Celiac disease, Celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, cutaneous necrotizing venulitis, discoid lupus, erythema multiforme, essential mixed cryoglobulinemia, fibromyalgia-fibromyositis, glomerulonephritis, Guillain-Barre, graft versus host disease (GVHD), Hashimoto's thyroiditis, idiopathic pulmonary fibrosis, idiopathic/autoimmune thrombocytopenia purpura (ITP), immunologic lung disease, immunologic renal disease, IgA neuropathy, juvenile arthritis, lichen planus, lupus erthematosus, Meniere's disease, mixed connective tissue disease, multiple sclerosis, type 1 or immune-mediated diabetes mellitus, myasthenia gravis, pemphigus-related disorders (e.g., pemphigus vulgaris), pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, rheumatic fever, sarcoidosis, scleroderma, Sjögren's syndrome, stiff-man syndrome, spondyloarthropathies, lupus erythematosus, systemic vasculitis, takayasu arteritis, temporal arteristis/giant cell arteritis, thrombocytopenia, thyroiditis, ulcerative colitis, uveitis, vasculitides such as dermatitis herpetiformis vasculitis, vitiligo, and Wegener's granulomatosis. In some preferred embodiments, the pharmaceutical compositions or the isolated cell populations of the invention are for use in the treatment or prevention of Crohn's disease, Ulcerative Colitis, Rheumatoid Arthritis, Systemic Lupus Erythematosus (SLE), Multiple Sclerosis, Type 1 Diabetes, Atherosclerosis, Asthma and Allergy.

In particular, use of the pharmaceutical compositions or the isolated cell populations of the invention in the treatment or prevention of immune-mediated disorders or conditions, wherein the immune-mediated disorder or conditions is selected from transplant rejection, autoimmune disorders, graft versus host disease (GVHD), allergic disease and inflammatory disorders are contemplated.

The pharmaceutical compositions or isolated cell populations of the present invention may be administered by any suitable means, which could be easily identified by a person skilled in the art. Suitable means for administration include intraperitoneal, parenteral, intravenous, intramuscular, subcutaneous, transdermal, transmucosal, oral, nasal, per rectum, enteral or intrathecal. Preferably, the pharmaceutical compositions of the present invention may be formulated as an injectable formulation.

Suitable dosages and dosage regimens can be determined by standard clinical methods known to those of skill in the art and will generally be a therapeutically effective dose. The term "therapeutically effective dose" may be considered to refer to a dose or amount of cells that produces a therapeutic response or desired effect in some fraction of the subjects taking it, but does not result in an intolerable toxic effect. The pharmaceutical compositions or isolated cell populations may be administered, for example, at least every 2, 4, 6, 8, 10, 12 hours, at least every 2, 4, 6, 8, 10 days or at least twice a month.

In some embodiments, the pharmaceutical compositions or isolated cell populations may be administered or used in combination with other treatments. Preferably, the other treatment is an immunosuppressant. The immunosuppressant may be selected from an MTOR inhibitor, a calcineurin inhibitor, an interleukin inhibitor, a chemokine inhibitor, an antibody, a chemokine, an interleukin, a chemotherapeutic, a steroid, irradiation, or another cellular therapy. The other treatments may be administered concurrently with the pharmaceutical compositions or isolated cell populations of the invention. For example they may be administered in one composition or multiple compositions may be administered at the same time. In some embodiments the treatments may be administered one after the other in any order.

Methods of Diagnosis

The present invention also relates to methods for assessing Breg cell function in a subject. Methods for assessing Breg cell function are also suitable for diagnosing or predicting the likelihood of a patient developing an autoimmune, inflammatory and allergic disease or condition (such as those described herein) and transplantation rejection.

Thus, in some embodiments, a method of assessing Breg cell function in a subject is contemplated, the method comprising:
  quantifying the number and/or percentage of human B cells having a phenotype of $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-VCD154^+$, in a sample obtained from the subject; and
  comparing the number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample to the number of human B cells having said phenotype in a control;
wherein a significantly larger number and/or percentage of human Breg cells having the phenotype $CD73^-CD71^+CD25^+$ and/or $TIM-1^+CD154^+$; preferably $CD73^-CD71^+CD25^+CD154^+$, or $CD73^-CD71^+CD25^+TIM-1^+$; most preferably $CD73^-CD71^+CD25^+TIM-1^+CD154^+$, in the subject sample compared to the control indicates Breg cell function in the subject.

As will be appreciated, human B cells are typically $CD19^+$ and in all of the aspects of the invention described herein, CD19 may also be detected. CD19 may be detected in addition to the other markers described herein as a marker of the Breg cell population or $CD19^+$ may be used as a marker in the initial isolation of the B cells from a subject.

The number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample may be less than, the same as or larger than the number of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the control. Wherein, the same or a greater, higher or larger number and/or percentage of human Breg cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample, compared to the control, indicates Breg cell function in the subject. A larger number and/or percentage may be considered to refer to a significantly larger, greater or higher number and/or percentage. Wherein, a smaller, lower or reduced number and/or percentage of human Breg cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample, compared to the control, indicates no, poor, lowered or reduced Breg cell function in the subject. A smaller number and/or percentage may be considered to refer to a significantly smaller, lower or reduced number and/or percentage. For example, the number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample may be at least 1.5, 2, 3, 4, 5, 6, 7, 8, 9, 10, 15, 20, 30, 40, 50, 100, 150, 200 fold larger or smaller than the number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the control. Preferably, the number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample is 2-5 fold higher or lower than the number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the control. Most preferably, the number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample is 2-5 fold lower than the number and/or percentage of human B cells having said phenotype in the control; such a difference is indicative of lowered Breg cell function in the subject. A reduced, lowered or decreased number and/or percentage of human B cells having the phenotype $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the subject sample compared to the control may diagnose, or predict an increased likelihood of a subject developing, an autoimmune, inflammatory or allergic disease or condition (such as those described herein), or an allogenic reaction (such as rejection of a transplant). The absence of Breg cell function, or reduced, lowered or decreased Breg cell function in the subject may diagnose, or predict an increased likelihood of a subject developing, an autoimmune, inflammatory or allergic disease or condition (such as those described herein), or an allogenic reaction (such as rejection of a transplant).

In some cases, patients having an autoimmune, inflammatory or allergic condition may have the same levels of $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, Breg as compared to a healthy control, but the Breg in the patient having the autoimmune, inflammatory or allergic condition are poorly functional or non-functional. In some embodiments, the present invention also relates to the use of the culture methods of the invention for assessing Breg cell function in a subject. Thus, in some embodiments, a method of assessing Breg cell function in a subject is contemplated, the method comprising:
  isolating human $CD19^+$ B cells from the subject;
  culturing said $CD19^+$ B cells in the presence of a CD40 agonist and at least one cytokine or growth factor for at least 3 days;
  determining the phenotype and/or function of the Breg cells so produced;
wherein a phenotype of $CD73^-CD71^+CD25^+$ and/or $TIM-1^+CD154^+$; preferably $CD73^-CD71^+CD25^+CD154^+$ or $CD73^-CD71^+CD25^+TIM-1^+$; most preferably $CD73^-$ CD71$^+$CD25$^+$TIM-1$^+$CD154$^+$, indicates Breg cell function in the subject. Optionally wherein the method further comprises the step of:

measuring the function of the Breg cells having the phenotype CD73$^-$CD71$^+$CD25$^+$ and/or TIM-1$^+$ CD154$^+$; preferably CD73$^-$CD71$^+$CD25$^+$CD154$^+$ or CD73$^-$CD71$^+$CD25$^+$TIM-1$^+$; most preferably CD73$^-$CD71$^+$CD25$^+$TIM-1$^+$CD154$^+$, so produced.

In some embodiments, an alternative method of assessing Breg cell function in a subject is contemplated, the method comprising:

isolating human CD73$^-$CD71$^+$CD25$^+$ and/or TIM-1$^+$ CD154$^+$; preferably CD73$^-$CD71$^+$CD25$^+$CD154$^+$ or CD73$^-$CD71$^+$CD25$^+$TIM-1$^+$; most preferably CD73$^-$CD71$^+$CD25$^+$TIM-1$^+$CD154$^+$, Breg cells from the subject;

measuring the function of the Breg cells so isolated.

The absence of Breg cell function, or lowered or reduced Breg cell function, in the subject may diagnose, or predict an increased likelihood of a subject developing, an autoimmune, inflammatory and allergic disease or condition (such as those described herein), or transplantation rejection.

In any of the methods described herein, the function of the Breg cells produced or isolated in the described methods may be determined by any suitable method known in the art, examples of such methods include detecting intracellular markers of function, such as the expression of pSTAT3 in response to relevant stimulators; and testing the in vitro suppression of effector T cells, or other immune cells, by the Breg so produced. Similarly, the regulatory function of the isolated populations of human Breg cells described herein may also be so tested. The function of the Breg produced or isolated by the methods described herein may also be determined by testing for function in vivo, e.g., in suitable animal models. The skilled person would be capable of selecting such suitable animal models. TIM-1 has been shown by the present inventors to regulate STAT3 phosphorylation in TIM-1$^+$ Breg cells, thereby controlling Breg function. Thus, Breg function may be determined by assaying levels of STAT3 phosphorylation. Increased STAT3 phosphorylation indicates TIM-1 expression and increased Breg function.

The present invention also provides methods for (a) monitoring the progression or regression of a disease in a subject; (b) monitoring the response of a subject to a treatment (e.g., monitoring a subject's response to immunotherapy); or (c) monitoring transplant rejection or the status of a transplant in a subject. The present invention provides a method for monitoring the progression or regression of a disease in a subject, the method comprising:

isolating a first sample of human CD19$^+$ B cells from the subject;

culturing said CD19$^+$ B cells in the presence of a CD40 agonist and at least one cytokine or growth factor for at least 3 days;

determining the phenotype and/or function of the Breg cells so produced;

isolating a second sample of human CD19$^+$ B cells from the subject;

culturing said CD19$^+$ B cells in the presence of a CD40 agonist and at least one cytokine or growth factor for at least 3 days;

determining the phenotype and/or function of the Breg cells so produced;

comparing the phenotype and/or function of the Breg cells produced from the first sample of human CD19$^+$ B cells isolated from the subject with the phenotype and/or function of the Breg cells produced from the second sample of human CD19$^-$ B cells isolated from the subject;

wherein an increase in the number and/or percentage of Breg cells having a phenotype of CD73$^-$CD71$^+$CD25$^-$ and/or TIM-1$^+$; CD154$^+$; preferably CD73$^+$CD71$^+$CD25$^+$CD154$^+$ or CD73$^-$CD71$^+$CD25$^-$TIM-1$^+$; most preferably CD73$^-$CD71$^+$CD25$^+$TIM-1$^+$CD154$^+$, or an increase in the Breg cell function indicates a regression of the disease in the subject.

The second sample may be taken at least 1, 2, 3, 4, 5, 10, 15, 20, 30, 40 or 50 weeks or at least 1, 2, 3, 4, 5, 10 or 20 years after the first sample. The disease or condition may be the rejection of a transplant, graft versus host disease (GVHD), autoimmune, inflammatory or allergic diseases or conditions.

The present invention also provides a method for monitoring a subject's response to a treatment, the method comprising:

isolating human CD19$^+$ B cells from the subject prior to treatment;

culturing said CD19$^+$ B cells in the presence of a CD40 agonist and at least one cytokine or growth factor for at least 3 days;

determining the phenotype and/or function of the Breg cells so produced;

isolating human CD19$^+$ B cells from the subject after treatment;

culturing said CD19$^+$ B cells in the presence of a CD40 agonist and at least one cytokine or growth factor for at least 3 days;

determining the phenotype and/or function of the Breg cells so produced;

comparing the phenotype and/or function of the Breg cells produced from the human CD19$^-$ B cells isolated from the subject before treatment with the phenotype and/or function of the Breg cells produced from the human CD19$^-$ B cells isolated from the subject after treatment;

wherein an increase in the number and/or percentage of Breg cells having a phenotype of CD73$^-$CD71$^+$CD25$^+$ and/or TIM-1$^+$CD154$^+$; preferably CD73$^-$CD71$^+$CD25$^+$CD154$^+$ or CD73$^-$CD71$^+$CD25$^+$TIM-1$^+$; most preferably CD73$^-$CD71$^+$CD25$^+$TIM-1$^+$CD154$^+$, or an increase in the Breg cell function indicates a positive response to the treatment in the subject.

In some embodiments, the treatment may be treating transplantation, GVHD, autoimmune, inflammatory or allergic diseases or conditions. In a preferred embodiment, the treatment is immunotherapy. The above described methods may also be applied to monitoring the response of a subject to a transplant, i.e. to monitor for transplant tolerance or rejection.

Any of the methods for expanding a Breg cell population described herein are suitable for use in the methods for assessing Breg cell function in a subject; the methods for monitoring the progression or regression of a disease in a subject; the methods for monitoring a subject's response to a treatment or the methods for monitoring the response of a subject to a transplant (i.e. to monitor for transplant tolerance or rejection); and therefore, any of the variations upon the culture methods described herein may be applied to any of these methods.

Methods of Diagnosis of Cancer and Infection

The present invention also relates to a method of diagnosing cancer in a patient, monitoring cancer in a patient, or predicting the likelihood of a patient developing cancer; or a method of diagnosing an infection (e.g., at the site of transplantation, or in a patient having undergone transplantation), monitoring infection in a patient, or predicting the likelihood of a patient developing infection; wherein the method comprises:

quantifying the number and/or percentage of human B cells, having a phenotype $CD73^-CD25^+CD71^+$ in a patient sample; and comparing the number and/or percentage of human B cells having the phenotype $CD73^-CD25^+CD71^+$ in the patient sample to the number and/or percentage of human B cells having the phenotype $CD73^-CD25^+CD71^+$ in a control;

wherein a larger number and/or percentage of human B cells having the phenotype $CD73^-CD25^+CD71^+$ in the patient sample compared to the control indicates the patient has cancer, or has a more aggressive or advanced cancer, or is more likely to develop cancer; or indicates the patient has an infection, or has a more aggressive or advanced infection, or is more likely to develop an infection.

Optionally wherein the method further comprises measuring the function of the Breg cells having the phenotype $CD73^-CD25^+CD71^+$ in the patient sample and comparing the function of the Breg cells having the phenotype $CD73^-CD25^+CD71^+$ in the patient sample to the function of the Breg cells having the phenotype $CD73^{-1\ CD}25^+CD71^+$ in the control. Wherein, increased function of the Breg cells having the phenotype $CD73^-CD25^+CD71^+$ in the patient sample compared to the control indicates the patient has cancer, or has a more aggressive or advanced cancer, or is more likely to develop cancer; or indicates the patient has an infection, or has a more aggressive or advanced infection, or is more likely to develop an infection.

In some embodiments the present invention also provides a method of diagnosing cancer in a patient, monitoring cancer in a patient, or predicting the likelihood of a patient developing cancer; or a method of diagnosing an infection, monitoring infection in a patient, or predicting the likelihood of a patient developing infection, wherein the method comprises:

quantifying the number and/or percentage of human B cells, having a phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in a patient sample; and comparing the number and/or percentage of human B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the patient sample to the number and/or percentage of human B cells having the phenotype $CD73^-CD71^+CD25^+$ or $TIM-1^+\ CD154^+$; preferably $CD73^-CD71^+CD25^+CD154^+$ or $CD73^-CD71^+CD25^+\ TIM-1^+$; most preferably $CD73^-CD71^+CD25^+TIM-1^+CD154^+$, in a control;

wherein a larger number and/or percentage of human B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the patient sample compared to the control indicates the patient has cancer, or has a more aggressive or advanced cancer, or is more likely to develop cancer; or indicates the patient has an infection, or has a more aggressive or advanced infection, or is more likely to develop an infection.

Optionally wherein the method further comprises measuring the function of the Breg cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the patient sample and comparing the function of the Breg cells having said phenotype in the patient sample to the function of the Breg cells having said phenotype in the control. Wherein, increased function of the Breg cells having said phenotype in the patient sample compared to the control indicates the patient has cancer, or has a more aggressive or advanced cancer, or is more likely to develop cancer; or indicates the patient has an infection, or has a more aggressive or advanced infection, or is more likely to develop an infection.

In some embodiments the present invention also provides a method of diagnosing cancer in a patient, monitoring cancer in a patient, or predicting the likelihood of a patient developing cancer; or a method of diagnosing an infection, monitoring infection in a patient, or predicting the likelihood of a patient developing infection, wherein the method comprises:

quantifying the number and/or percentage of human B cells, having a phenotype $TIM-1^+CD154^+$ in a patient sample; and comparing the number and/or percentage of human B cells having the phenotype $TIM-1^+CD154^+$ in the patient sample to the number and/or percentage of human B cells having the phenotype $TIM-1^+\ CD154^+$ in a control;

wherein a larger number and/or percentage of human B cells having the phenotype $TIM-1^+CD154^+$ in the patient sample compared to the control indicates the patient has cancer, or has a more aggressive or advanced cancer, or is more likely to develop cancer; or indicates the patient has an infection, or has a more aggressive or advanced infection, or is more likely to develop an infection.

Optionally wherein the method further comprises measuring the function of the Breg cells having the phenotype $TIM-1^+CD154^+$, in the patient sample and comparing the function of the Breg cells having said phenotype in the patient sample to the function of the Breg cells having said phenotype in the control. Wherein, increased function of the Breg cells having said phenotype in the patient sample compared to the control indicates the patient has cancer, or has a more aggressive or advanced cancer, or is more likely to develop cancer; or indicates the patient has an infection, or has a more aggressive or advanced infection, or is more likely to develop an infection.

The number and/or percentage of human B cells having the phenotype $CD73^-CD25^+CD71^+$, $TIM-1^+CD154^+$, $CD73^-CD25^+CD71^+TIM-1^+$, $CD73^-CD25^+CD71^+CD154^+$, or $CD73^-CD25^+CD71^+TIM-1^+CD154^+$, in the patient sample may be less than, the same as or larger than the number and/or percentage of human B cells having the phenotype $CD73^-CD25^+CD71^+$, $TIM-1^+CD154^+$, $CD73^-CD25^+CD71^+TIM-1^+$, $CD73^-CD25^+CD71^+CD154^+$, or $CD73^-CD25^+CD71^+TIM-1^+CD154^+$, in the control. Wherein, a greater, higher or larger number and/or percentage of human B cells having the phenotype $CD73^-CD25^+CD71^+$, $TIM-1^+CD154^+$, $CD73^-CD25^+CD71^+TIM-1^+$, $CD73^-CD25^+CD71^+CD154^+$, or $CD73^-CD25^+CD71^+TIM-1^+CD154^+$, in the patient sample, compared to the control, indicates the patient has cancer, or has a more aggressive or advanced cancer, or is more likely to develop cancer; or indicates the patient has an infection, or has a more aggressive or advanced infection, or is more likely to develop an infection. A larger number and/or percentage may be considered to refer to a significantly larger, greater or higher number and/or percentage. For example, in some embodiments, the number and/or percentage of human B cells having the phenotype $CD73^-CD25^+CD71^+$ in the patient sample may be at least 1.5, 2, 3, 4, 5, 6, 7, 8, 9, 10, 15, 20, 30, 40, 50, 100, 150, 200 fold larger than the number and/or percentage of human B cells having the phenotype $CD73^-CD25^+CD71^+$ in the control. In some embodiments, the number and/or percentage of human B cells having the phenotype $TIM-1^+CD154^+$ in the patient sample may be at least 1.5, 2, 3, 4, 5, 6, 7, 8, 9, 10, 15, 20, 30, 40, 50, 100, 150, 200 fold larger than the number and/or percentage of human B cells having the phenotype $TIM-1^+CD154^+$ in the control. In some embodiments, the number and/or percentage of human B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the patient sample may be at least 1.5, 2, 3, 4, 5, 6, 7, 8, 9, 10, 15, 20, 30, 40, 50, 100, 150, 200 fold larger than the number and/or percentage of human B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the control. Preferably, the number and/or percentage of human B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in the patient sample is 2-5 fold higher than the number and/or percentage of human B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, respectively, in the control. Such a difference is indicative of cancer (e.g. SCC) in the patient, or a more aggressive or advanced cancer in the patient, or an increased likelihood that the patient will develop cancer; or is indicative of infection in the patient, or a more aggressive or advanced infection in the patient, or an increased likelihood that the patient will develop an infection.

Thus, in some embodiments the presence of human B cells having a phenotype of $CD73^-CD71^+CD25^+$ or $TIM-1^+CD154^+$; preferably $CD73^-CD71^+CD25^+CD154^+$ or $CD73^+CD71^+CD25^+TIM-1^+$; most preferably $CD73^-CD71^+CD25^+TIM-1^+CD154^+$, in a patient sample, indicates that the patient has cancer, or has a more aggressive or advanced cancer, or is more likely to develop cancer or a more aggressive or advanced cancer, when compared to a control. Alternatively, the presence of human B cells having a phenotype of $TIM-1^-CD154^-$; preferably $CD73^-CD71^+CD25^+CD154^-$ or $CD73^-CD71^+CD25^+TIM-1^-$; most preferably $CD73^-CD71^+CD25^+TIM-1^-CD154^-$, in a patient sample, indicates that the patient does not have cancer, or has a less aggressive or less advanced cancer, or is less likely to develop cancer or a more aggressive or advanced cancer, compared to a control.

Similarly, in some embodiments the presence of human B cells having a phenotype of $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in a patient sample, indicates that the patient has an infection, or has a more aggressive or advanced infection, or is more likely to develop an infection or a more aggressive or advanced infection, when compared to a control. Alternatively, the presence of human B cells having a phenotype of $TIM-1^-CD154^-$; preferably $CD73^-CD71^-CD25^+CD154^-$ or $CD73^-CD71^+CD25^-TIM-1^-$; most preferably $CD73^-CD71^+CD25^+TIM-1^-CD154^-$, in a patient sample, indicates that the patient does not have an infection, or has a less aggressive or less advanced infection, or is less likely to develop an infection or a more aggressive or advanced infection, compared to a control.

In any of the methods described herein relating to cancer, the cancer may be any type of cancer, in particular squamous cell carcinoma of the skin (SCC), biliary cancer, ovarian cancer, gastric cancer, lung cancer, colorectal cancer, pancreatic cancer, breast cancer, oesophageal cancer, bladder cancer, cervical squamous cell carcinoma and hepatocellular carcinoma, as well as lymphoma and leukaemia. In some preferred embodiments the cancer is SCC.

In any of the methods described herein relating to infection, the infection may be any type of infection, in particular infection at the site of transplantation, or in a patient having undergone transplantation, viral infections (e.g., HIV) and bacterial infections (e.g., Salmonella). In some preferred embodiments the infection is a viral infection (e.g., HIV) or a bacterial infection (e.g., Salmonella).

The patient sample may comprise blood, cells, tissue, lymph node tissue, PBMCs, tumour, urine, sputum, cerebrospinal fluid, skin, synovial fluid. The sample may be taken from a patient suspected of having cancer, preferably a patient suspected of having SCC. The sample may be taken from a patient suspected of having an infection, preferably a patient suspected of having an infection at the site of transplantation. Methods for obtaining such samples from a patient are well known in the art and any suitable means may be utilised. The number and/or percentage of cells having the phenotype may be determined by suitable methods known to the person skilled person in the art. Such methods include labelling of cell-surface markers (e.g. CD73, CD25, CD71, TIM-1, CD154, and/or CD19) using fluorochrome-conjugated antibodies followed by flow cytometry analysis. The control may be a control sample. Optionally, the control sample comprises blood, cells, tissue, lymph node tissue, PBMCs, tumour, urine, sputum, cerebrospinal fluid, skin, synovial fluid. The control sample may be taken from a healthy subject, or a subject not having cancer, or a subject having cancer, preferably a less aggressive or advanced cancer. Alternatively, the control sample may be taken from a healthy subject, or a subject not having an infection, or a subject having an infection, preferably a less aggressive or advanced infection.

The number and/or percentage of human B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$, in a control may be a pre-set value. The pre-set value may have been determined by analysing at least one sample(s) taken from at least one healthy subject(s), or subject(s) not having cancer/infection, or subject(s) having cancer/infection, preferably a less aggressive or advanced cancer/infection, and determining the average number and/or percentage of human B cells having the phenotype in the at least one sample(s) taken from the at least one healthy subject(s) or subject(s) not having cancer/infection or subject(s) having cancer/infection, preferably a less aggressive or advanced cancer/infection.

Compounds for Use in Treating Cancer and Infection

The present invention also relates to methods for treating cancer and/or infection and compounds for use in such methods. Further, the invention relates to pharmaceutical compositions comprising said compounds.

In some embodiments, the invention provides a compound for use in the treatment of cancer or infection. Such compounds are useful in treating cancer or infection by inhibiting the suppressive function of a Breg cell population. Typically, the Breg cells have the phenotype $CD73^-CD71^+CD25^+$ or $TIM-1^+CD154^+$; preferably $CD73^-CD71^+CD25^+CD154^+$ or $CD73^-CD71^-CD25^-TIM-1^+$; most preferably $CD73^-CD71^+CD25^+TIM-1^+CD154^-$. In preferred embodiments the compounds useful in the treatment of cancer or infection are antibodies. Such antibodies bind to an antigen on the surface of the Breg cells and thereby inhibit the suppressive function of the Breg cells. Such antibodies bind to an antigen on the surface of the Breg cells and inhibit binding between the target antigen and its ligand. In some preferred embodiments the compounds useful in the treatment of cancer or infection are bispecific, tri-specific or multi-specific antibodies.

In some embodiments the present invention provides an antibody that binds to TIM-1 on the surface of Breg cells for use in the treatment of cancer. In some embodiments the present invention provides an antibody that binds to TIM-1 on the surface of Breg cells for use in the treatment of infection. The antibody binds to TIM-1 and inhibits binding of TIM-1 to its ligand (for example, TIM-4, or phosphatidyl serine). The anti-TIM-1 antibody (i.e. an antibody that binds to TIM-1) is useful in the treatment of cancer or infection by inhibiting the suppressive function of the Breg cell population.

In some embodiments the present invention provides an antibody that binds to IL-10R on the surface of Breg cells for use in the treatment of cancer. In some embodiments the present invention provides an antibody that binds to IL-10R on the surface of Breg cells for use in the treatment of infection. The antibody binds to IL-10R and inhibits binding of IL-10R to its ligand (e.g. IL-10). The anti-IL-10R antibody (i.e. an antibody that binds to IL-10R) is useful in the treatment of cancer or infection by inhibiting the suppressive function of the Breg cell population.

In some embodiments the present invention provides an antibody that binds to CD154 on the surface of Breg cells for use in the treatment of cancer. In some embodiments the present invention provides an antibody that binds to CD154 on the surface of Breg cells for use in the treatment of infection. The antibody binds to CD154 and inhibits binding of CD154 to its ligand (e.g. CD40, $\alpha5\beta1$ integrin or $\alpha IIb\beta3$). The anti-CD154 antibody (i.e. an antibody that binds to CD154) is useful in the treatment of cancer or infection by inhibiting the suppressive function of the Breg cell population.

In some embodiments the present invention provides an antibody that binds to CD40 on the surface of B cells for use in the treatment of cancer. In some embodiments the present invention provides an antibody that binds to CD40 on the surface of B cells for use in the treatment of infection. The antibody binds to CD40 and inhibits binding of CD40 to its ligand (e.g. CD154, CD40L, TRAF1, TRAF2, TRAF6, or TRAF5). The anti-CD40 antibody (i.e. an antibody that binds to CD40) is useful in the treatment of cancer or infection by inhibiting the suppressive function of the Breg cell population.

In some embodiments the present invention provides a bispecific antibody that binds to TIM-1 and CD154, TIM-1 and CD20, CD154 and CD20, TIM-1 and CD19 or CD154 and CD19, preferably TIM-1 and CD154, TIM-1 and CD20 or CD154 and CD20, most preferably TIM-1 and CD154, on the surface of Breg cells for use in the treatment of cancer. In some embodiments the present invention provides a bispecific antibody that binds to TIM-1 and CD154, TIM-1 and CD20, CD154 and CD20, TIM-1 and CD19 or CD154 and CD19, preferably TIM-1 and CD154, TIM-1 and CD20 or CD154 and CD20, most preferably TIM-1 and CD154, on the surface of Breg cells for use in the treatment of infection. The antibody binds to TIM-1 and CD154, TIM-1 and CD20, CD154 and CD20, TIM-1 and CD19 or CD154 and CD19, preferably TIM-1 and CD154, TIM-1 and CD20 or CD154 and CD20, most preferably TIM-1 and CD154, and inhibits binding of TIM-1 and CD154, TIM-1 and CD20, CD154 and CD20, TIM-1 and CD19 or CD154 and CD19, preferably TIM-1 and CD154, TIM-1 and CD20 or CD154 and CD20, most preferably TIM-1 and CD154, to their respective ligands. Such bispecific antibodies may be useful in the treatment of cancer or infection by inhibiting the suppressive function of the Breg cell population.

In some embodiments the present invention provides a tri-specific antibody that binds to TIM-1, CD154 and CD20 or TIM-1, CD154 and CD19, preferably TIM-1, CD154 and CD20 on the surface of Breg cells for use in the treatment of cancer. In some embodiments the present invention provides a tri-specific antibody that binds to TIM-1, CD154 and CD20 or TIM-1, CD154 and CD19, preferably TIM-1, CD154 and CD20, on the surface of Breg cells for use in the treatment of infection. The antibody binds to TIM-1, CD154 and CD20 or TIM-1, CD154 and CD19, preferably TIM-1, CD154 and CD20, and inhibits binding of TIM-1, CD154 and CD20 or TIM-1, CD154 and CD19, preferably TIM-1, CD154 and CD20, to their respective ligands. Such tri-specific antibodies may be useful in the treatment of cancer or infection by inhibiting the suppressive function of the Breg cell population.

In some embodiments any one of the antibodies of the invention in combination with an antibody that binds to any one of CD25, CD71, CD39, CD122, and B7-H4 may be useful in the treatment of cancer or infection. In some embodiments, provided is a plurality of antibodies, wherein each antibody binds to a target selected from TIM-1, IL-10R, CD154, CD20, CD19, CD40, CD25, CD71, CD39, CD122, and B7-H4, for use in the treatment of cancer or infection. In some embodiments, provided is a multi-specific antibody or antigen-binding fragment thereof that binds to TIM-1 and/or CD154 and any one of CD20, CD19, IL-10R, CD40, CD25, CD71, CD39, CD122 or B7-H4, or combinations thereof, on the surface of Breg cells for use in the treatment of cancer or infection. A combination of antibodies, targeting TIM-1, IL-10R CD154, CD20, CD19 and/or CD40 and CD25, CD71, CD39, CD122, and/or B7-H4 (a variety of other regulatory B cell targets) would specifically target the Breg cell population and inhibit the suppressive function of the Breg cell population. Similarly, a bispecific, tri-specific or multi-specific antibody targeting any of TIM-1, CD154 and/or CD20 or CD19, and/or any of CD20, CD19, IL-10R, CD40, CD25, CD71, CD39, CD122 and/or B7-H4 would specifically target the Breg cell population and inhibit the suppressive function of the Breg cell population.

Furthermore, the present inventors have shown that TIM-1 controls the phosphorylation of STAT3 in TIM-1$^+$ Breg, and in doing so, controls Breg function. Blockade of TIM-1 results in decreased STAT3 phosphorylation, which results in reduced Breg suppressive function. Thus, reagents to inhibit STAT3 phosphorylation may be used in the treatment of cancer or infection. Similarly, reagents to enhance STAT3 phosphorylation may enhance the suppressive function of Bregs. Thus, reagents to enhance STAT3 phosphorylation may be useful in the treatment of transplant rejection, GVHD, autoimmune, inflammatory or allergic diseases or conditions.

In accordance with all of the aspects of the present invention, the Breg cell population of any of the aspects described herein is characterised in that the B cells have the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$.

In preferred embodiments, the cancer or infection is characterised by the presence of B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$ and/or where the B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$ have suppressive function. In some embodiments, the cancer or infection is characterised in that the number and/or percentage of B cells in the patient having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$ is increased in comparison to a control. Suitable methods for identifying such cancers or infections are described herein, for example the methods for diagnosing cancer or infection in a patient sample may be applied to determining cancers or infections suitable for treatment using the antibodies of the invention.

B cells isolated from a patient having cancer may be tested for their suppressive function by any suitable method known in the art, examples of such methods include detecting intracellular markers of function, such as the expression of pSTAT3 in response to relevant stimulators; and testing the in vitro suppression of effector T cells, or other immune cells, by the B cells. The function of the isolated B cells may be determined by testing for function in suitable animal models. The skilled person would be capable of selecting such suitable animal models.

In some embodiments, the antibodies of the invention may be used in treating cancer, wherein the cancer may be any type of cancer, in particular SCC, biliary cancer, ovarian cancer, gastric cancer, lung cancer, colorectal cancer, pancreatic cancer, breast cancer, oesophageal cancer, bladder cancer, cervical squamous cell carcinoma and hepatocellular carcinoma, as well as lymphoma and leukaemia. In some preferred embodiments the cancer is SCC.

In some embodiments, the antibodies of the invention may be used in treating infection, the infection may be any type of infection, in particular infection at the site of transplantation, or in a patient having undergone transplantation, viral infections (e.g., HIV) and bacterial infections (e.g., Salmonella). In some preferred embodiments the infection is a viral infection (e.g., HIV) or a bacterial infection (e.g., Salmonella).

The term "antibody" as referred to herein includes whole, intact antibodies and any antigen binding fragment thereof (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

An antibody may be a polyclonal antibody or a monoclonal antibody. The antibody may be produced by any suitable method. For example suitable methods for producing monoclonal antibodies are disclosed in "Monoclonal Antibodies; A manual of techniques", H Zola (CRC Press, 1988) and in "Monoclonal Hybridoma Antibodies: Techniques and Application", SGR Hurrell (CRC Press, 1982). Recombinant techniques may also be used.

The term "antigen-binding fragment" of an antibody refers to one or more fragments of an antibody that retain the ability to specifically bind to an antigen, such as TIM-1, IL-10R, CD154, CD20, CD19 or CD40. It has been shown that the antigen-binding function of an antibody can be performed by fragments of a full-length antibody. Examples of binding fragments encompassed within the term "antigen-binding fragment" of an antibody include a Fab fragment, a F(ab')$_2$ fragment, a Fab' fragment, a Fd fragment, a Fv fragment, a Fc fragment, a dAb fragment and an isolated complementarity determining region (CDR). These antigen binding fragments can be incorporated into single domain antibodies (e.g., nanobodies), single-chain antibodies, maxibodies, minibodies, intrabodies, diabodies, triabodies, tetrabodies, v-NAR and bis-scFv (see, e.g., Hollinger and Hudson, *Nature Biotechnology*, 23(9): 1126-1136 (2005)). Single chain antibodies such as scFv and heavy chain antibodies such as VHH and camel antibodies are also intended to be encompassed within the term "antigen-binding fragment" of an antibody. These antibody fragments may be obtained using conventional techniques known to those of skill in the art, and the fragments may be screened for utility in the same manner as intact antibodies.

The antibody may be any class of antibody such as IgG, IgM, IgA, IgD or IgE, particularly IgM or an IgG antibody, but in a preferred instance the antibody is an IgM antibody. The antibody may be, in some instance, an IgG1, IgG2, IgG3, or IgG4 class antibody. It will be appreciated by the skilled person that an antibody of one class can be converted to that of another by changing the constant regions to those of the desired antibody class.

Another form of an antibody fragment is a peptide comprising one or more complementarity determining regions (CDRs) of an antibody. CDRs (also termed "minimal recognition units" or "hypervariable region") can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., *Methods: A Companion to Methods in Enzymology*, 2:106 (1991); Courtenay-Luck, "Genetic Manipulation of Monoclonal Antibodies," in *Monoclonal Antibodies Production, Engineering and Clinical Application*, Ritter et al. (eds.), page 166, Cambridge University Press (1995); and Ward et al., "Genetic Manipulation and Expression of Antibodies," in *Monoclonal Antibodies: Principles and Applications*, Birch et al., (eds.), page 137, Wiley-Liss, Inc. (1995)).

An antibody for use in the methods of the invention may be a human antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences—such antibodies are typically referred to as chimeric or humanised.

A human antibody for use the methods of the invention is typically a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell. Human antibodies may also be prepared by in vitro immunisation of human lymphocytes followed by transformation of the lymphocytes with Epstein-Barr virus. The term "human antibody derivatives" refers to any modified form of the human antibody, e.g., a conjugate of the antibody and another agent or antibody.

Any antibody referred to herein may be provided in isolated form or may optionally be provided linked (directly or indirectly) to another moiety. The other moiety may be a therapeutic molecule such as a cytotoxic moiety or a drug.

The person skilled in the art is capable of screening for suitable antibodies that bind specifically to TIM-1, IL-10R, CD154, CD20, CD19 or CD40. Antibodies may be raised using the full-length antigen proteins, or using a fragment of the target antigen protein. For example, the antibody may be raised using the extracellular domain or a soluble fragment of the target antigen.

The present invention also provides a pharmaceutical composition comprising an antibody that binds TIM-1 on the surface of Breg cells for use in the treatment of cancer or infection. The present invention also provides a pharmaceutical composition comprising an antibody that binds IL-10R on the surface of Breg cells for use in the treatment of cancer or infection. The present invention also provides a pharmaceutical composition comprising an antibody that binds CD154 on the surface of Breg cells for use in the treatment of cancer or infection. The present invention also provides a pharmaceutical composition comprising an antibody that binds CD40 on the surface of Breg cells for use in the treatment of cancer or infection. The present invention also provides a pharmaceutical composition comprising a bispecific antibody that binds to TIM-1 and CD154, TIM-1 and CD20, CD154 and CD20, TIM-1 and CD19 or CD154 and CD19, preferably TIM-1 and CD154, TIM-1 and CD20 or CD154 and CD20, most preferably TIM-1 and CD154, on the surface of Breg cells for use in the treatment of cancer or infection. The present invention also provides a pharmaceutical composition comprising a tri-specific antibody that binds to TIM-1, CD154 and CD20 or TIM-1, CD154 and CD19, preferably TIM-1, CD154 and CD20, on the surface of Breg cells for use in the treatment of cancer or infection. The present invention also provides a pharmaceutical composition comprising a multi-specific antibody that binds to TIM-1 and/or CD154 and any one of CD20, CD19, IL-10R, CD40, CD25, CD71, CD39, CD122 or B7-H4, or combinations thereof, on the surface of Breg cells for use in the treatment of cancer or infection.

In some embodiments, the pharmaceutical compositions of the invention further comprise a pharmaceutically acceptable carrier. Examples of pharmaceutically acceptable carriers suitable for use in the compositions of the invention are well known to the skilled person but may include buffer solutions (e.g. phosphate), sugar or carbohydrate solutions (e.g. glucose or sucrose, sorbitol, or dextran), protein solutions (e.g. albumin or serum), cell culture liquids, cell media, culture media, media, gels, emulsions, DMSO, human serum albumin, oils or saline solutions. The pharmaceutical compositions of the invention may further comprise, for example, stabilizers, preservatives, diluents, emulsifiers and lubricants. Suitable additional components of the pharmaceutical compositions of the invention are well known to the skilled person.

In preferred embodiments, the Breg cell population of any of the aspects described herein is characterised in that the B cells have the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$. In further preferred embodiments, the cancer or infection is characterised by the presence of B cells having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$ and/or wherein the B cells have suppressive function. In some embodiments, the cancer or infection is characterised in that the number and/or percentage of B cells in the patient having the phenotype $CD73^-CD71^+CD25^+$ or $TIM-1^+CD154^+$; preferably $CD73^-CD71^+CD25^+CD154^+$ or $CD73^-CD71^+CD25^+TIM-1^+$; most preferably $CD73^-CD71^+CD25^+TIM-1^+CD154^+$ is increased in comparison to a control. Suitable methods for identifying such cancers or infections are described herein, for example the methods for diagnosing cancer or infection in a patient sample may be applied to determining cancers or infections suitable for treatment using the antibodies of the invention.

The pharmaceutical compositions of the present invention for use in the treatment of cancer or infection may be administered by any suitable means, which could be easily identified by a person skilled in the art. Suitable means for administration include intraperitoneal, parenteral, intravenous, intramuscular, subcutaneous, transdermal, transmucosal, oral, nasal, per rectum, enteral or intrathecal. Preferably, the pharmaceutical compositions of the present invention may be formulated as an injectable formulation.

EXAMPLES

Figure 1C:
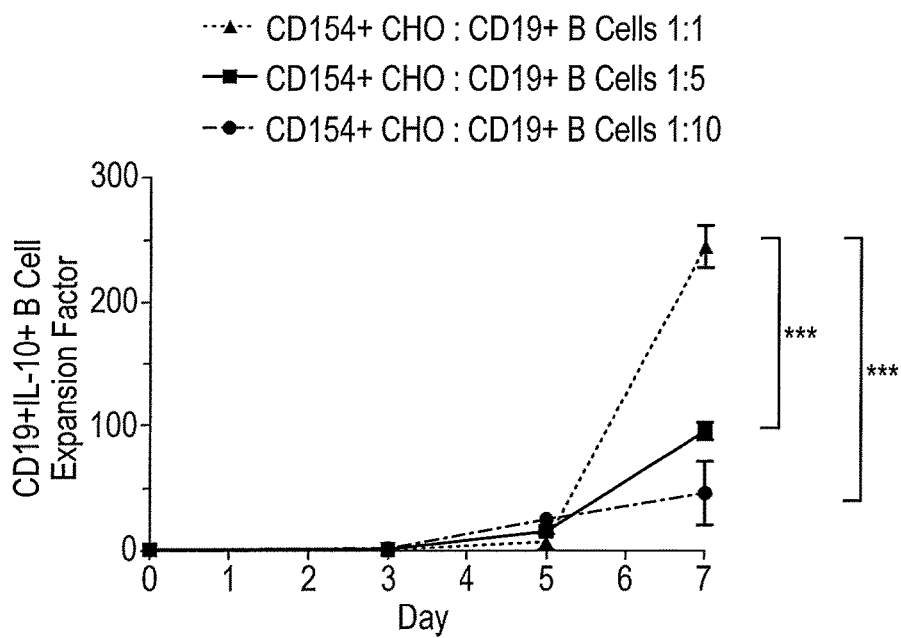
Figure 2A:
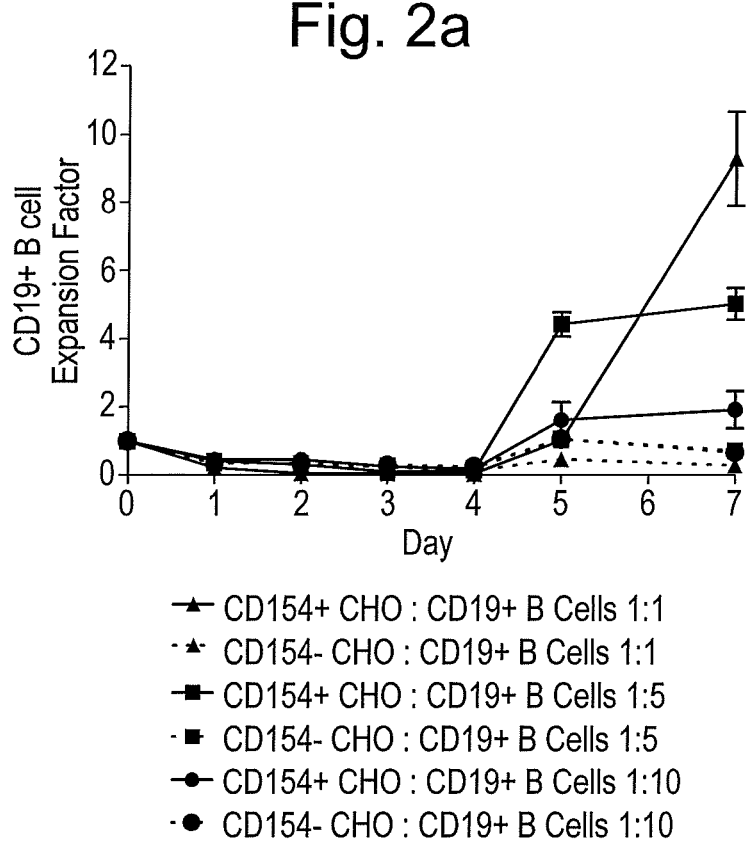
FIG. 2. (a) Expansion of CD19+ B cells is driven by CD154 stimulation by CD154+ CHO cells. Human CD19−B cells were co-cultured with either CD154+ CHO cells or CD154− CHO cells at decreasing ratios. At all ratios, expansion factor of CD19+ B cells was significantly higher when co-cultured with CD154+ CHO cells. (b) expBreg generated by co-culture of CD154+ CHO cells with CD19+ B cells at a 1:1 ratio for 7 days, are significantly more potent than expBreg generated by lower co-culture ratios. p<0.005, *p<0.0001, paired t-test. (c) expBreg do not up-regulate phenotypic markers associated with other mouse or human Breg subsets. Filled histogram represents mf–1 control (mean fluorescence minus one); open histogram represents antibody staining. ***p<0.0001, paired t-test. Error bars in each panel represent Mean +/– SD. Data are representative of 5 independent experiments using CD19+ B cells from 5 different human donors.

Induction of IL-10 expression by human $CD19^+$ B cells can be driven by CD154, a ligand which is up-regulated by early-activated $CD4^+$ T cells [20]. The CD154-CD40 interaction has been used to effectively expand mouse B10 cells in vitro [15]. We found that co-culture of human $CD19^+$ B cells with an irradiated $CD154^+$ Chinese Hamster Ovary (CHO) cell line in the presence of cytokines IL-2, IL-4 and IL-10 for 7 days resulted in rapid proliferation of human $CD19^+$ B cells (FIG. 1a & FIG. 2a). The rate of $CD19^+$ B cell expansion correlated with the ratio of $CD154^+$ CHO cells to $CD19^+$ B cells (FIG. 1a). IL-10 expression by $CD19^+$ B cells significantly increased following expansion, but there was no significant difference in the percentage of $CD19^+IL-10^+$ B cells generated by varying the ratio of $CD154^+$ CHO cells to $CD19^+$ B cells (FIG. 1b). Optimal expansion conditions consistently resulted in greater than 200 fold expansion of human $CD19^+IL-10^+$ B cells (FIG. 1c).

Figure 1D:
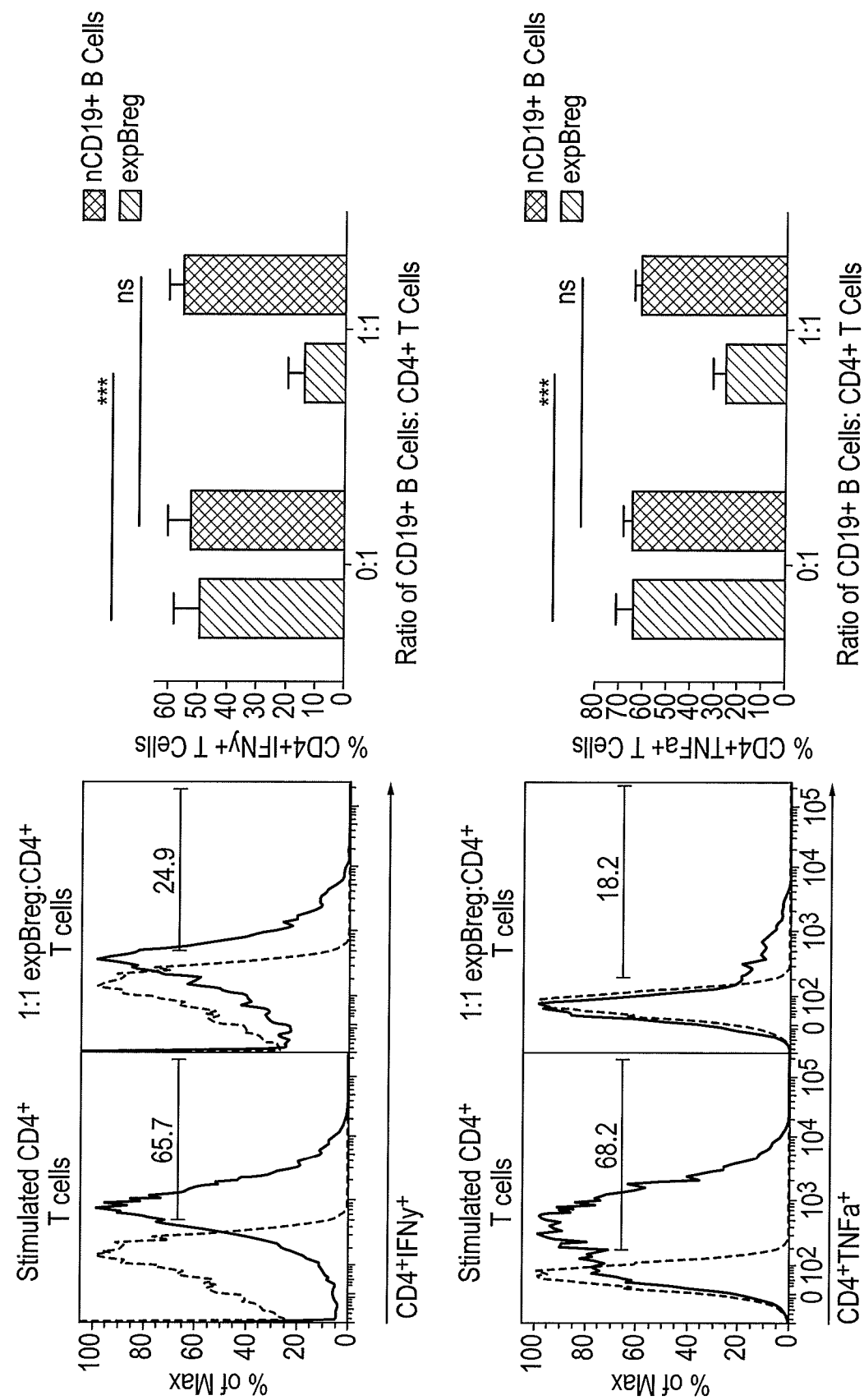
Figure 1E:
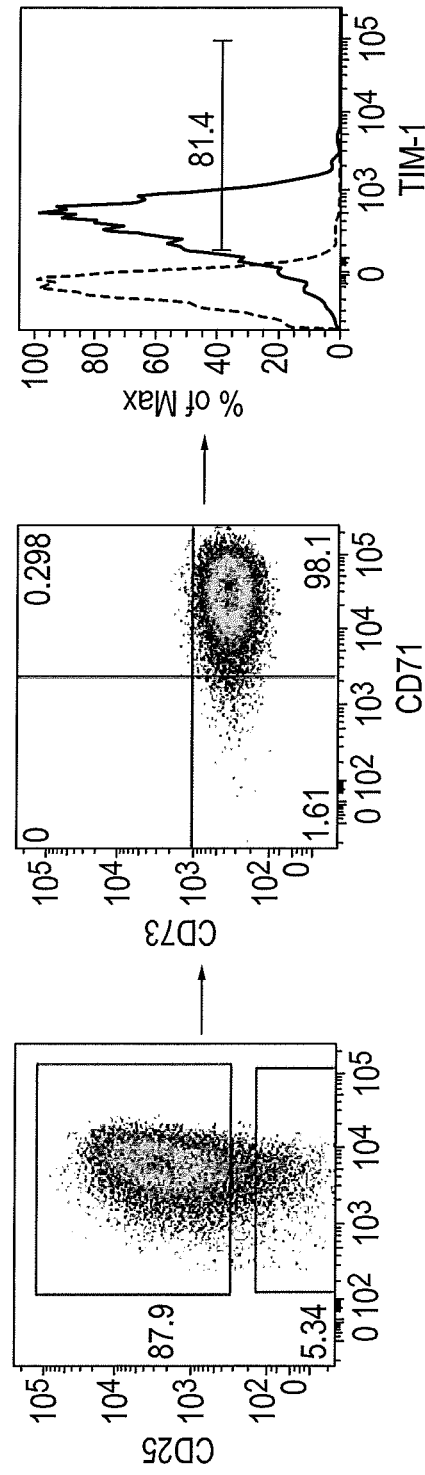
Figure 1E:
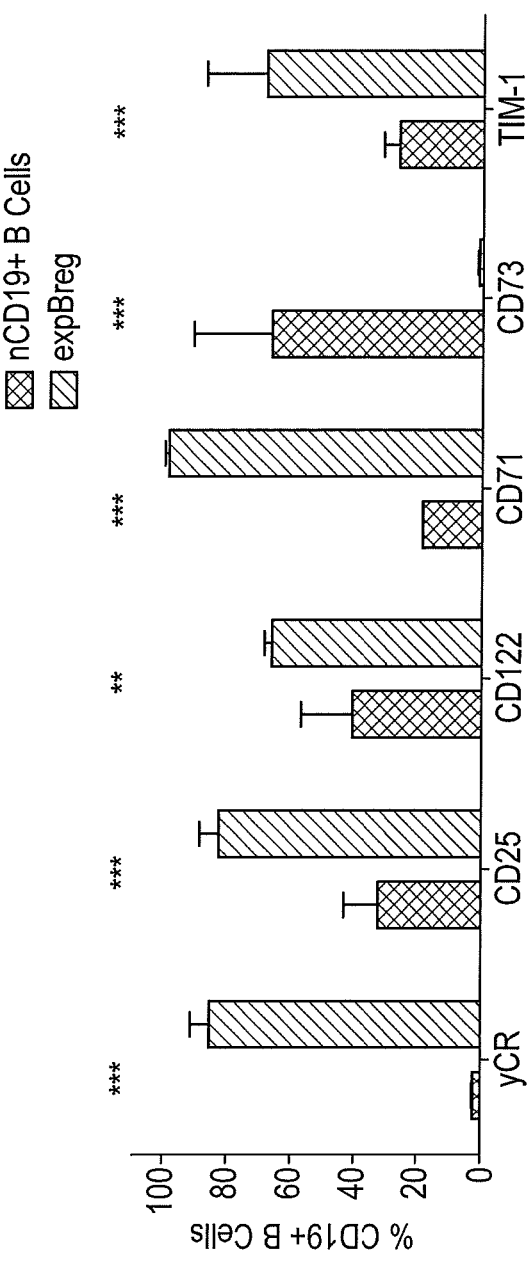
Figure 2B:
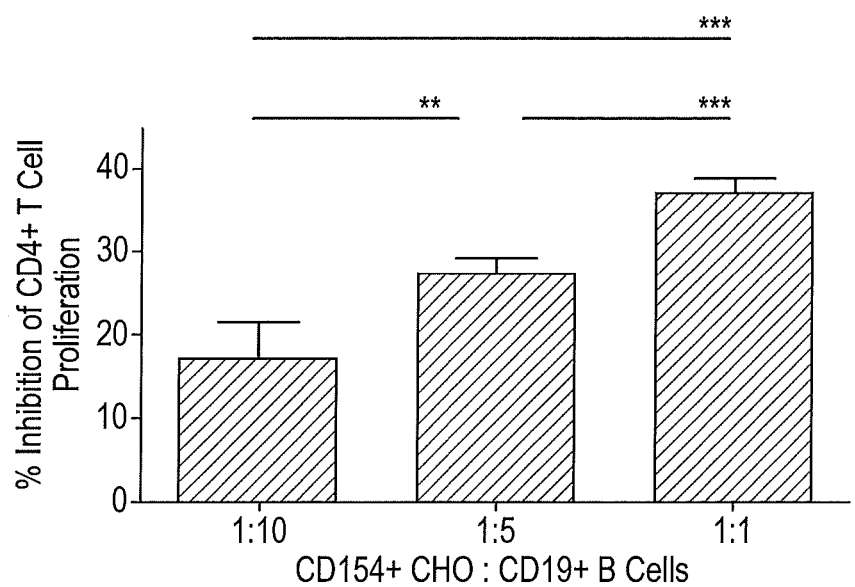
Figure 2C:
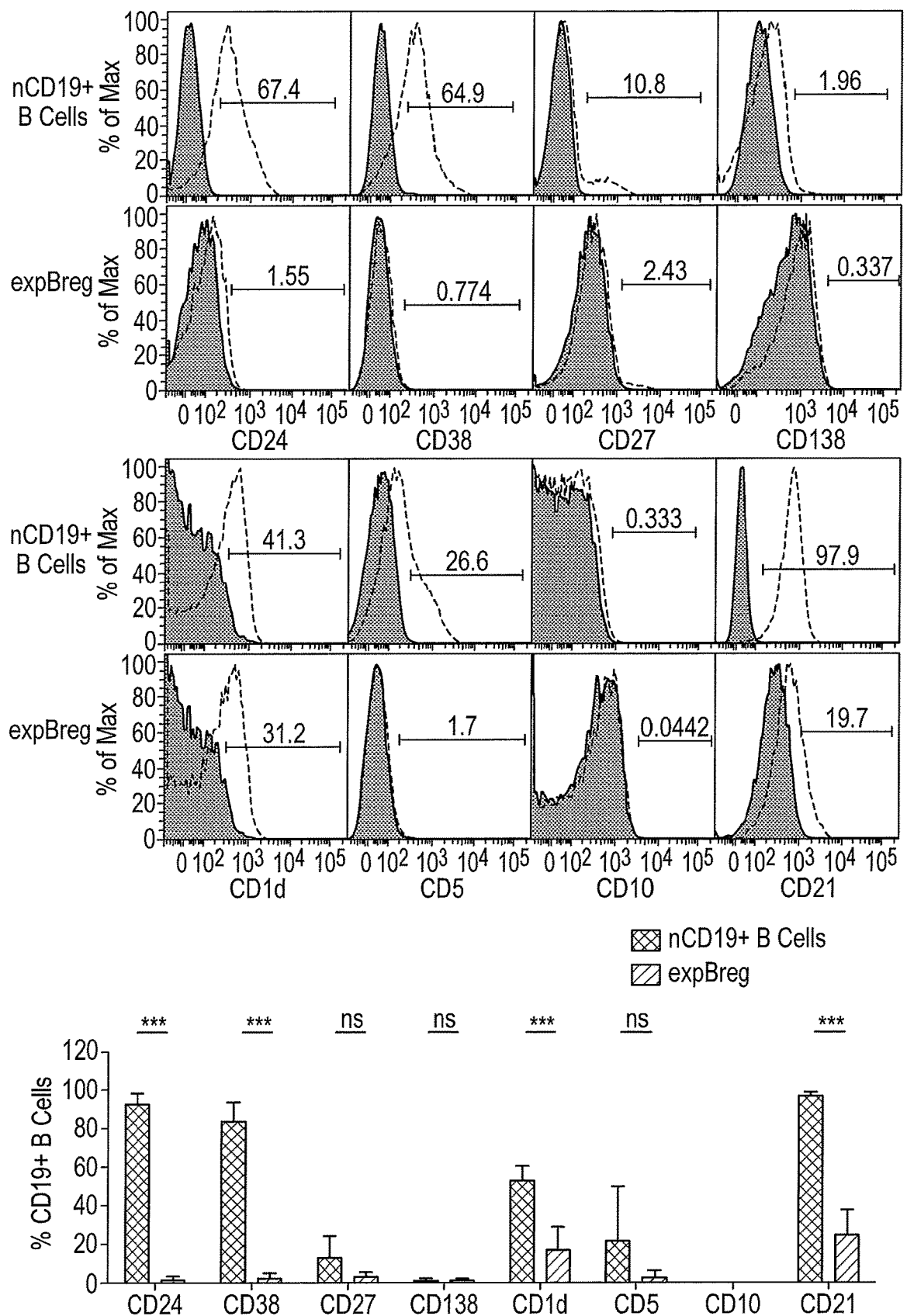

Expanded human $CD19^+$ B cells (expBreg) significantly suppressed autologous $CD4^+$ T cell proliferation in vitro in a dose-dependent manner, at ratios as low as 0.5:1 expBreg to $CD4^+$ T cells (FIG. 1d). In addition, expBreg significantly inhibited expression of inflammatory cytokines, interferon-γ (IFNγ) and tumour necrosis factor α (TNFα) by $CD4^+$ T cells (FIG. 1d). expBreg which had been expanded at 1:1 ratio of $CD154^+$ CHO cells to $CD19^+$ B cells, were also more suppressive than those expanded at lower ratios (FIG. 2b), indicating that high levels of CD154-mediated B cell stimulation were important to suppressive potency. Unexpanded $CD19^+$ B cells ($nCD19^+$ B cells) were unable to suppress $CD4^+$ T cell proliferation or inflammatory cytokine expression in vitro (FIG. 1d). Phenotypic analysis revealed that, expBreg were predominantly $CD73^-CD25^+CD71^+$ (FIG. 1e). Furthermore, the $CD73^-CD25^+CD71^+$ expBreg expressed TIM-1 (FIG. 1e). To our knowledge, this is the first description of TIM-1 expression by a functionally suppressive, ex vivo-generated human Breg subset. expBreg did not significantly up-regulate markers associated with other human or mouse Breg subsets (FIG. 2c).

Figure 3A:
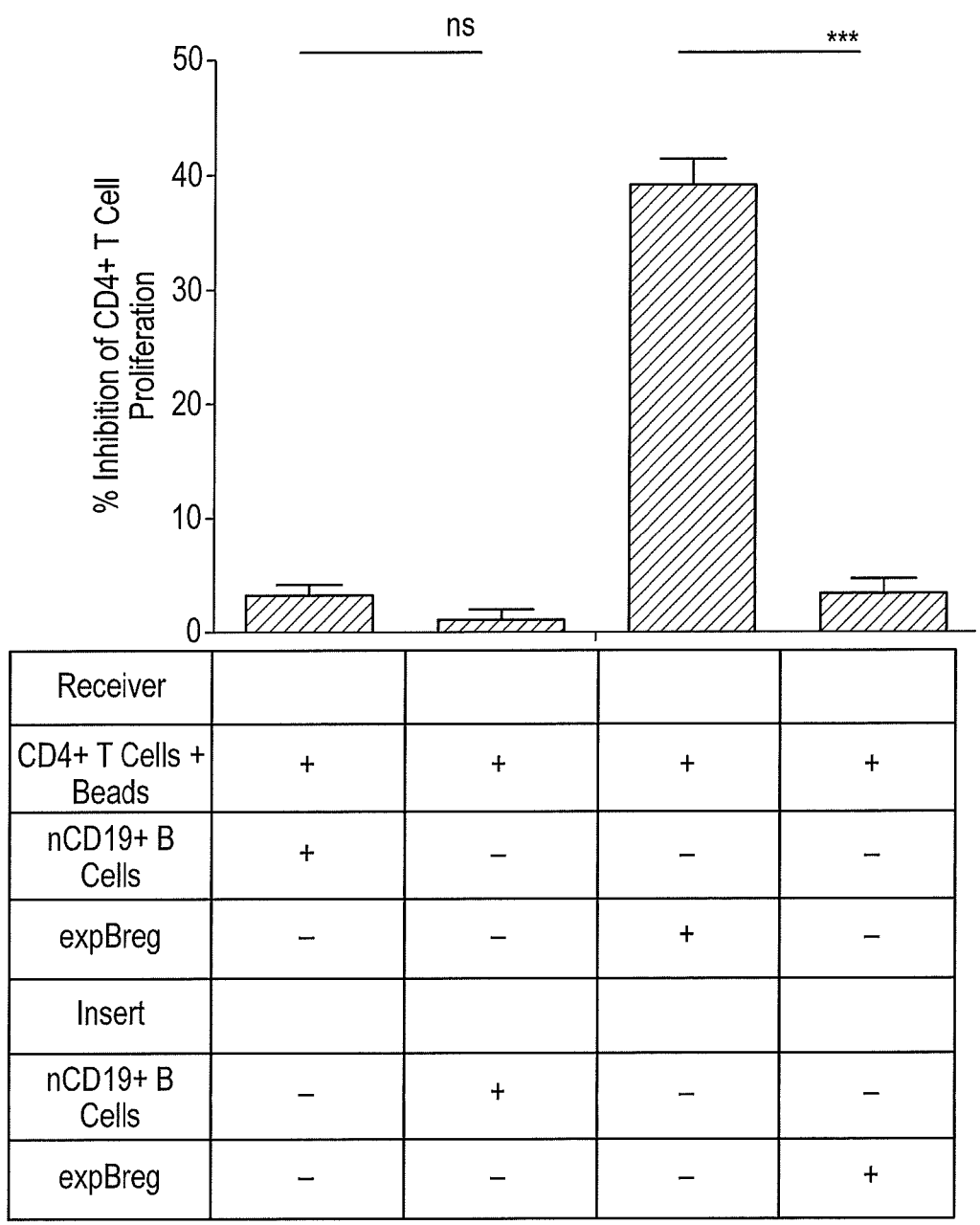
FIG. 3. TIM-1 modulates expBreg suppressive function by regulating expBreg intracellular responses to autocrine IL-10. (a) Transwell assays demonstrate that expBreg suppress autologous CD4+ T cells by cell-cell contact. 'Receiver' refers to the bottom receiver well of the transwell system whilst 'Insert' refers to the transwell insert. *p<0.0001, paired t-test. (b) expBreg-mediated suppression of CD4+ T cells requires sustained CD154-CD40 interaction. When blocking CD154 mAb [10 ug/ml] was added on day (d) 1, d2, d3 or d4, % suppression of CD4+ T cell proliferation of by expB10 cells was reduced compared to the absence of CD154 mAb. p<0.005, *p<0.0001, paired t-test. (c) CD154+ expBreg are more suppressive than CD154− expBreg. Representative histograms of live CD4+ CFSE+ T cells when cultured for 5 days with anti-CD3/CD28 beads alone or with CD154+ or CD154− expBreg, are shown. Solid line, CD4+ T cells alone; dotted line, CD4+ T cells+CD154− expBreg; dashed line, CD4+ T cells+CD154+ expBreg. p<0.005, paired t-test. (d) expBreg suppress CD4+ T cell proliferation by a soluble factor following cognate interaction with CD4+ T cells. In the transwell system, CD4+ T cells and anti-CD3/CD28 beads were cultured either in the receiver only or in the receiver and in the insert. expBreg were cultured in the insert only. Black bar, suppression of CD4+ T cell proliferation in receiver; grey bar, suppression of CD4+ T cell proliferation in insert. *p<0.0001, paired t-test. (e) expBreg-mediated suppression of CD4+ T cells is partially dependent on IL-10 and expBreg up-regulate expression of IL-10R. IL-10R expression by expBreg and nCD19+ B cells is shown. Dashed line, mf–1 control; solid line, CD19+ B cells. p<0.005, *p<0.0001, paired t-test. (f) expBreg suppress CD4+ T cell proliferation via autocrine IL-10. Conditions during expBreg expansion were varied as outlined. Suppressive potency of expBreg was analysed in 5-day suppression assays +/– IL-10 & IL-10R blocking mAbs [10 ug/ml] added on d0. p<0.005, *p<0.0001, paired t-test. (g) Blockade of TIM-1 abrogates expBreg STAT3 phosphorylation in response to IL-10. % Increase in pSTAT3 in expBreg and nCD19+ B cells after addition of hIL-10 was measured relative to expBreg and nCD19+ B cells with no hIL-10 added (baseline). expBreg were pre-incubated with IgG isotype control (Isotype-expBreg), anti-CD154 mAb (CD154-blocked-expBreg), anti-IL-10+IL-10R mAbs (IL-10-blocked-expBreg), anti-TIM-1 mAb (TIM-1-blocked-expBreg) or anti-IL-2R mAbs (IL-2R-blocked-expBreg) for the last 48 hours of expansion. Representative histograms of pSTAT3 expression by expBreg +/– TIM-1-blockade or IL-10-blockade are shown. Dashed line, expBreg receiving no exogenous hIL-10; solid line, expBreg incubated with hIL-10 for 10 minutes. p<0.005, ***p<0.0001, paired t-test. (h) TIM-1-blockade inhibits STAT3 phosphorylation in response to multiple cytokines. expBreg were pre-incubated with anti-TIM-1 mAb for 1 hour following harvest from expansion co-cultures. TIM-1-blocked expBreg were then stimulated with either hIL-10 or hIL-21 for 10 minutes and the increase in STAT3 phosphorylation measured. *p<0.05, **p<0.005, paired t-test. (i) TIM-1 modulates expBreg suppression. expBreg pre-incubated with TIM-1, IL-10R or CD154 blocking mAbs had reduced suppressive potency compared to expBreg. *p<0.05, **p<0.005, paired t-test. Error bars in each panel represent Mean +/– SD. Data in above analyses represent 4 independent experiments using CD19+ B cells from 4 different human donors. (j) TIM-1 modulates expBreg suppressive function by regulating phosphorylation of STAT3 within expBreg. CD154 is up-regulated by an activated CD4+ T cell, and interacts with CD40 expressed by an expBreg cell. This results in up-regulation of IL-10 by the expBreg cell, IL-10R on expBreg is engaged by autocrine IL-10, resulting in STAT3 phosphorylation. STAT3 phosphorylation can also be induced by proinflammatory cytokines such as IL-21 when engaging with IL-21R expressed by expBreg. The phosphorylation of STAT3 propagates expBreg suppressive function. However, TIM-1 controls STAT3 phosphorylation in response to cytokine stimulation, thus regulating suppression mediated by expBreg.
Figure 3C:
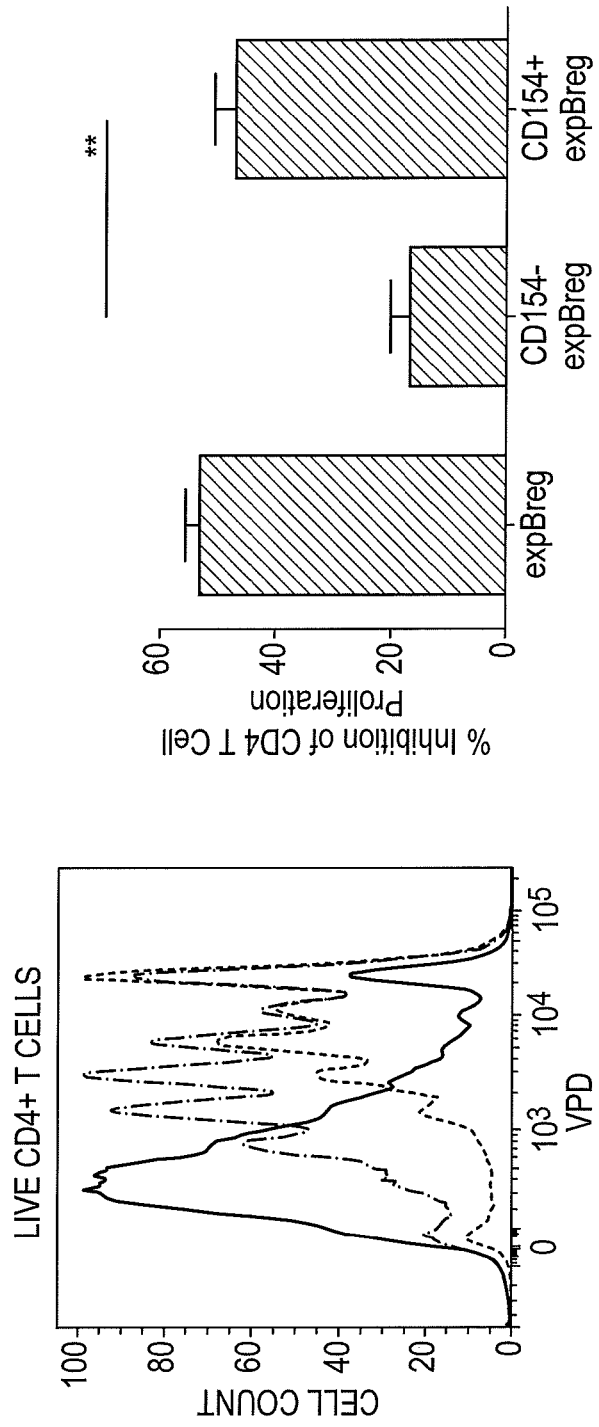
Figure 4A:
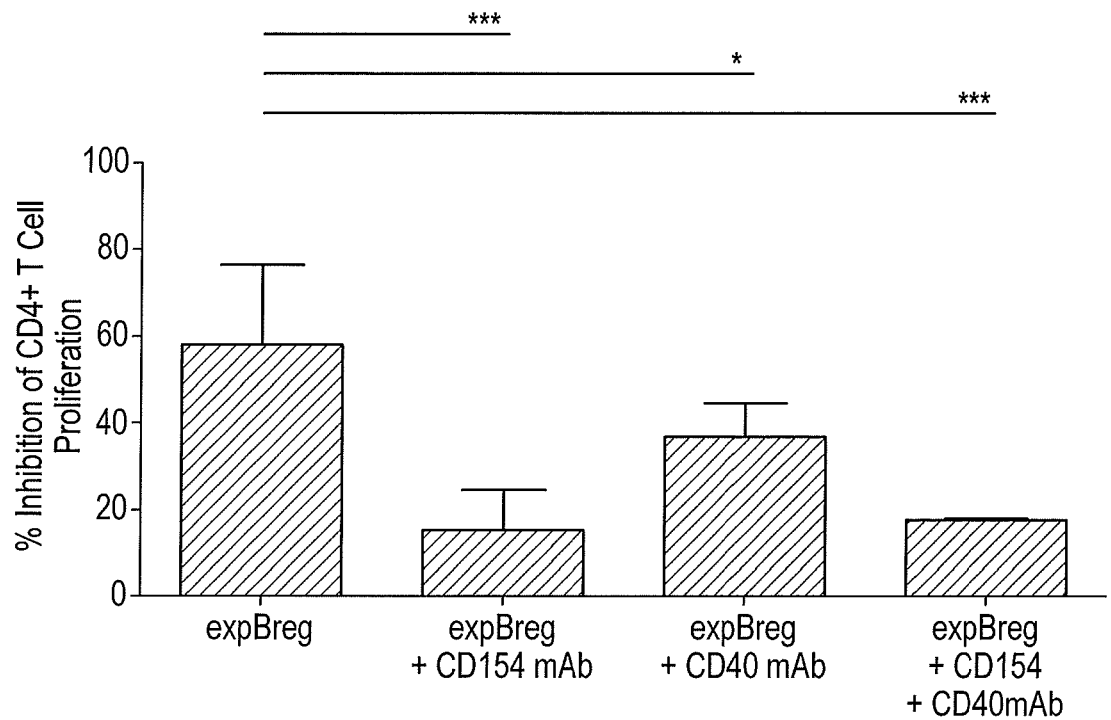
FIG. 4. (a) expBreg-mediated suppression is dependent on the CD154-CD40 interaction. Addition of blocking mAb to CD154 or CD40 [10 ug/ml] on day 0 of the suppression assay significantly reduced % inhibition of CD4+ T cell proliferation by expBreg. *p<0.05, *p<0.0001, paired t-test. (b) Suppressive capacity of expBreg cells increases with exposure to CD154 expressed on activated CD4+ T cells over time. % Inhibition of CD4+ T cell proliferation by expBreg and expression of CD154 on CD4+ T cells was measured daily in the 5-day suppression assay. (c) Sort strategy for CD154+ vs CD154− expBreg cells. (d) Potency of expBreg correlates with expression of CD154 but not CD40. Levels of CD40 and CD154 expressed by non-suppressive nCD19+ B cells, suppressive expBreg which had been expanded at 1:10 CD154+ CHO cell to CD19+ B cell ratio (expBreg 1:10) and the significantly more potently suppressive expBreg which had been expanded at a 1:1 ratio (expBreg 1:1), were measured. Filled histogram, mf–1 control; open histogram, antibody staining. *p<0.0001, paired t-test. (e) expBreg partially suppress expression of pro-inflammatory cytokines by CD4+ T cells in an IL-10-dependent mechanism. p<0.005, paired t-test. (f) Although expBreg up-regulate LAP, expBreg-mediated suppression of autologous CD4+ T cell proliferation is not dependent on TGFβ. *p<0.0001, paired t-test. (g) expBreg produce significantly greater levels of IL-10 compared to nCD19+ B cells, but minimal levels of IL-35. *p<0.05, paired t-test. (h) There is no significant difference in IL-10 secretion by expBreg, expBreg generated without exogenous hIL-10 (expBreg w/o hIL-10), or expBreg generated without exogenous hIL-10 and in the presence of blocking mAbs to IL-10 and IL-10R for the last 48 hrs of expansion (IL-10-blocked-expBreg). (i) There is no significant difference in expression of CD40, 154 or IL-10R between exp-Breg and TIM-1-blocked expBreg. Paired t-test, error bars in each panel represent Mean +/− SD. (j) CD40 stimulation during expansion co-culture results in increased % pSTAT3 expression. expBreg and CD154-blocked expBreg were stained for pSTAT3 immediately after harvest from expansion co-cultures. nCD19$^+$ B cells were also stained for pSTAT3 expression. Dotted line, unstained control; solid line, pSTAT3 staining. Data are representative of 4 independent experiments using CD19$^+$ B cells from 4 different human donors.
Figure 4B:
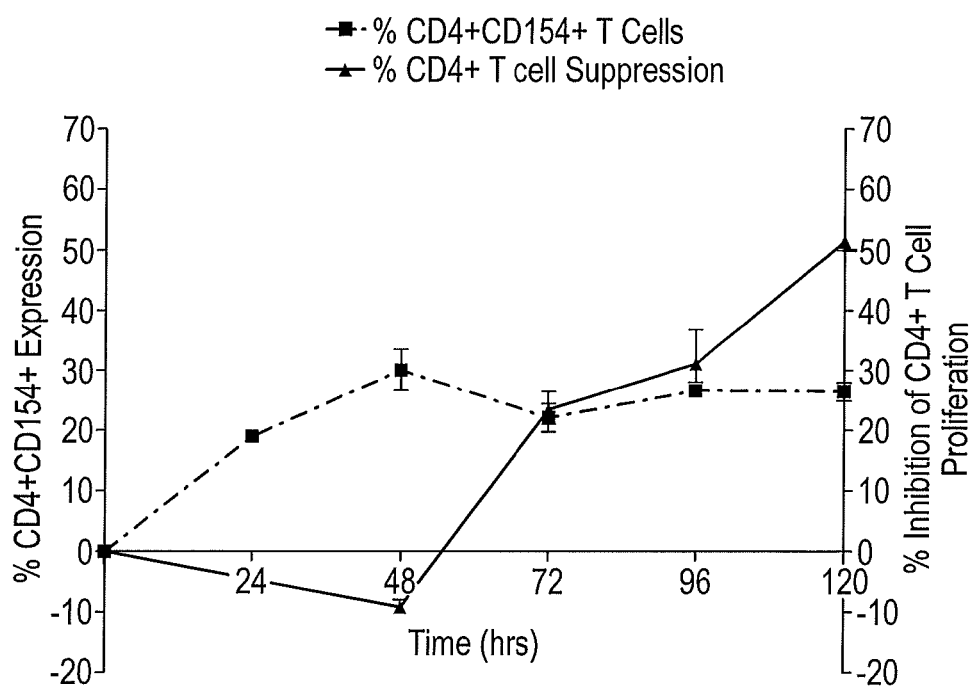

Cognate interaction of expBreg with stimulated $CD4^+$ T cells was crucial to the suppressive function of this human Breg population (FIG. 3a). Antibody-mediated blockade of CD154 or CD40 resulted in abrogation of expBreg-mediated suppression, indicating that it is this cognate interaction which drives suppression of autologous $CD4^+$ T cells by expBreg (FIG. 3b & FIG. 4a). Constant interaction between CD154 and CD40 was required for expBreg-mediated suppression, as $CD4^+$ T cell proliferation recovered when anti-CD154 mAb was added as late as day 4 of a 5-day suppression assay (FIG. 3b), despite significant suppression having already occurred by this point (FIG. 4b). CD154 expression by expBreg was also associated with suppressive potency, as $CD154^+$ expBreg were significantly more suppressive than $CD154^+$ expBreg (FIG. 3c & FIG. 4c); furthermore, the percentage of expBreg cells expressing CD154 increased with $CD154^+$ CHO stimulation (FIG. 4d) and therefore suppressive potency (FIG. 2b). No such association was observed with CD40 expression. Thus, expBreg-mediated suppression is dependent on CD40-CD154 interactions with $CD4^+$ T cells, and CD154 expression by expBreg may also serve as a marker of suppressive potency as well as activation.

Figure 3D:
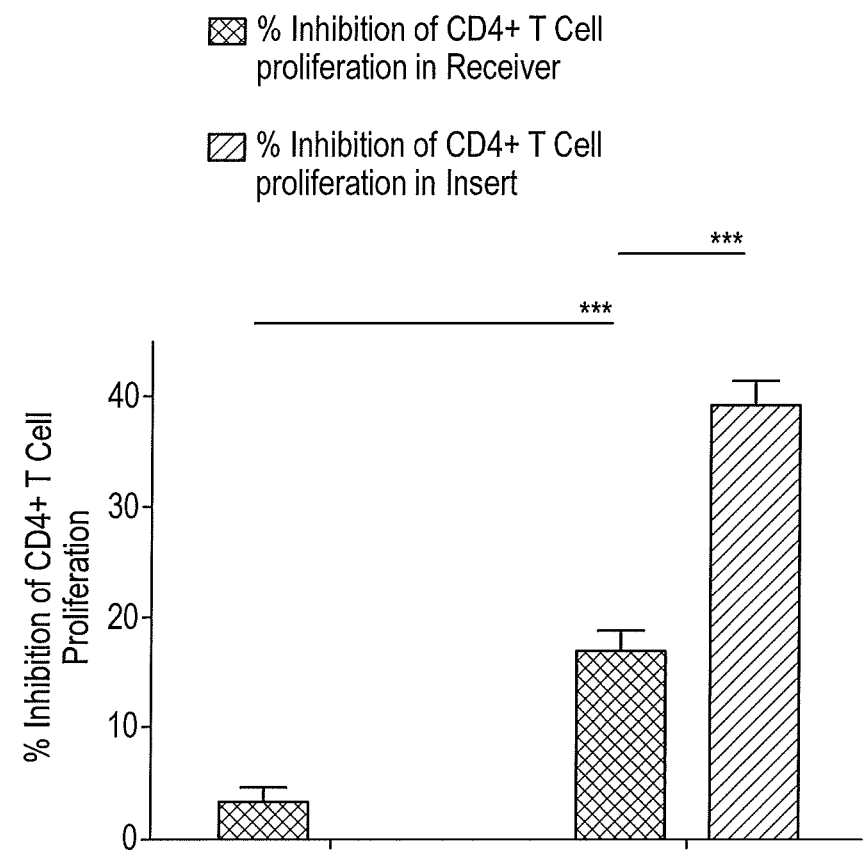
Figure 4E:
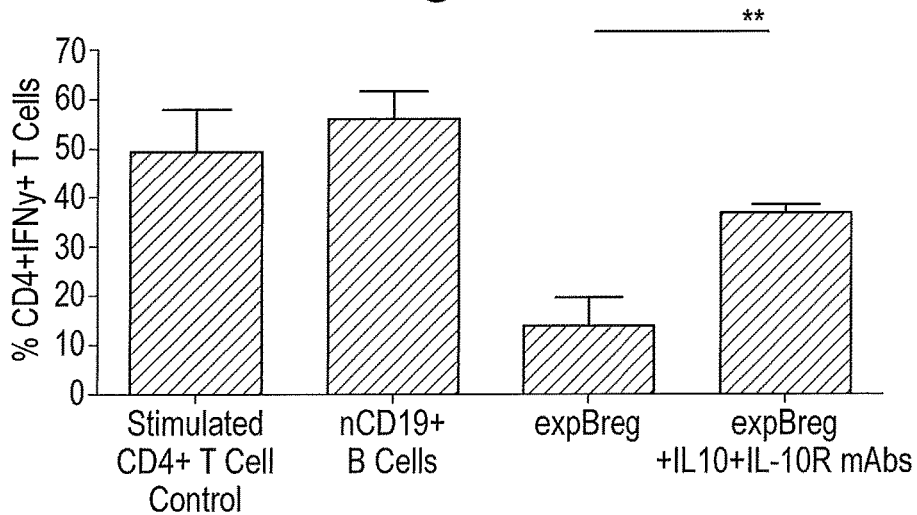
Figure 4E:
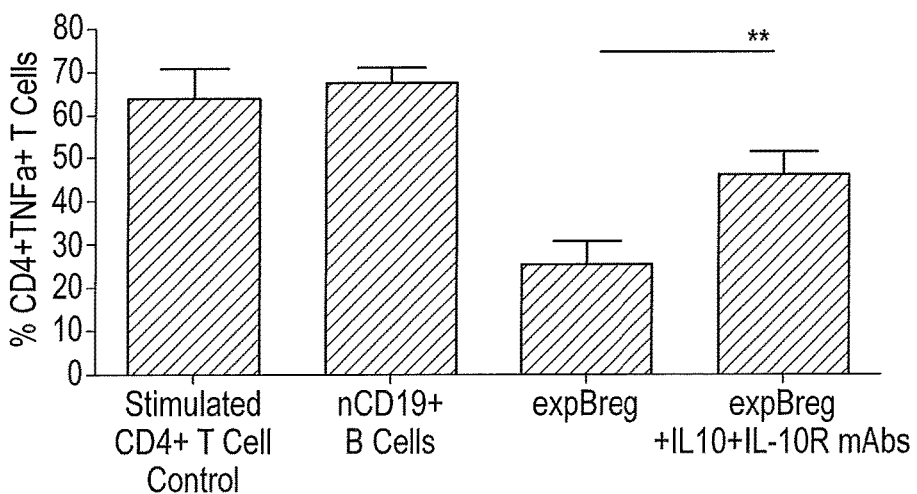
Figure 4F:
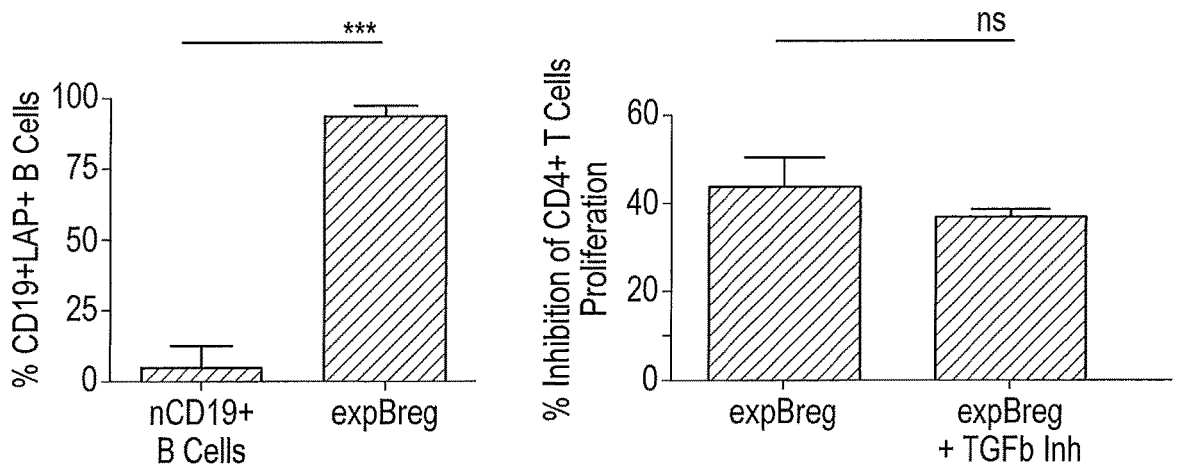
Figure 4G:
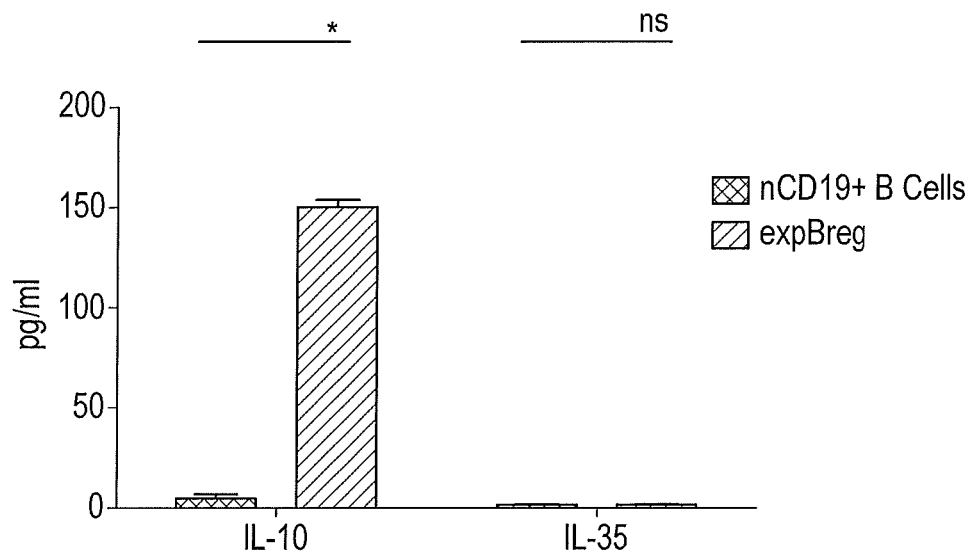

Transwell assays also demonstrated that cognate interactions between expBreg and $CD4^+$ T cells resulted in the release of a soluble factor that partially suppressed the $CD4^+$ T cell response (FIG. 3d). Addition of blocking mAbs to IL-10 and IL-10R to suppression assays confirmed that expBreg-mediated suppression was partially dependent on IL-10 (FIG. 3e & FIG. 4e). Other soluble suppressive factors reported to be secreted by Breg subsets, such as TGFβ and IL-35 [9, 26, 27], were not involved in expBreg-mediated suppression in vitro (FIG. 4f-g).

Figure 3F:
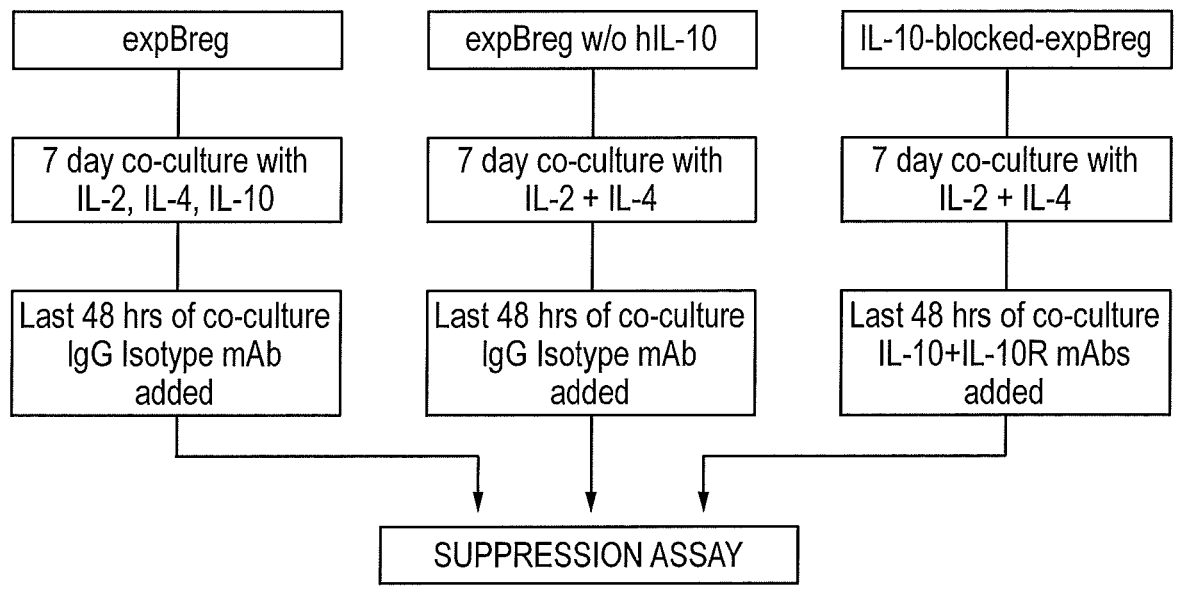
Figure 3F:
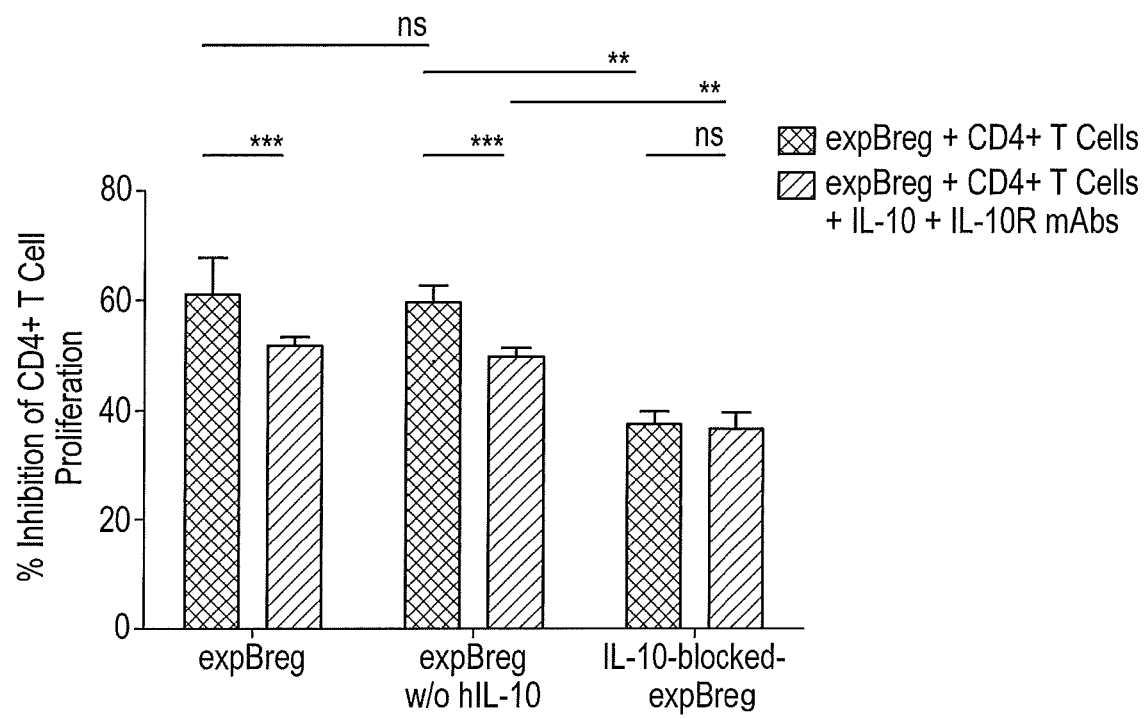
Figure 4H:
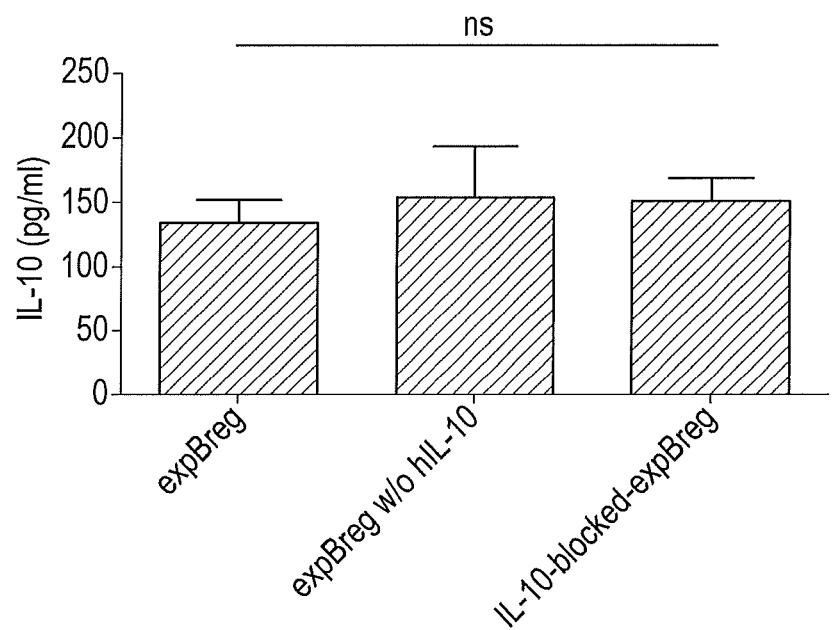

Given that expBreg significantly up-regulated expression of IL-10R as well as IL-10 when compared to $nCD19^+$ B cells (FIG. 3e), we asked whether IL-10 had an autocrine effect on expBreg in vitro. expBreg generated in the absence of exogenous IL-10 and that had also been blocked from any autocrine IL-10 exposure for the last 48 hours of the 7-day expansion co-culture by the addition of anti-IL-10 and anti-IL-10R mAbs (IL-10-blocked expBreg), had significantly reduced suppressive potency when compared to expBreg that did have access to either autocrine IL-10 alone (expBreg w/o hIL-10) or both exogenous and autocrine IL-10 (expBreg) (FIG. 3f). Furthermore, IL-10R blockade during the suppression assay resulted in significantly reduced suppressive potency of both expBreg and expBreg w/o hIL-10, but had no effect on suppressive potency of IL-10-blocked expBreg (FIG. 3f). Expansion factor and IL-10 secretion by expBreg did not vary significantly across the different expansion conditions (FIG. 4h). Thus IL-10 secreted by expBreg exerts a predominantly autocrine effect on expBreg suppressive function in this in vitro system.

Figure 3G:
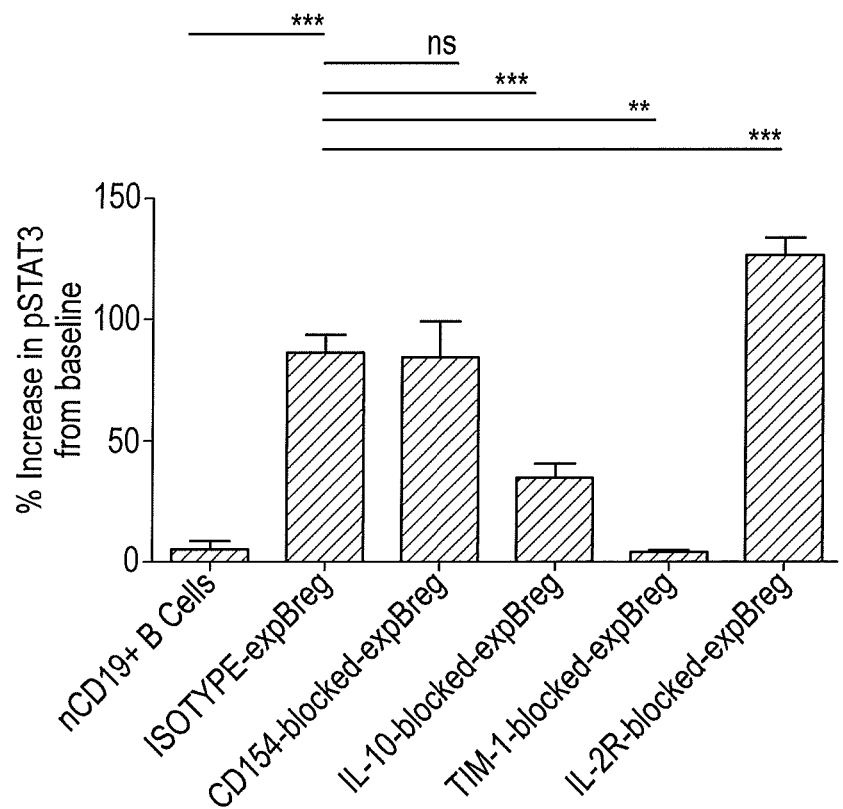
Figure 3G:
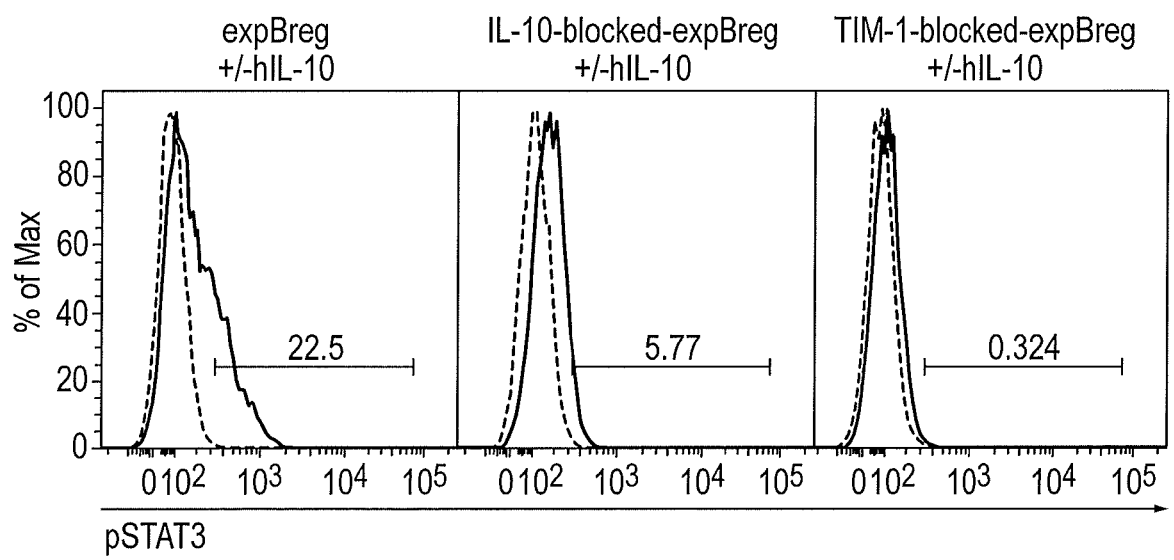
Figure 3H:
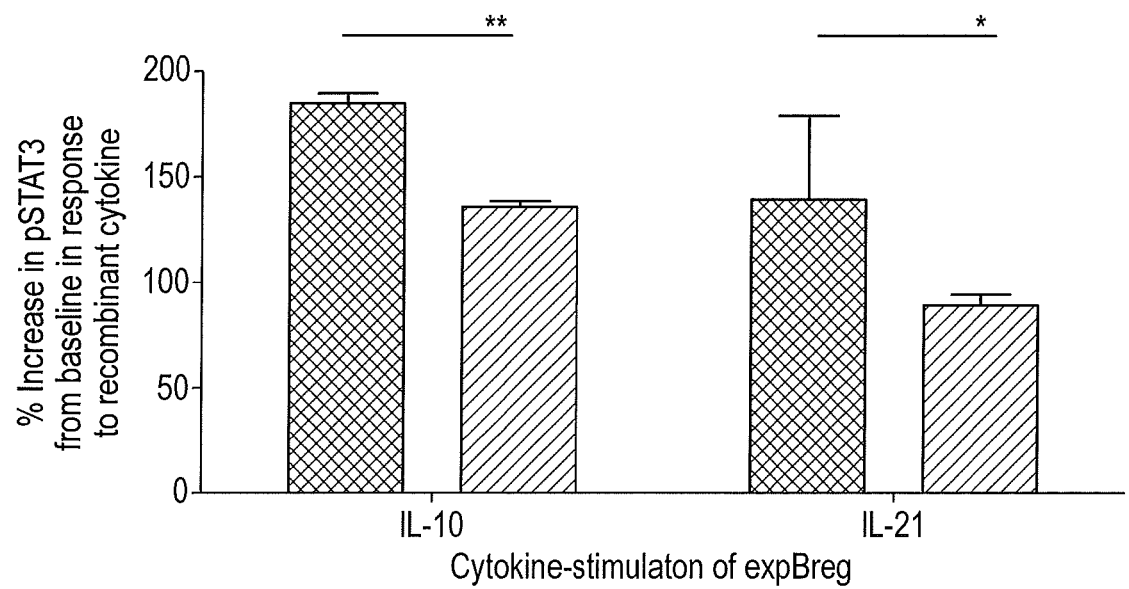
Figure 3I:
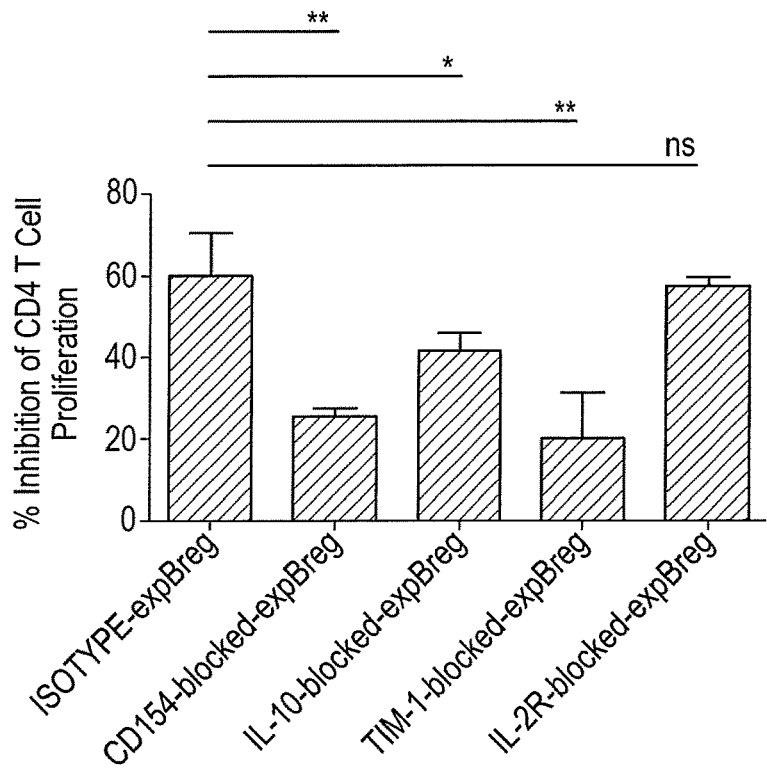
Figure 3J:
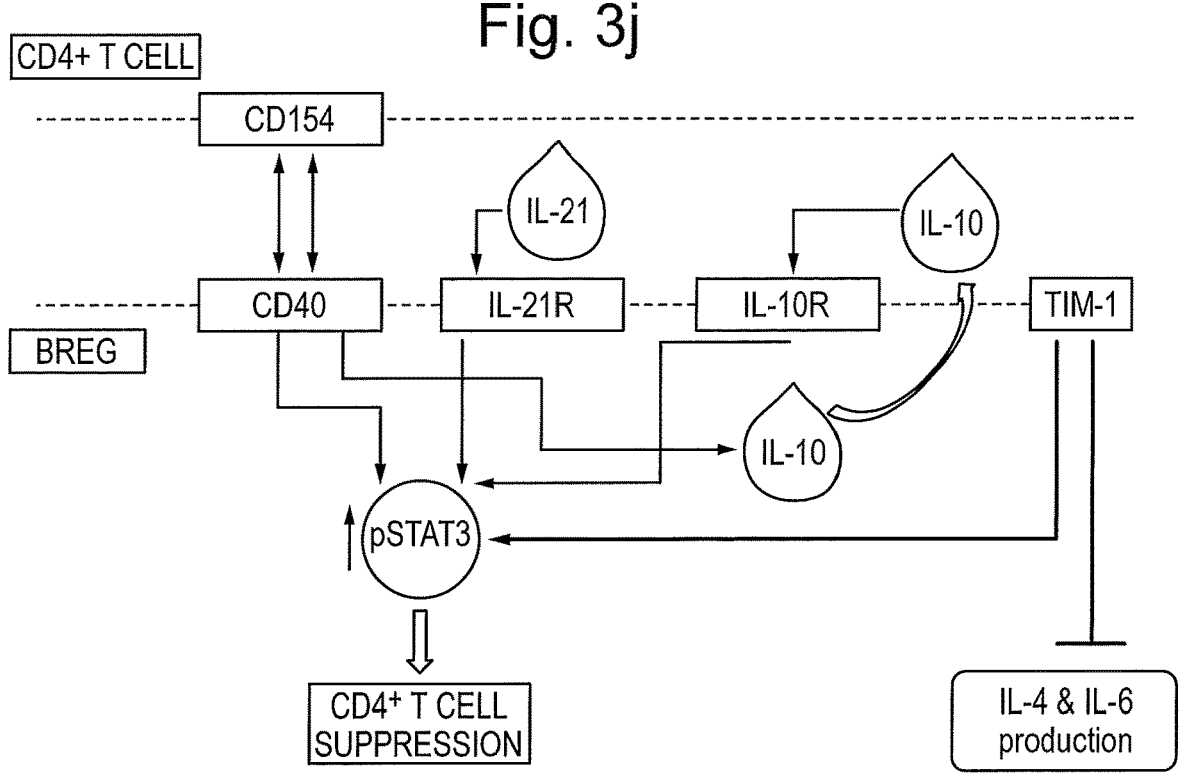
Figure 4I:
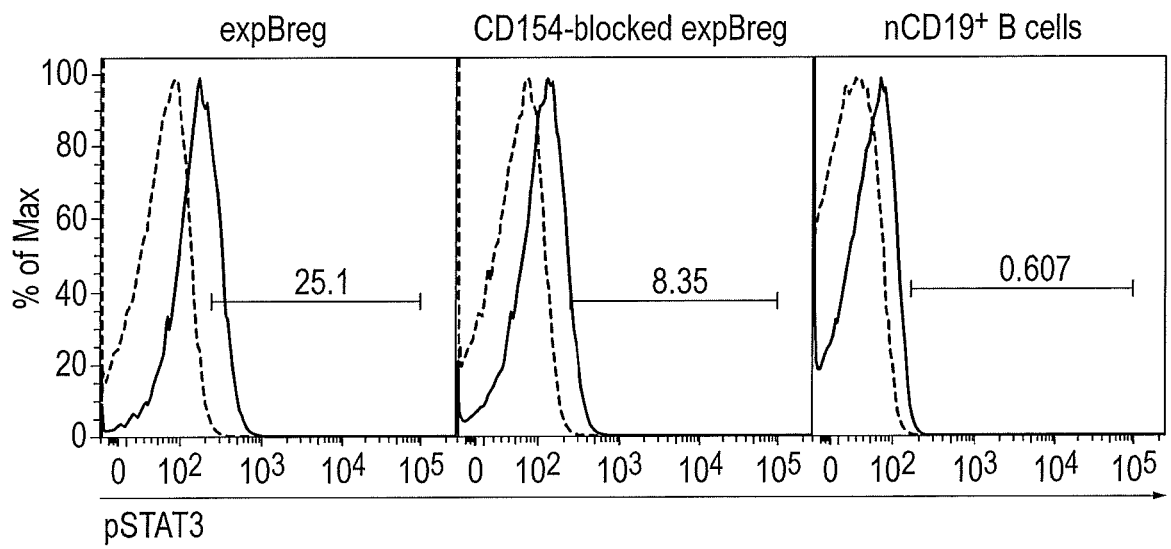
Figure 4J:
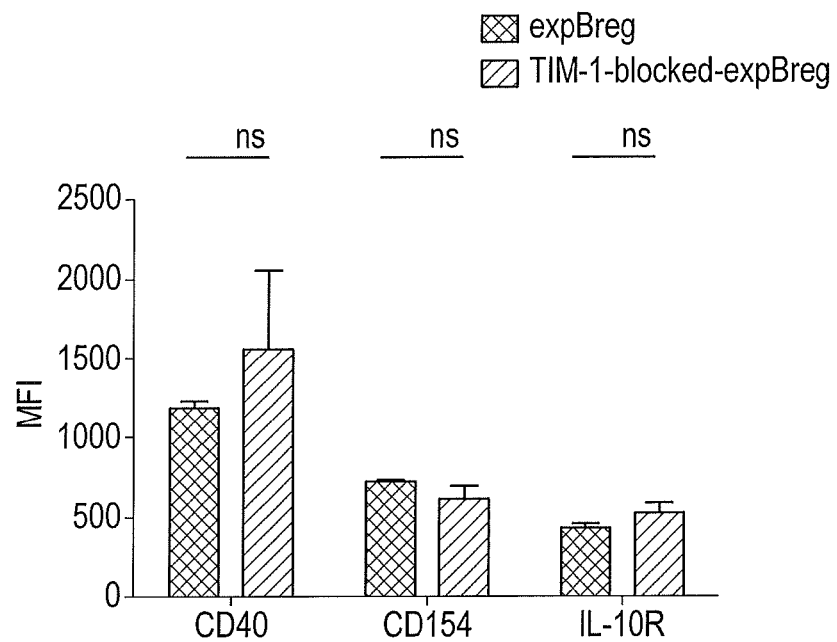
Figure 10A:
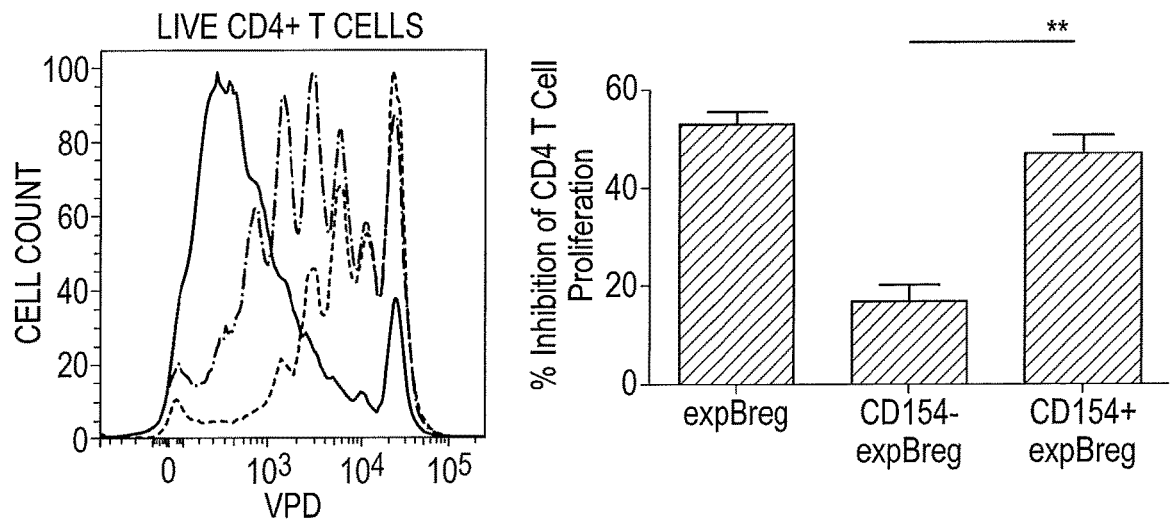
FIG. 10. (a) CD154$^+$ expBreg are significantly more suppressive than CD154$^-$ expBreg. Representative histograms of live CD4$^+$VPD$^+$ T cells when cultured for 5 days with anti-CD3/CD28 beads alone or with CD154$^+$ or CD154$^-$ expBreg, are shown. Solid line, CD4$^+$ T cells alone; dotted line, CD4$^+$ T cells+CD154$^-$ expBreg; dashed line, CD4$^+$ T cells+CD154$^+$ expBreg. p<0.005, paired t-test. (b) TIM-1 is expressed by both CD154$^+$ expBreg and CD154$^-$ expBreg. Representative FACS plots demonstrate TIM-1 staining by FACS-sorted expBreg, gating on a fluorescence-minus-one control. p<0.005, paired t-test. (c) CD154-blocked-expBreg demonstrated reduced suppressive function. To inhibit CD154 when expressed by expBreg, expBreg were pre-incubated with a blocking mAb to CD154 for one hour (CD154-blocked-expBreg), washed and then added to co-cultures of CD4$^+$VPD$^+$ T cells and anti-CD3/CD28 beads within a suppression assay for 5 days. Representative histograms of live CD4$^+$VPD$^+$ T cells are shown.
Figure 10B:
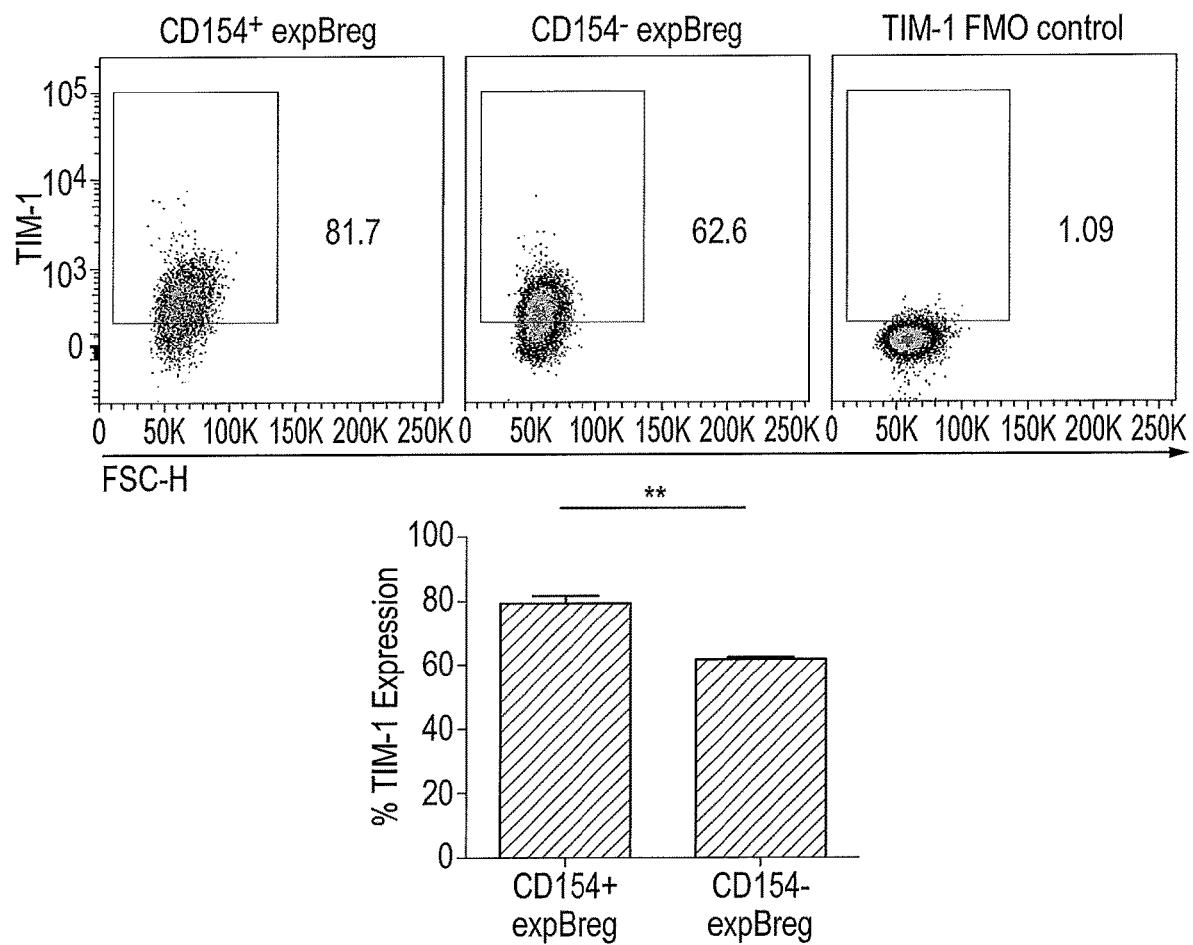
Figure 10C:
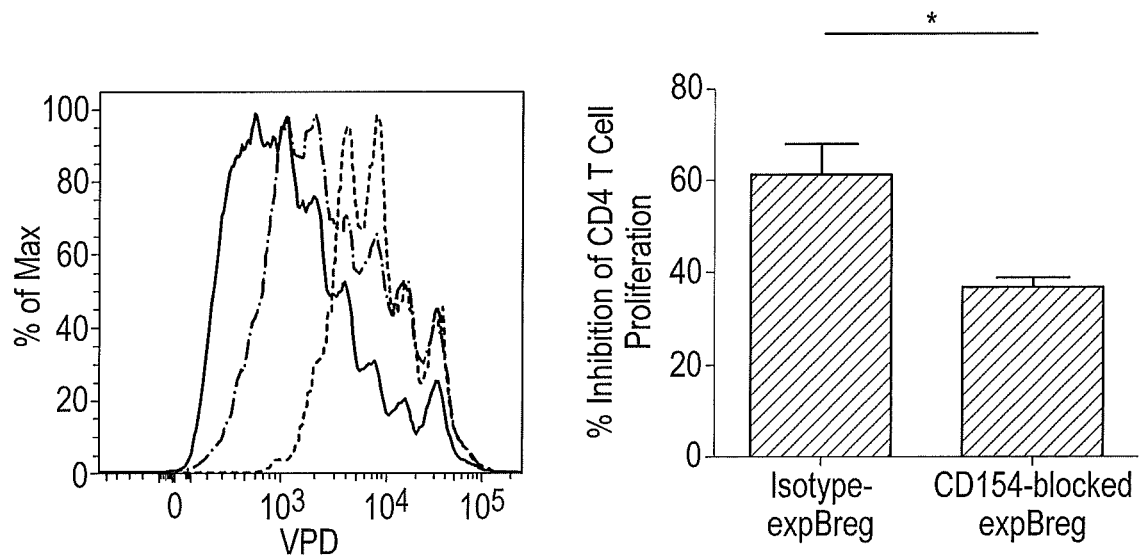
Figure 10D:
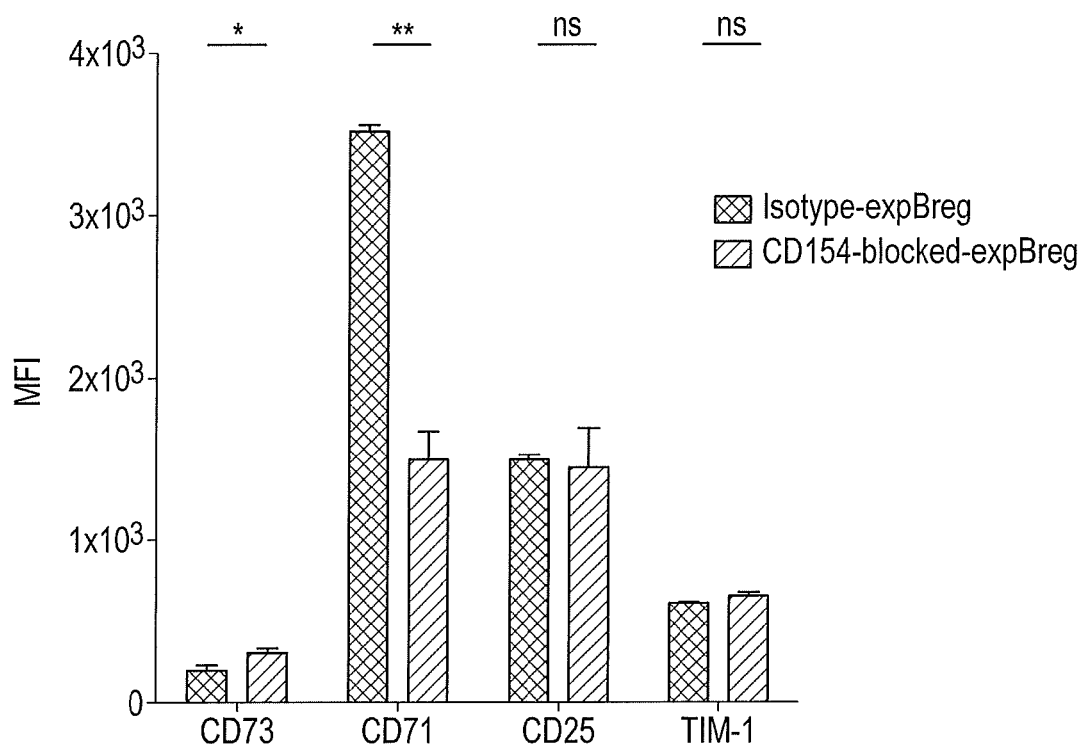
Figure 10E:
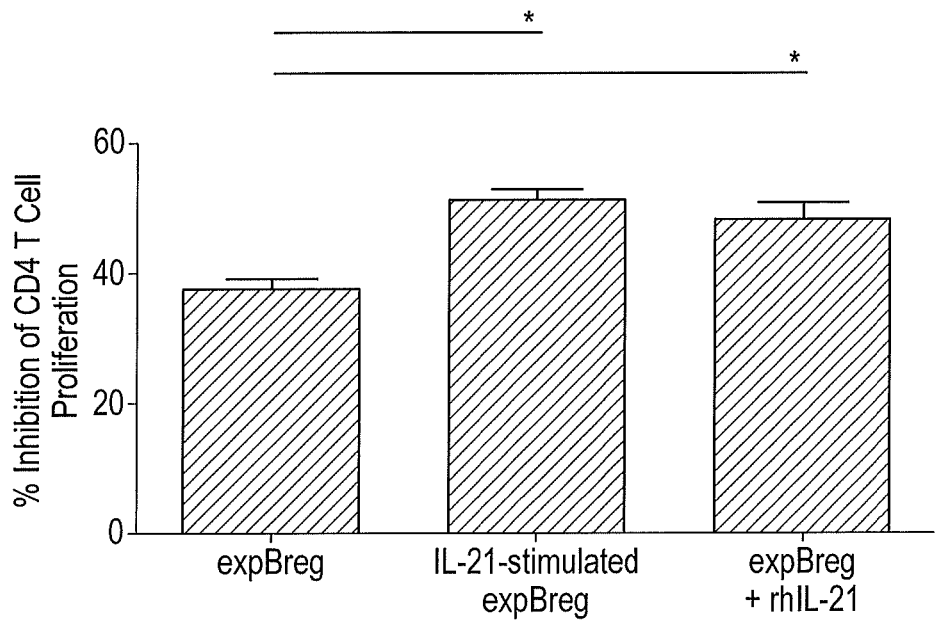
Figure 10F:
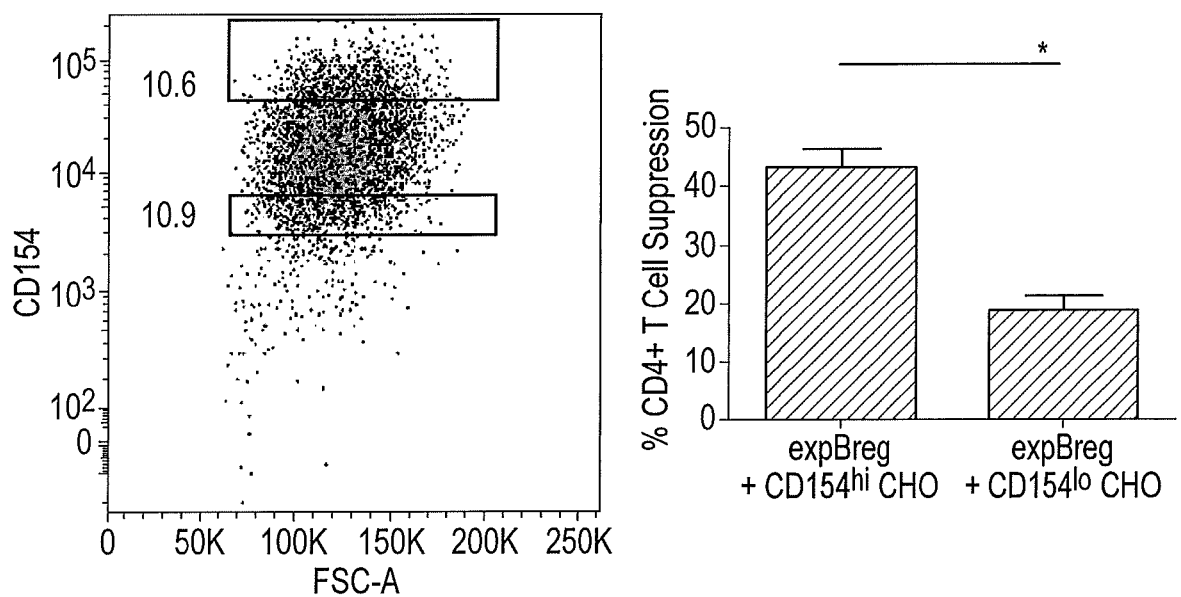
Figure 10G:
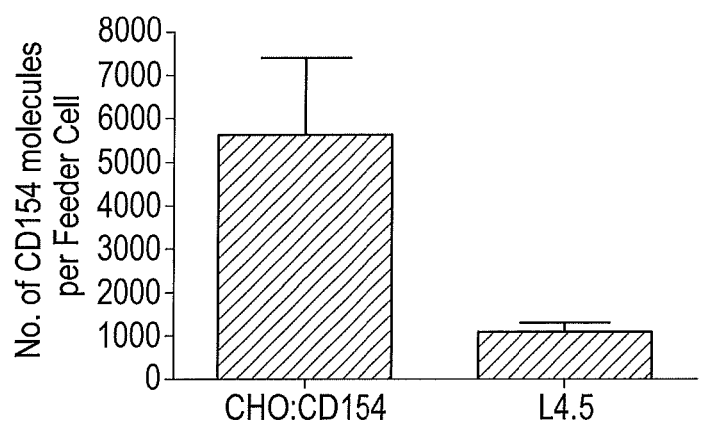
Figure 10G:
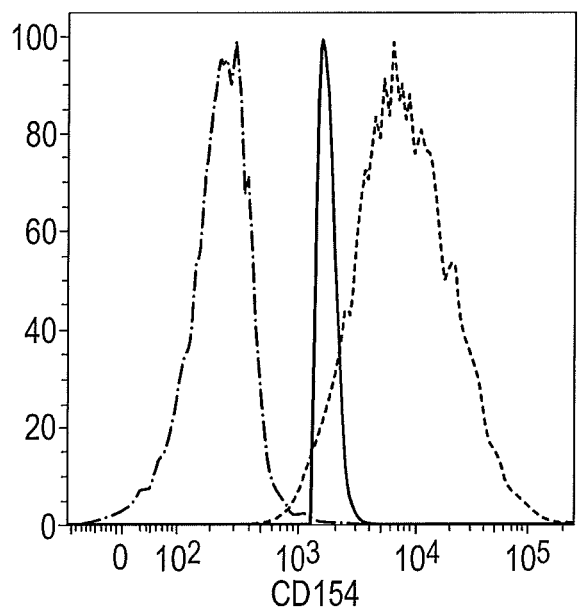
Figure 10H:
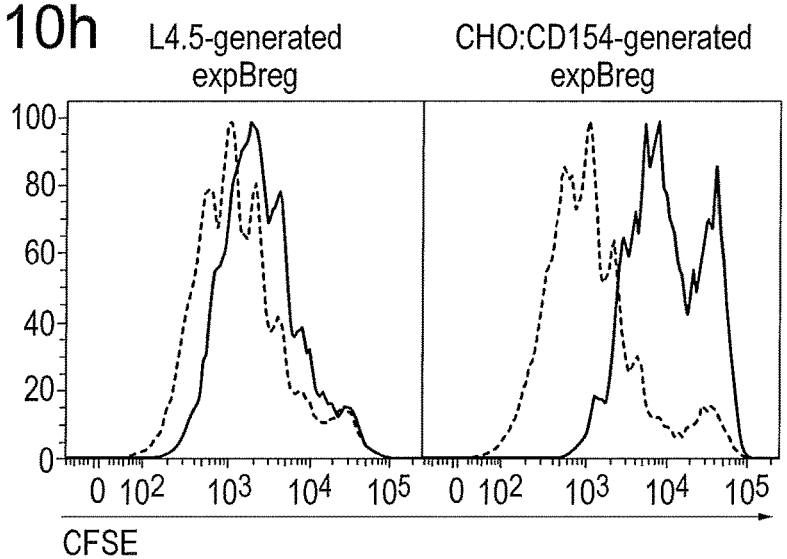
Figure 10I:
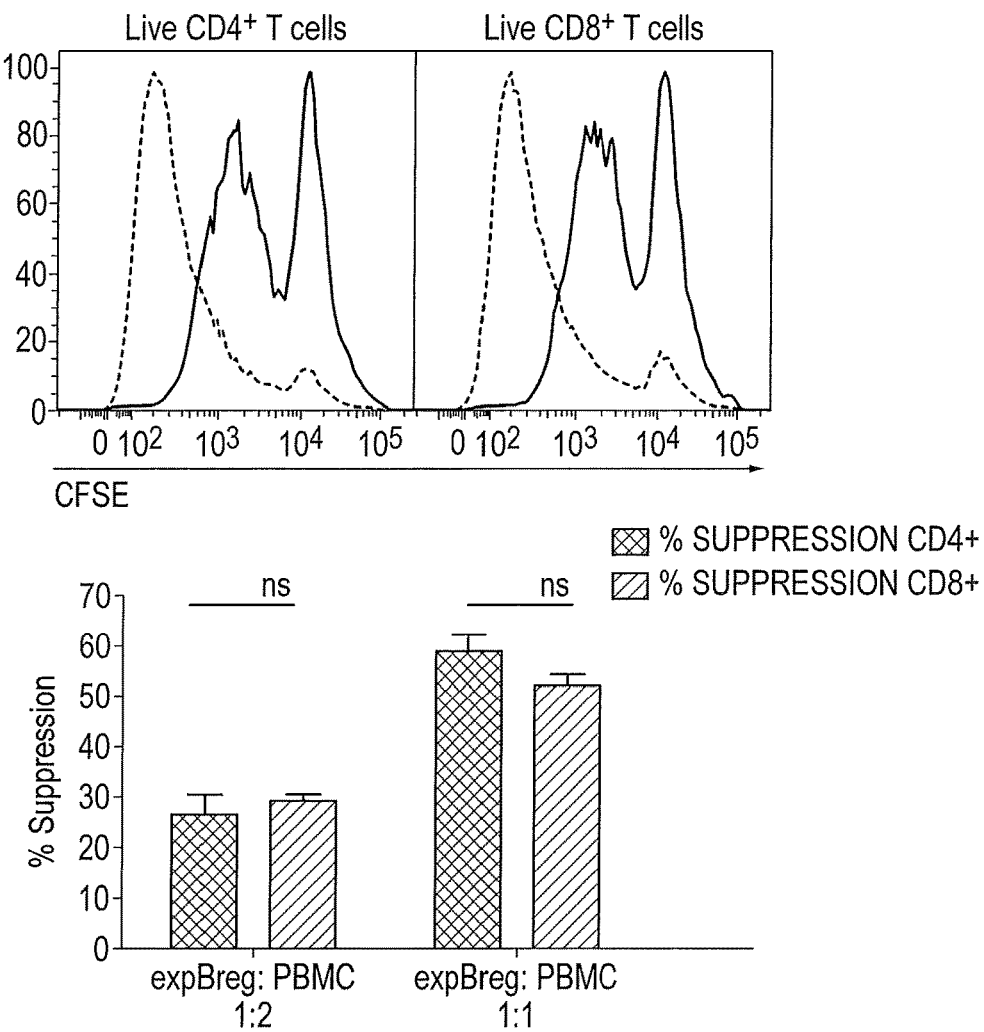

To investigate mechanisms downstream of IL-10R ligation within the expBreg cell, the STAT3 pathway was utilized as a read-out of the cellular response to IL-10 [3, 28]. This signaling pathway has been shown to be critical in the regulatory mechanisms of human $IL-10^+$ Breg, in part through CD40 stimulation, in the context of transplantation, GVHD, autoimmune disease and cancer [3, 29-31] (FIG. 4i). The response of expBreg to exogenous IL-10 was abolished when expBreg were pre-incubated with a blocking mAb to TIM-1 for the last 48 hours of expansion (FIG. 3g). Since STAT3 phosphorylation can also be induced by other cytokines, we investigated whether the inhibitory effect of TIM-1 blockade upon STAT3 phosphorylation could be observed in response to cytokines other than IL-10. Indeed, the phosphorylation of STAT3 in response to IL-21 stimulation was reduced when TIM-1 was blocked, demonstrating that TIM-1 could regulate STAT3 phosphorylation within expBreg in response to multiple cytokines (FIG. 3h). Thus downstream effects of TIM-1 blockade were not IL-10-specific. Importantly, these findings were mirrored by a significant reduction in suppressive potency of TIM-1-blocked-expBreg (FIG. 3i). Expression of IL-10R, CD40 or CD154 by TIM-1-blocked-expBreg remained unchanged (FIG. 4j). Furthermore, the addition of exogenous IL-21 to 5-day suppression assays, or pre-incubation of IL-21 with expBreg for the last 24 hours of expansion, increased the suppressive potency of expBreg (FIG. 10e). Therefore cognate CD40-CD154 interactions between the Breg and $CD4^+$ T cell stimulate the expBreg cell to up-regulate IL-10. Cytokines that can induce STAT3 phosphorylation, such as IL-10 and IL-21, promote suppressive potency of expBreg. TIM-1, expressed by expBreg, controls suppressive potency of the expBreg cell through modulation of STAT3 phosphorylation in response to these cytokines (FIG. 3j).

Figure 5A:
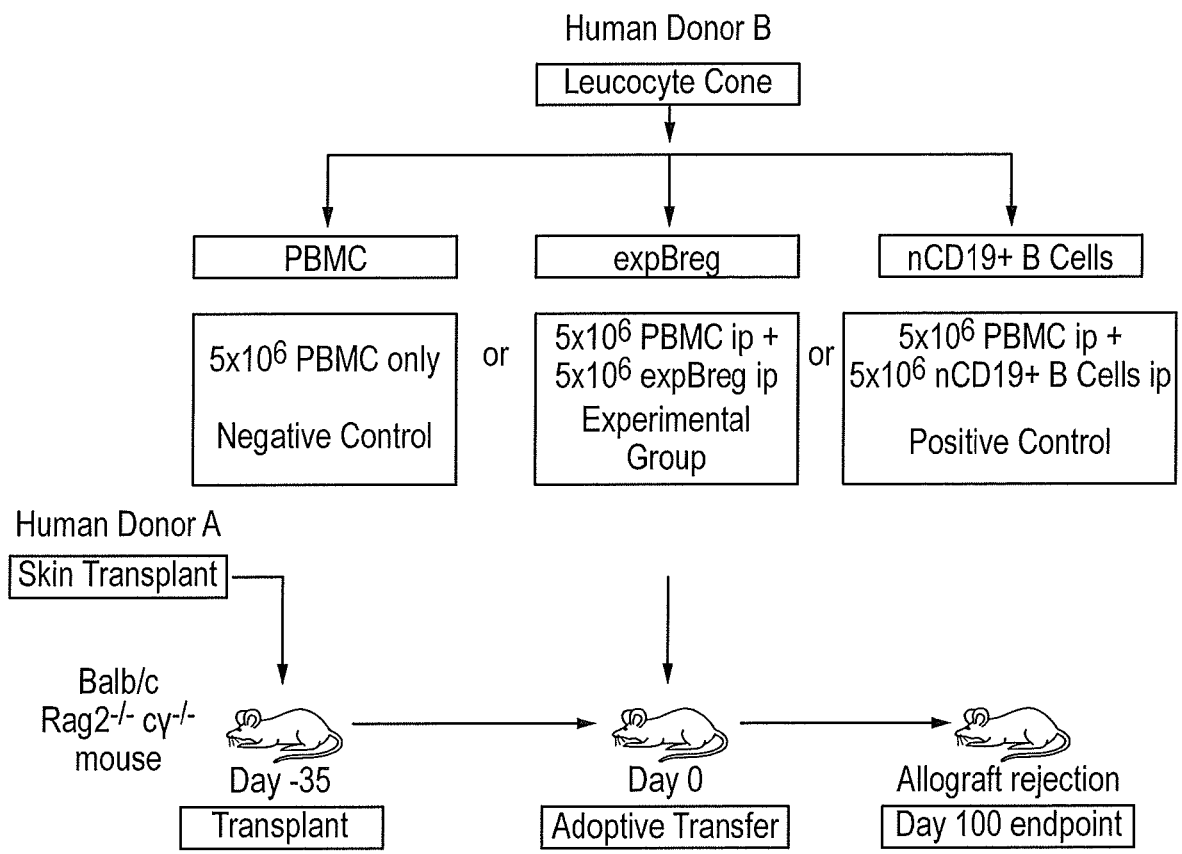
FIG. 5. CD73$^{31}$ CD25$^+$CD71$^+$TIM-1$^+$ expBreg significantly prolong human allograft survival in a humanised mouse model of skin transplantation. (a) expBreg prolong human allograft survival in a humanised mouse model of skin transplantation. Balb/c Rag2$^{-/-}$ c$\gamma^{-/-}$ mice were transplanted with human skin from donor A on day −35. On day 0, PBMC +/− expBreg or nCD19$^+$ B cells were transferred intraperitoneally (ip) into mice at a 1:1 ratio. Allograft, spleen and blood were harvested at rejection. ****p<0.0005, Log-rank (Mantel-Cox) test. Data are representative of 3 independent experiments using 3 different HLA-mismatched human donor pairs. In total, n=18 animals in each experimental group. (b) The number of huCD45$^+$CD4$^+$ T cells is decreased in human skin allografts of mice receiving PBMC+expBreg compared to controls. Prior to FACS analysis, human skin allograft was digested to obtain a cell suspension. Representative histograms of live huCD45$^+$CD4$^+$ and huCD45$^+$CD20$^+$ cells in human skin allograft are shown. Dashed line, mf−1 control; solid line, antibody staining. *p<0.05, p<0.005, paired t-test. (c) huCD45$^+$CD20$^+$ cells in blood, spleen and human skin allograft of mice that received PBMC+expBreg maintain TIM-1 expression. Representative histograms of live huCD45$^+$CD20$^+$TIM-1 B cells in human skin allograft of mice that received PBMC+expBreg. Dashed line, mf−1 control; solid line, TIM-1 staining. *p<0.0001, ****p<0.0005, paired t-test. (d) Percentage of live huCD45$^+$CD4$^+$CD25$^+$CD127$^{lo}$ putative Treg in skin allograft is increased in mice that received PBMC+expBreg compared to controls. Representative FACS plots of live huCD45$^+$CD4$^+$CD25$^+$CD127$^{lo}$ T cells in human skin allograft are shown. *p<0.05, paired t-test. Data represent 3 independent experiments using 3 different HLA-mismatched human donor pairs. In total, n=18 animals in each experimental group. (e) CD4$^+$CD25$^+$CD127$^{lo}$ Treg generated by expBreg in vitro have potent regulatory function. Autologous CD4$^+$ T cells were co-cultured with anti-CD3/CD28 beads only, or with nCD19$^+$ B cells or expBreg for 5 days. On day 5, CD4$^+$CD25$^+$CD127$^{lo}$ T cells were flow-sorted and co-cultured with autologous CFSE-stained PBMC+anti-CD3/CD28 beads for 5 days. Inhibition of proliferation of CFSE-stained CD4$^+$ T cells was measured. Error bars in each panel represent Mean +/− SD. Data represent 3 independent experiments using CD19$^+$ B cells from 3 different human donors.
Figure 5A:
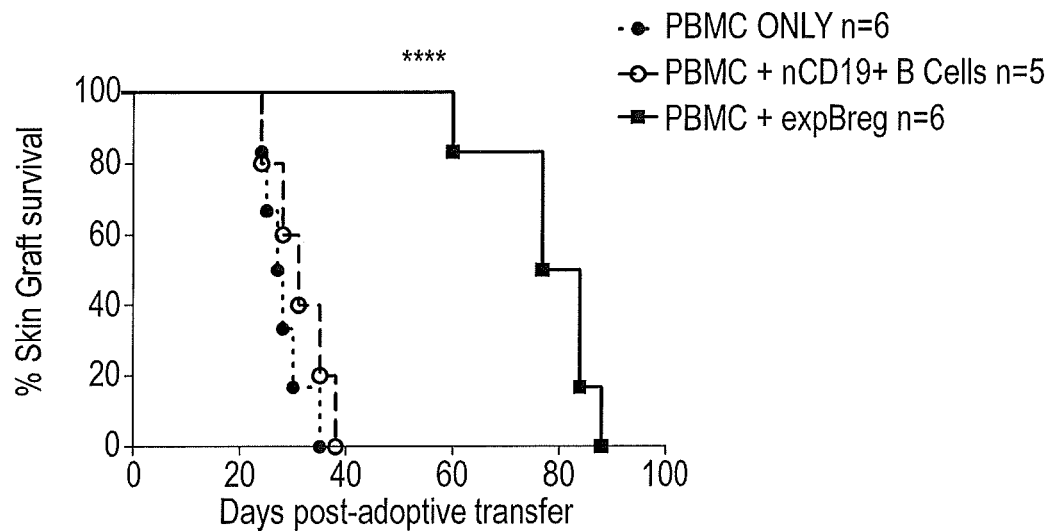
Figure 5B:
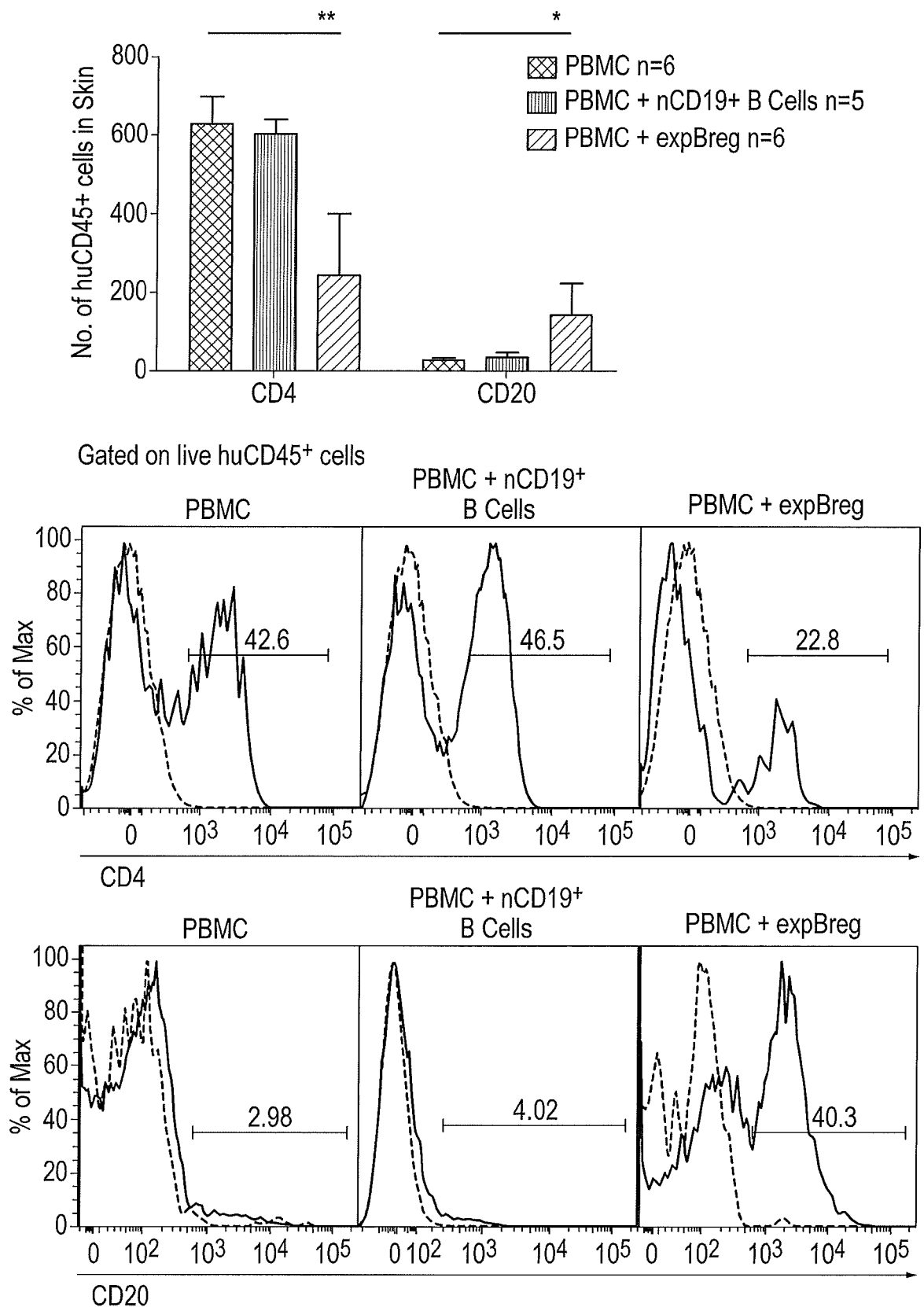
Figure 5C:
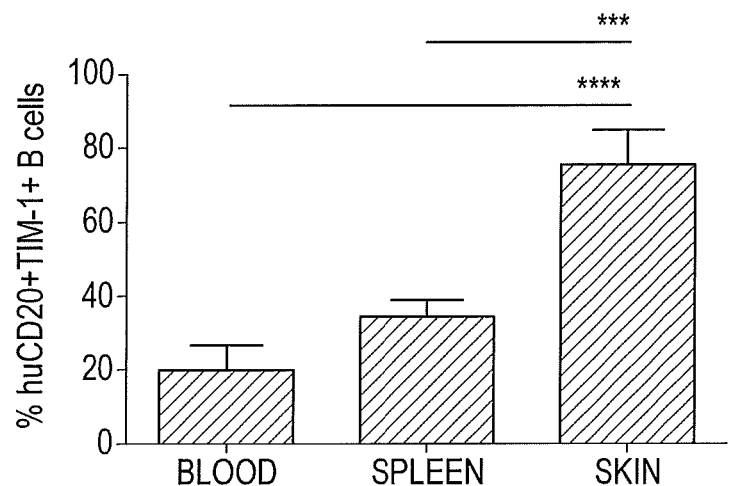
Figure 5C:
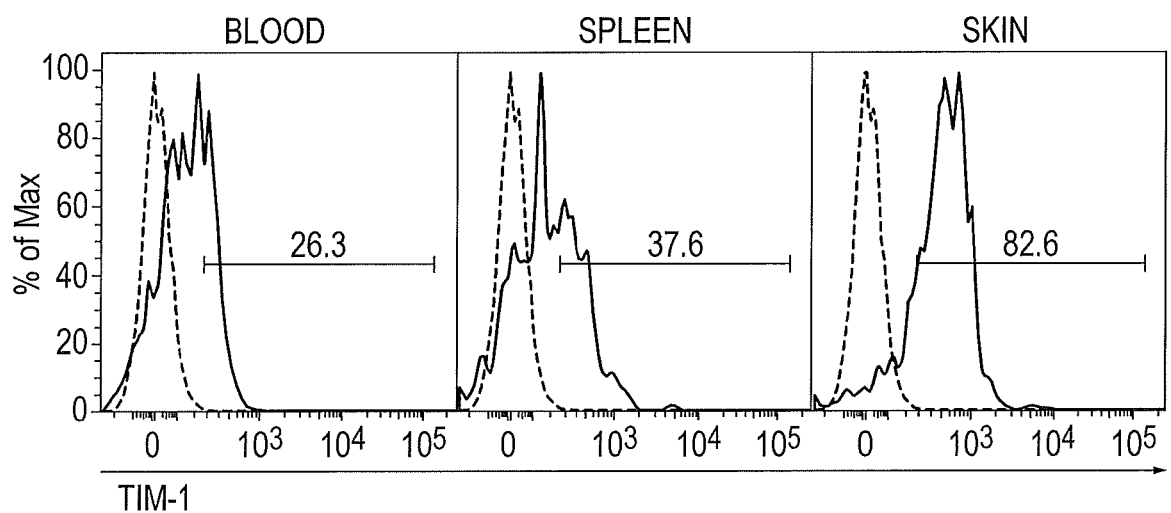
Figure 6B:
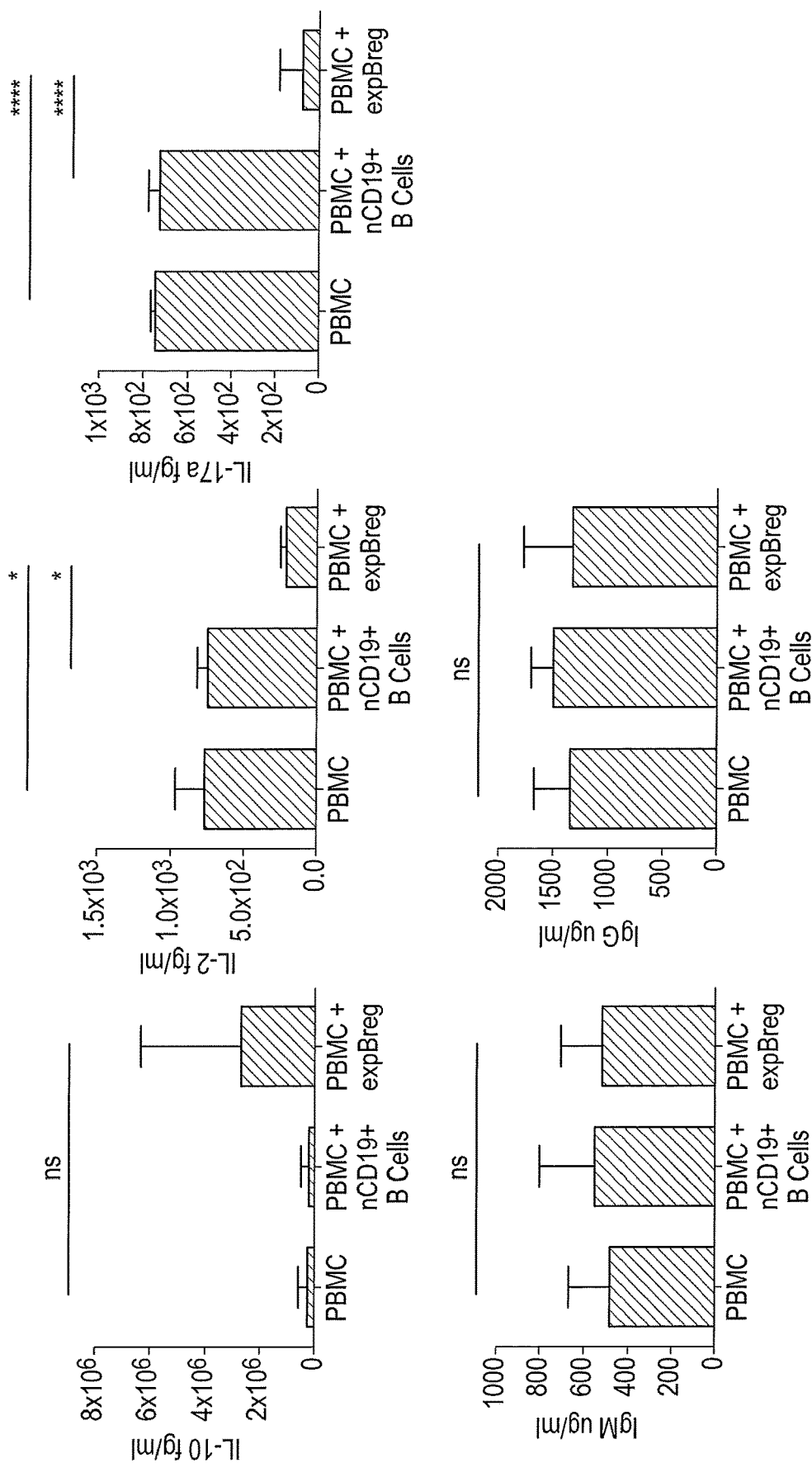
FIG. 6. (a) There is a significant decrease in number of huCD45$^+$CD4$^+$ T cells in spleen of mice which received PBMC+expBreg compared to control groups. *p<0.05, paired t-test. (b) Serum levels of human IL-2 and IL-17a are significantly reduced in mice which received PBMC+exp-Breg compared to control groups. *p<0.05, ****p<0.0005, paired t-test. (c) % Frequency of huCD45$^+$CD4$^+$FOXP3$^+$ cells is significantly increased in human skin allografts of mice that have received PBMC+expBreg compared to control groups. *p<0.05, paired t-test. (d) Absolute number of CD4$^+$CD25$^+$CD127$^{lo}$ T cells is significantly increased in human skin allograft of humanised mice which have received PBMC+expBreg when compared to control groups. *p<0.05, paired t-test. Data are representative of 3 independent experiments using 3 different HLA-mismatched human donor pairs. (e) expBreg can induce CD4$^+$CD25$^+$CD127$^{lo}$ T cells. There is a significant increase in % of putative Treg when expBreg and anti CD3/CD28 beads are co-cultured with CD4$^+$ T cells or CD4$^+$CD25$^-$ T cells in vitro for 5 days, when compared to controls. *p<0.05, p<0.005, **p<0.0005, paired t-test. (f) Experimental design to examine suppressive function of expBreg-induced CD4$^+$CD25$^+$CD127$^{lo}$ T Cells. Error bars in each panel represent Mean +/− SD. Data are representative of 3 independent experiments using CD19$^+$ B cells from 3 different human donors.

To determine whether this human Breg population maintained regulatory function in vivo, we utilized a humanized mouse model of human skin transplantation [32, 33]. Transplanted mice receiving PBMC and expBreg demonstrated significantly prolonged allograft survival when compared to those that had received PBMC alone or PBMC and $nCD19^+$ B cells (FIG. 5a). FACS analysis demonstrated a significant decrease in the number of $huCD45^+CD4^+$ T cells and a significant increase in the number of $huCD45^+CD20^+$ B cells in both the human skin allograft and spleen of mice which had been reconstituted by PBMC and expBreg, in comparison to control groups (FIG. 5b & FIG. 6a). Within the skin allografts of mice that had received PBMC and expBreg, $huCD45^+CD20^+$ B cells were predominantly $TIM-1^+$, with lower levels of TIM-1 expression in blood and spleen (FIG. 5c). Analysis of peripheral blood demonstrated no significant differences in serum levels of human immunoglobulin or hIL-10 across groups, although levels of pro-inflammatory cytokines hIL-2 and hIL-17a were significantly lower in mice that had received PBMC and expBreg (FIG. 6b).

Figure 5D:
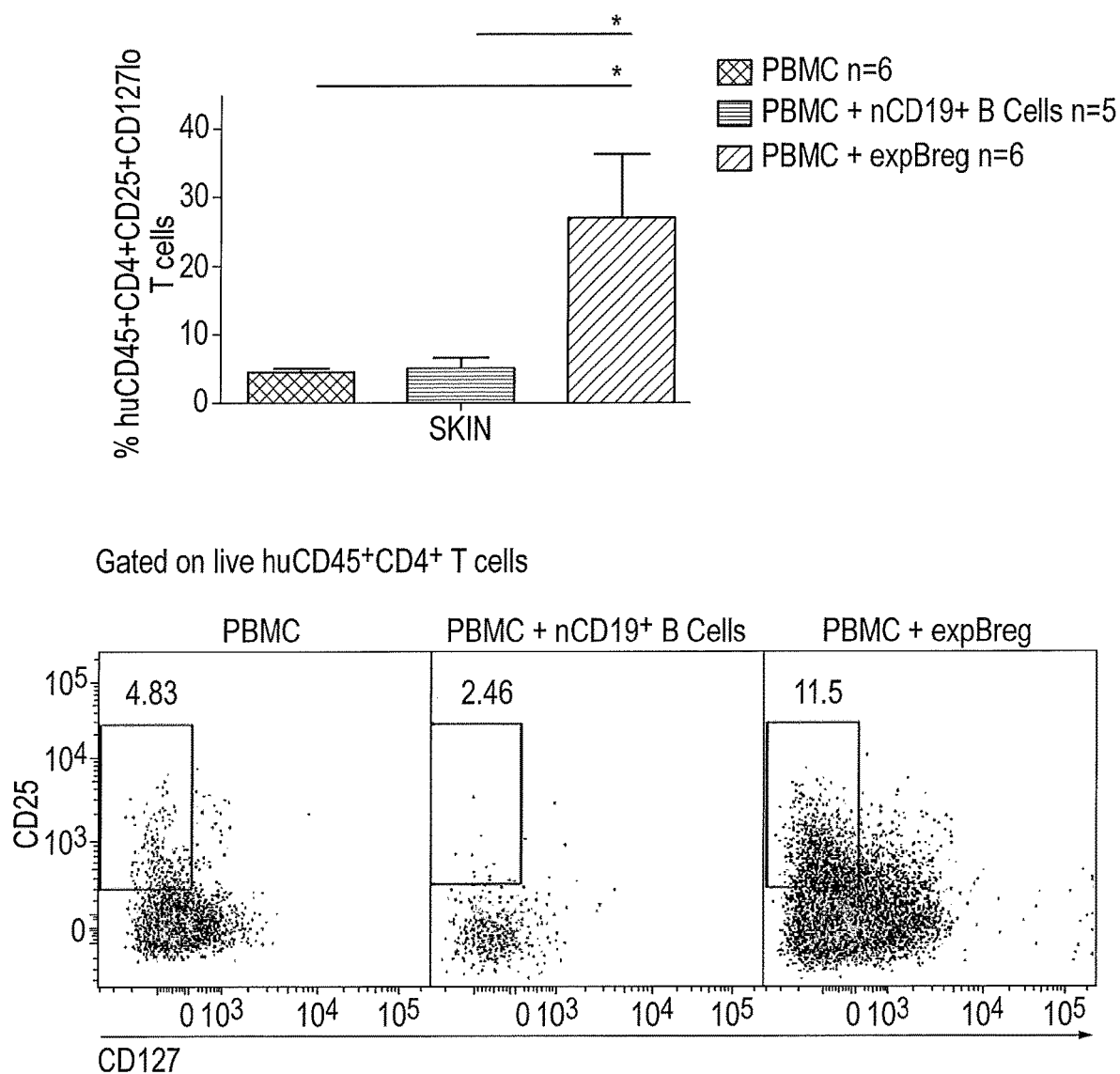
Figure 6C:
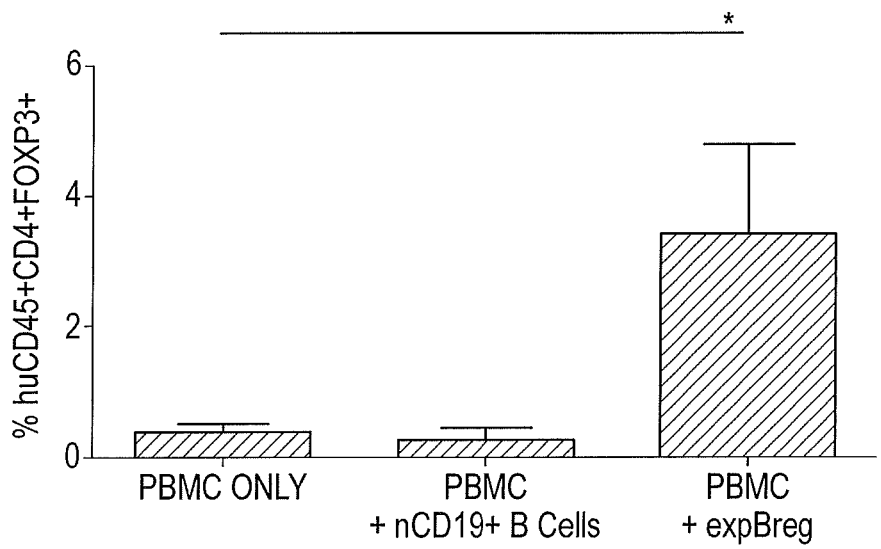
Figure 6D:
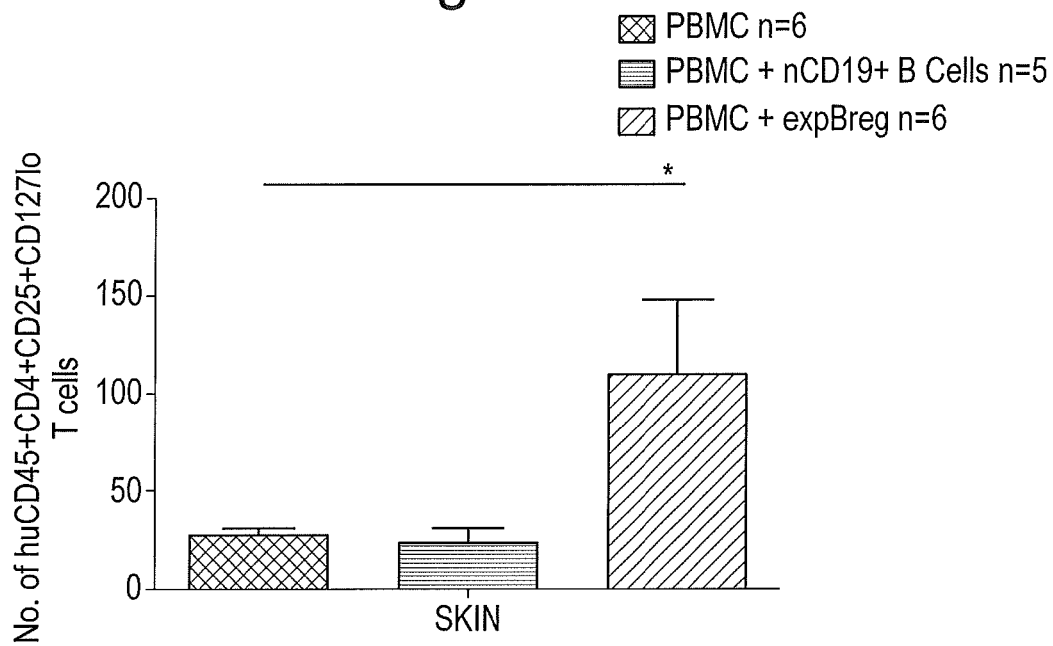

We found an almost three fold increase in percentage of putative huCD45$^+$CD4$^+$CD25$^+$CD127$^{lo}$ Treg and huCD45$^+$CD4$^+$FoxP3$^+$ T cells within the skin allografts of mice reconstituted with PBMC and expBreg, compared to control groups (FIG. 5d & FIG. 6c). Although an insufficient number of Treg could be extracted from human skin allografts to test function (FIG. 6d), in vitro experiments confirmed that expBreg were able to induce and expand potently suppressive human CD4$^+$CD25$^+$CD127$^{lo}$ Treg (FIG. 5e & FIG. 6e-f). Thus the balance of T effectors (Teff) to Treg shifts in the presence of expBreg, such that we saw an increase in the proportion of putative Treg in human allografts with prolonged survival.

Figure 7A:
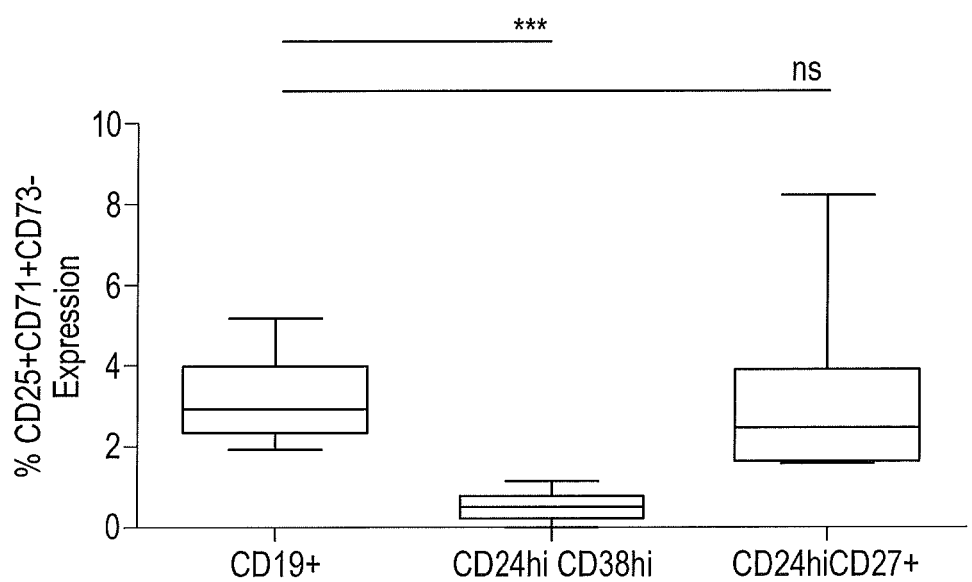
FIG. 7. CD73$^-$CD25$^+$ CD71$^+$ B cells in human peripheral blood are enriched for TIM-1 and CD154, and are more frequent in patients with Squamous Cell Carcinoma (SCC) of the skin. (a) CD73$^-$CD25$^+$CD71$^+$ B cells are present in whole CD19$^+$ B cells, CD24$^{hi}$CD38$^{hi}$ and CD24$^{hi}$CD27$^+$ B cell subsets known to be enriched for IL-10$^+$ Breg, in peripheral blood of healthy individuals (n=10). ***p<0.0001, Mann-Whitney test. (b) CD73$^-$CD25$^+$ CD71$^+$ B cells exhibit more frequent TIM-1 expression than CD19$^+$ B cells, CD24$^{hi}$ CD38$^{hi}$ B cells or CD24$^{hi}$CD27$^+$ B cells (n=10). Representative histograms of live CD19$^+$ B cells demonstrating TIM-1 expression are shown. Dashed line, mf−1 control; solid line, TIM-1 staining. *p<0.05, **p<0.0005, Mann-Whitney test. (c) CD73-CD25+ CD71+ B cells exhibit more frequent CD154 expression than CD19$^+$ B cells, CD24$^{hi}$CD38$^{hi}$ B cells or CD24$^{hi}$CD27$^+$ B cells (n=10). Representative histograms of live CD19$^+$ B cells demonstrating CD154 expression are shown. Dashed line, mf−1 control; solid line, CD154 staining. p<0.0005, Mann-Whitney test. (d) Frequency of CD73-CD25$^+$CD71$^+$ B cells is increased in patients with SCC compared to age-matched controls, unlike CD24$^{hi}$ CD38$^{hi}$ and CD24$^{hi}$CD27$^+$ B cell subsets. p<0.005, Mann-Whitney test. Median and interquartile range are displayed. n=8 SCC patients, n=8 control subjects.
Figure 8A:
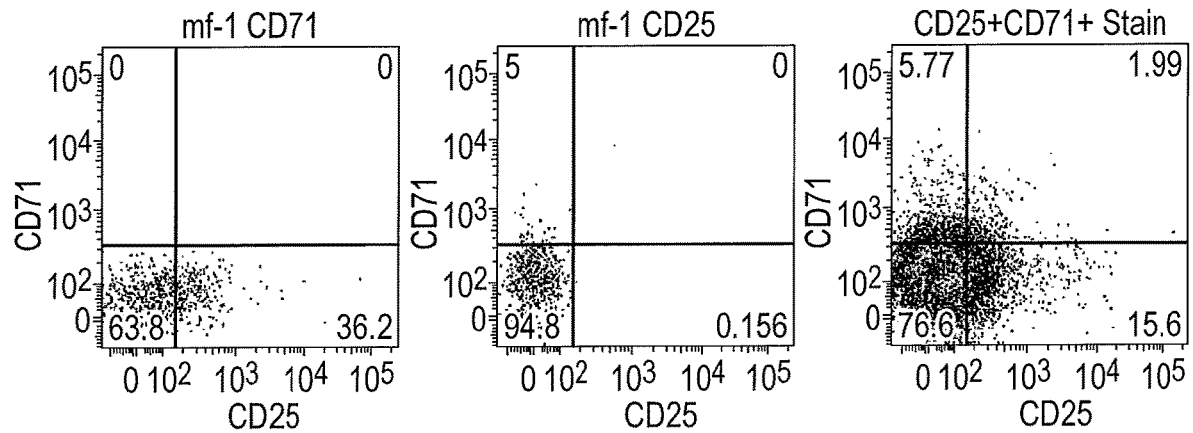
FIG. 8. (a) Representative FACS plots of live CD19$^+$CD73$^-$ B cells to demonstrate gating strategy for CD19$^+$CD73$^-$CD25$^+$CD71$^+$ B Cells from human peripheral blood.
Figure 9A:
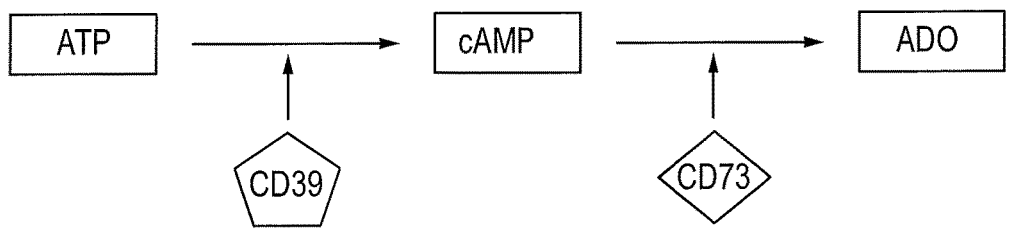
FIG. 9. (a) Simplified diagram outlining the pathway of ATP breakdown catalysed by endonucelotidases CD39 and CD73, also known as ecto-ATPases. (b) Graph demonstrates significant reduction in % CD4$^+$ T cell suppression mediated by EXPB10 cells when in the presence of an ecto-ATPase inhibitor (Inh) ARL 67156 at 0.1 mM/L. ***p<0.02, paired t-test.
Figure 9B:
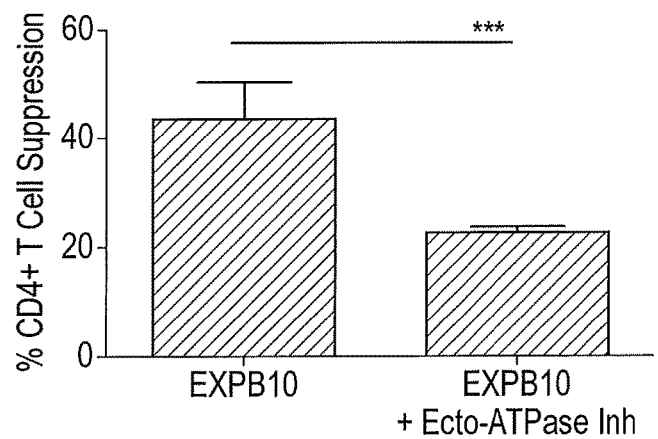

We have established that suppressive potency of CD73$^-$CD25$^+$CD71$^+$ expBreg is associated with the expression of TIM-1 and CD154. Phenotypic analysis of PBMC isolated from peripheral blood of 10 healthy individuals identified CD73$^-$CD25$^+$CD71$^+$ B cells within endogenous CD19$^+$ B cells, including the memory CD24$^{hi}$CD27$^+$ and transitional CD24$^{hi}$CD38$^{hi}$ B cell subsets known to be enriched for IL-10$^+$ Breg (FIG. 7a & FIG. 8a) [3, 4]. Endogenous CD73$^-$CD25$^+$CD71$^+$ B cells in human peripheral blood were significantly enriched for both CD154 and TIM-1 when compared to whole CD19$^+$ B cells, CD24$^{hi}$CD27$^+$ or CD24$^{hi}$CD38$^{hi}$ B cell populations (FIG. 7b-c). We also investigated the frequency of CD73$^-$CD25$^+$CD71$^+$ B cells in circulating blood of patients diagnosed with SCC, and found that it was significantly raised when compared to that of age-matched healthy controls, unlike the CD24$^{hi}$CD38$^{hi}$ and CD24$^{hi}$CD27$^+$ B cell subsets (FIG. 7d). Thus, it may be that the percentage increase seen in CD73$^-$CD25$^+$CD71$^+$ B cells in patients with a newly diagnosed cancer is indicative of an over-regulated immune system.

This study is the first to provide proof of concept data that human Breg are able to suppress a human alloimmune response in vivo. We describe a novel mechanism by which TIM-1 acts as a gatekeeper to control human Breg function through modulation of the intracellular response to autocrine IL-10. expBreg may also alter the balance of Teff and Treg to promote a more immunosuppressive environment. We have also identified an endogenous CD73$^-$CD25$^+$CD71$^+$ human Breg subset that is enriched in patients with SCC; the potency of such Breg appears to be associated with CD154 expression.

METHODS

Mice

Balb/c Rag2$^{31\,/-}$ cγ$^{31\,/-}$ mice were obtained from Charles River Laboratories and were housed under specific pathogen-free conditions in the Biomedical Services Unit of the John Radcliffe Hospital (Oxford, UK). Mice were housed in individually ventilated cages and handled with gloves. All experiments were performed using protocols approved by the Committee on Animal Care and Ethical Review at the University of Oxford and in accordance with the UK Animals (Scientific Procedures) Act 1986, under project license PPL 30/2550 and personal license PIL 30/9202. At the time of the first experimental procedure, mice were between the ages of 6 and 12 weeks. Adoptive transfer of human cells and graft survival experiments using human skin were performed as we have previously described [32, 38]. Tissue was harvested and analysed at the rejection endpoint, as previously described [32]. Mice injected with human PBMC were defined as fully reconstituted when human leucocyte chimerism levels of >1% in the spleen or 0.1% in the peripheral blood were established in the absence of GvHD.

Procurement of Human Skin

Split-thickness human skin at between 8-10/1000 inches thick were harvested with the use of an air-driven dermatome from the anterior abdominal wall of live donors undergoing plastic surgery procedures in the Department of Plastic and Reconstructive Surgery, John Radcliffe Hospital, Oxford. Exclusion criteria included donors who were taking immunosuppressive medication, donors with a primary inflammatory condition or donors with any current or past history of malignancy. Donor age ranged from 28 to 53 years (median 43 years). Skin was procured with the assistance of Mr Fadi Issa and other members of the Plastic Surgery team. Tissue was stored in RPMI-1640 on ice and was transplanted within 12 hours of procurement. Unused skin was destroyed. Tissue was obtained with full patient consent and ethical approval from the Oxfordshire Research Ethics Committee, study number 07/H0605/130. Blood samples were obtained with consent from skin donors for HLA-typing.

Skin Grafting

Skin grafting was performed with full sterile precautions. Mice were placed prone and a 1×1 cm piece of skin removed from the left dorsal thorax over the costal margin. A 1×1 cm piece of human skin was then fashioned and its edges sutured to the mouse recipient skin with a non-absorbable 8-0 Prolene suture (Ethicon, UK). Grafts were fenestrated and covered with povidone-iodine mesh and pressure dressings which were secured with circumferential tape. Bandages were left in place for 7-10 days and then removed under general anaesthetic. Skin grafts were monitored every 1-2 days until complete loss.

Human Subjects

Blood samples from patients with squamous cell carcinoma of the skin (SCC), as well as from healthy human subjects, were obtained with informed consent and ethical approval from the NHS Research Ethics Committee, study numbers 12/WS/0288 and 14/SC/0091. Blood samples were taken at time-points ranging from 0 to 755 days after the SCC diagnosis had been made (mean time-point of sample was 392 days). SCC patients were age-matched to healthy controls (SCC patients: mean age 81 yrs, age range 72-90 yrs. Healthy controls: mean age 77 yrs, age range 68-86 yrs). When recruiting healthy controls, participants who had been diagnosed with an autoimmune or inflammatory condition, or a malignancy, were excluded.

Human CD19$^+$ B Cell Isolation and Generation of expBreg

Human PBMC were isolated from leucocyte cones provided by the National Blood Service by Ficoll-Paque (GE Healthcare) gradient centrifugation. Human CD19$^+$ B cells were subsequently isolated from PBMC by negative selection using an EasySep® Human B Cell Enrichment Kit (Stem Cell Technologies), in accordance with manufacturer's guidelines. Purified human B cells were >96% CD19$^+$ as determined by flow cytometry. For all human CD19$^+$ B cell expansion experiments, CD19$^+$ B cells were cultured in 'complete media' (c.RPMI): RPMI-1640 (Sigma-Aldrich, St. Louis, USA) supplemented with 100 U/μg/ml penicillin/ streptomycin (Life Technologies, Carlsbad, USA), L-glutamine and 10% FCS (Gibco, UK). 0.06×10⁶ Human CD19⁺ B cells per well were seeded in 96-well U-bottom plates for 7 days. Irradiated CHO cells were co-cultured with human CD19⁺ B cells at ratios of 1:1, 1:5 or 1:10 CHO cells to CD19⁺ B cells in a total volume of 200 ul per well, with a cytokine combination of 50 U/ml of IL-2, 100 U/ml of IL-4 and 25 U/ml of IL-10 (all PeproTech, Rocky Hill, NJ).

Cultures were fed by replacing culture medium and cytokines every 2-3 days, while irradiated CHO-CD154 cells were renewed on day 3 of expansion. Ratios of CHO-CD154 cells to CD19 were kept constant throughout the culture period. Viable CD19⁺ B cells were harvested on day 7 of co-culture, stained with appropriate antibodies (CD19 and PerCP-conjugated 7-AAD viability dye, eBioscience) and sorted to obtain purities of >97% using a BD FacsARIA cell sorter (BD). Both Trypan-Blue exclusion and Calibrite counting beads (BD Biosciences) were used to determine absolute numbers of viable EXPB10 cells at time-points analysed.

Culture of Chinese Hamster Ovary (CHO) Cells

CD154⁺ and CD154⁻ CHO cell lines were kindly donated by Professor Claudia Mauri, University College London. CHO cells were cultured in DMEM containing 4500 μg/L glucose, 110 μg/L sodium pyruvate and L-glutamine (Sigma-Aldrich) with 100 U/ml penicillin and streptomycin (Life Technologies, Carlsbad, USA) and 5% foetal calf serum (FCS) (Gibco, UK). CD154 expression was routinely checked by flow cytometry analysis after staining with CD154-PE mAb (expression >98%). All CHO cell lines were cultured in Corning® T75 flasks and were passaged using standard operating procedure with Trypsin from porcine pancreas (2.5 g/L, Sigma, UK). Before being used in EXPB10 cell expansion cultures, CHO cells were γ-ray irradiated (65 Gy, 6500 rad) in 50 ml corning tubes for 30 minutes using a Caesium 137 irradiator.

In Vitro Suppression Assay

To assess the effect of expBreg or Treg cells on proliferation of CD4⁺ T cells, 0.05×10⁶ expBreg or Treg cells were co-cultured with autologous CD4⁺ T cells or PBMC for 5 days in 96-well U-bottom plates in a total volume of 200 ul per well. CD4⁺ T cells and PBMC (responder cells) were stained with either CF SE or VPD. Dye-stained responder cells were stimulated with anti-CD3/CD28 beads at a ratio of 1:10 beads to responder cells. Stimulated CD4⁺ T cells or PBMC cultured in the absence of expBreg, or instead with nCD19⁺ B cells, served as control conditions. On day 5 of culture, cells were harvested, stained for cell-surface markers and analysed by flow cytometry. % Inhibition of proliferation is an expression of Division Index (DI) of live CD4⁺CFSE⁺ T cells at day 5 relative to that of the stimulated CD4⁺ T cell control 0:1, such that % Inhibition of proliferation=(1−(DI of CD4⁺ T cells$_{experimental\ condition}$/DI of stimulated CD4⁺ T cells$_{control}$))×100.

To assess the effect of expBreg on intracellular cytokine production by CD4⁺ T cells, EXPB10 cells were co-cultured with CD4⁺ T cells and anti-CD3/CD28 beads for 72 hours. 2% PMA, 1% ionomycin and 1% brefeldin (PIB) were added to cultures for the last 6 hours of culture; cells were then harvested, surface-stained, permeabilised and stained intracellularly for Th1 cytokines interferon-γ (IFNγ) and tumour necrosis factor α (TNFα).

Mechanistic In Vitro Blockade

To determine mechanisms by which expBreg cells suppressed proliferation or cytokine production by autologous CD4⁺ T cells, different inhibitory reagents were added to in vitro suppression co-cultures on day 0 of the assay, unless otherwise stated. Inhibitory agents were added to both control and experimental conditions and expBreg-mediated suppression calculated relative to the control condition which had also been exposed to the inhibitory reagent. Inhibitory concentrations were determined by titration in excess of the ND50 provided by the manufacturer. When necessary, appropriate isotype mAbs were also used in control conditions. Reagents purchased from R&D Systems: anti-CD154 mAb [10 ug/ml], anti-CD40 mAb [10 ug/ml], anti-IL-10 mAb [10 ug/ml], anti-IL-10R mAb [10 ug/ml], anti-CD122 mAb [10 ug/ml], anti-CD25 mAb [10 ug/ml], IgG$_{1κ}$ mAb [10 ug/ml], IgG$_{2κ}$ mAb [10 ug/ml]. Reagent purchased from Biolegend: anti-TIM-1 mAb [10 ug/ml].

Flow Cytometry

Flow cytometric data were acquired using a FACSAria or BD Canto II (BD Biosciences, UK), and analysed using FlowJo software (Flowjo Enterprise, USA). Anti-human monoclonal antibodies purchased from BD Pharmingen: APC-Cy7-conjugated CD19 (SJ25C1), PE-Cy7-conjugated CD25 (M-A251), PE-conjugated CD24 (ML5), FITC-conjugated CD38 (HIT2), PE-conjugated CD127 (H1L-7R-M21), Alexa Fluor® 647-conjugated pSTAT3 (pY705). Anti-human monoclonal antibodies purchased from eBioscience: PE-Cy7-conjugated CD20 (2γCR (TUGh4), eFluor® 450-conjugated CD27 (O323), eFluor® 450-conjugated CD138 (HB7), APC-conjugated CD1d (51.1), FITC-conjugated CD5 (L17F12), eFluor® 450-conjugated CD21 (HB5), APC-conjugated CD71 (OKT9), eFluor® 450-conjugated CD73 (AD2), PE-conjugated LAP (FNLAP), eFluor® 660-conjugated IL-10 (JES3-9D7), FITC-conjugated TNFα (MAb11), PE-conjugated IFNγ (4S.B3), PE-conjugated CD154 (24-31), APC-conjugated CD40 (5C3). Anti-human monoclonal antibodies purchased from Biolegend: PE-conjugated TIM-1 (1D12), APC-conjugated IL-10R (3F9), APC-conjugated CD122 (TU27). Anti-human monoclonal antibody purchased from Beckman Coulter: PE-Texas Red-conjugated CD10 (ALB-1). Anti-human monoclonal antibody purchased from Invitrogen: APC-conjugated CD45 (HI30).

Cell-Surface Marker Staining

Cells were first incubated with human sera for 15 minutes at 4° C. to reduce non-specific antibody binding. Cells were then incubated with the appropriate fluorochrome-coupled mAbs for 45 minutes at 4° C. in the dark. Cells were then washed with PBS and spun for 5 minutes at 1500 rpm at 4° C. before flow cytometry analysis. Mean fluorescence minus 1 (mf−1) controls were used as standard controls to permit accurate gating of positive and negative populations.

Intracellular Staining

After appropriate cell-surface staining, cells were permeabilised using a BD Cytofix/Cytoperm™ Kit (BD Biosciences, UK) in accordance with manufacturer's guidelines. Cells were then incubated with either the fluorochrome-coupled mAb under interrogation or the appropriate isotype control for 1 hour at 4° C. in the dark. Cells were washed with PBS and spun for 5 minutes at 1500 rpm at 4° C. before flow cytometry analysis. In order to measure expression of IL-10, cells were first incubated for 6 hours with PMA, ionomycin and monensin (PIM) in c.RPMI before staining.

pSTAT3 Staining expBreg cells were harvested from expansion co-cultures, initially rested in c.RPMI for 90 minutes and then washed to allow any existing pSTAT3 to degrade. $0.1 \times 10^6$ expBreg cells were subsequently incubated in 100 µl c.RPMI for 10 minutes at 37° C., with exogenous human IL-10 at 25 U/ml (or c.RPMI as a control) in 96-well, v-bottom plates. 100 µl/well of Cytofix™ fixation Buffer (BD Biosciences, UK) was added to cell culture for an additional 10 minute incubation period at 37° C. Cells were subsequently spun for 5 minutes at 1500 rpm at 4° C. and supernatants decanted. 100 µl/well of Phosflow™ Perm Buffer (BD Biosciences, UK) was added to cell culture and cells were incubated for 30 minutes on ice. Cells were then washed twice with PBS at 1500 rpm for 5 minutes at 4° C. before staining with Alexa Fluor® 647-conjugated pSTAT3 antibody (BD Pharmingen) for 1 hour at 4° C. Cells were washed with PBS at 1500 rpm for 5 minutes at 4° C. before immediate FACS analysis. mf–1 controls were used to assist accurate gating. $CD4^+$ T cells, $nCD19^+$ B cells and unstained expBreg cells were included as relevant controls.

ELISA

Levels of human cytokines IL-35 and IL-10 in in vitro culture supernatants were measured using a Human IL-35 Heterodimer ELISA Kit (Biolegend) and a Human IL-10 ELISA kit (BD Biosciences) respectively, in accordance with manufacturers' guidelines.

Cytokine Bead Array

Levels of human cytokines IL-2, IL-10, and IL-17a as well as human immunoglobulin IgG (total) and IgM in humanised Balb/c $Rag2^{-/-} c\gamma^{-/-}$ mouse sera were measured using a Human Cytokine Bead Array Enhanced Sensitivity Flex Set system (BD Biosciences), in accordance with manufacturer's guidelines. All data was processed using FCAP v1.0 analysis software (BD Biosciences).

Tissue Typing 5 ml of whole blood was obtained from skin donors and leucocyte cones. These samples were analysed by the Oxford Transplant Centre Histocompatibility and Genetics Laboratory. Full tissue-typing was performed for HLA-A, -B, -Cw, -DR and -DQ.

Statistical Analysis

Log-rank tests, non-parametric Mann-Whitney U tests and parametric Student t-tests were applied as appropriate and as detailed in figure legends. Statistical analysis was performed using Graphpad Prism v6.0 software. p values less than 0.05 were considered significant.

REFERENCES

1. Newell, K. A., et al., *Identification of a B cell signature associated with renal transplant tolerance in humans*. J Clin Invest, 2010. 120(6): p. 1836-47.
2. Sagoo, P., et al., *Development of a cross-platform biomarker signature to detect renal transplant tolerance in humans*. J Clin Invest, 2010. 120(6): p. 1848-61.
3. Blair, P. A., et al., *CD19(+)CD24(hi)CD38(hi) B cells exhibit regulatory capacity in healthy individuals but are functionally impaired in systemic Lupus Erythematosus patients*. Immunity, 2010. 32(1): p. 129-40.
4. Iwata, Y., et al., *Characterization of a rare IL-10-competent B-cell subset in humans that parallels mouse regulatory B10 cells*. Blood, 2011. 117(2): p. 530-41.
5. Rebollo-Mesa, I., et al., *Biomarkers of Tolerance in Kidney Transplantation: Are We Predicting Tolerance or Response to Immunosuppressive Treatment?* Am J Transplant, 2016.
6. Carter, N. A., et al., *Mice lacking endogenous IL-10-producing regulatory B cells develop exacerbated disease and present with an increased frequency of Th1/Th17 but a decrease in regulatory T cells*. J Immunol, 2011. 186(10): p. 5569-79.
7. Watanabe, R., et al., *Regulatory B cells (B10 cells) have a suppressive role in murine lupus: CD19 and B10 cell deficiency exacerbates systemic autoimmunity*. J Immunol, 2010. 184(9): p. 4801-9.
8. DiLillo, D. J., et al., *B lymphocytes differentially influence acute and chronic allograft rejection in mice*. J Immunol, 2011. 186(4): p. 2643-54.
9. Lee, K. M., et al., *TGF-beta-producing regulatory B cells induce regulatory T cells and promote transplantation tolerance*. Eur J Immunol, 2014. 44(6): p. 1728-36.
10. Rosser, E. C., et al., *Regulatory B cells are induced by gut microbiota-driven interleukin-1beta and interleukin-6 production*. Nat Med, 2014. 20(11): p. 1334-9.
11. Tang, A., et al., *B cells promote tumor progression in a mouse model of HPV-mediated cervical cancer*. Int J Cancer, 2016.
12. Tadmor, T., et al., *The absence of B lymphocytes reduces the number and function of T-regulatory cells and enhances the anti-tumor response in a murine tumor model*. Cancer Immunol Immunother, 2011. 60(5): p. 609-19.
13. Liu, J., et al., *IL-10-producing B cells are induced early in HIV-1 infection and suppress HIV-1-specific T cell responses*. PLoS One, 2014. 9(2): p. e89236.
14. Mohanram, V., et al., *B Cell Responses Associated with Vaccine-Induced Delayed SIVmac251 Acquisition in Female Rhesus Macaques*. J Immunol, 2016. 197(6): p. 2316-24.
15. Yoshizaki, A., et al., *Regulatory B cells control T-cell autoimmunity through IL-21-dependent cognate interactions*. Nature, 2012. 491(7423): p. 264-8.
16. Mauri, C., et al., *Prevention of arthritis by interleukin 10-producing B cells*. J Exp Med, 2003. 197(4): p. 489-501.
17. Mauri, C., L. T. Mars, and M. Londei, *Therapeutic activity of agonistic monoclonal antibodies against CD40 in a chronic autoimmune inflammatory process*. Nat Med, 2000. 6(6): p. 673-9.
18. Rosser, E. C. and C. Mauri, *Regulatory B cells: origin, phenotype, and function*. Immunity, 2015, 42(4): p, 607-12.
19. van de Veen, W., et al., *IgG4 production is confined to human IL-10-producing regulatory B cells that suppress antigen-specific immune responses*. J Allergy Clin Immunol, 2013. 131(4): p. 1204-12.
20. Lemoine, S., et al., *Human T cells induce their own regulation through activation of B cells*. J Autoimmun, 2011. 36(3-4): p. 228-38.

21. Ding, Q., et al., *Regulatory B cells are identified by expression of TIM-1 and can be induced through TIM-1 ligation to promote tolerance in mice.* J Clin Invest, 2011. 121(9): p. 3645-56.
22. Yeung, M. Y., et al., *TIM-1 signaling is required for maintenance and induction of regulatory B cells.* Am J Transplant, 2015. 15(4): p. 942-53.
23. Xiao, S., et al., *Defect in regulatory B-cell function and development of systemic autoimmunity in T-cell Ig mucin 1 (Tim-1) mucin domain-mutant mice.* Proc Natl Acad Sci USA, 2012. 109(30): p. 12105-10.
24. Xiao, S., et al., *Tim-1 is essential for induction and maintenance of IL-10 in regulatory B cells and their regulation of tissue inflammation.* J Immunol, 2015. 194 (4): p. 1602-8.
25. Blair, P. A., et al., *Selective targeting of B cells with agonistic anti-CD40 is an efficacious strategy for the generation of induced regulatory T2-like B cells and for the suppression of lupus in MRL/lpr mice.* J Immunol, 2009. 182(6): p. 3492-502.
26. Wang, R. X., et al., *Interleukin-35 induces regulatory B cells that suppress autoimmune disease.* Nat Med, 2014. 20(6): p. 633-41.
27. Shen, P., et al., *IL-35-producing B cells are critical regulators of immunity during autoimmune and infectious diseases.* Nature, 2014. 507(7492): p. 366-70.
28. Saraiva, M. and A. O'Garra, *The regulation of IL-10 production by immune cells.* Nat Rev Immunol, 2010. 10(3): p. 170-81.
29. de Masson, A., et al., *CD24(hi)CD27(+) and plasmablast-like regulatory B cells in human chronic graft-versus-host disease.* Blood, 2015. 125(11): p. 1830-9.
30. Silva, H. M., et al., *Preserving the B-cell compartment favors operational tolerance in human renal transplantation.* Mol Med, 2012. 18: p. 733-43.
31. Yang, C., et al., *B cells promote tumor progression via STAT3 regulated-angiogenesis.* PLoS One, 2013. 8(5): p. e64159.
32. Issa, F., et al., *Ex vivo-expanded human regulatory T cells prevent the rejection of skin allografts in a humanized mouse model.* Transplantation, 2010. 90(12): p. 1321-7.
33. Nadig, S. N., et al., *In vivo prevention of transplant arteriosclerosis by ex vivo-expanded human regulatory T cells.* Nat Med, 2010. 16(7): p. 809-13.
34. Carter, N. A., E. C. Rosser, and C. Mauri, *Interleukin-10 produced by B cells is crucial for the suppression of Th17/Th1 responses, induction of T regulatory type 1 cells and reduction of collagen-induced arthritis.* Arthritis Res Ther, 2012. 14(1): p. R32.
35. Affara, N. I., et al., *B cells regulate macrophage phenotype and response to chemotherapy in squamous carcinomas.* Cancer Cell, 2014. 25(6): p. 809-21.
36. Andreu, P., et al., *FcRgamma activation regulates inflammation-associated squamous carcinogenesis.* Cancer Cell, 2010. 17(2): p. 121-34.
37. de Visser, K. E., L. V. Korets, and L. M. Coussens, *De novo carcinogenesis promoted by chronic inflammation is B lymphocyte dependent.* Cancer Cell, 2005. 7(5): p. 411-23.
38. Issa, F., et al., *Homing of regulatory T cells to human skin is important for the prevention of alloimmune-mediated pathology in an in vivo cellular therapy model.* PLoS One, 2012. 7(12): p. e53331.

The invention claimed is:

1. An isolated population of cells, wherein the population comprises human Breg cells, having the phenotype $CD19^+CD73^-CD71^+CD25^+TIM-1^+$, and wherein the human Breg cells additionally have the phenotype $CD154^+$.

2. The isolated cell population of claim 1, wherein at least 50% of the human Breg cells in the cell population express CD19 and at least 50% of the human Breg cells in the cell population do not express CD73 and at least 50% of the human Breg cells in the cell population express CD71 and at least 50% of the human Breg cells in the cell population express CD25 and at least 50% of the human Breg cells in the cell population express TIM-1.

3. The isolated cell population of claim 1, wherein the human Breg cells additionally have a phenotype selected from the group consisting of $IL-10R^+$ and $CD39^+$.

4. The isolated cell population of claim 1, wherein the human Breg cells additionally have a phenotype selected from the group consisting of $CD5^-$, $CD1d^-$, $CD24^-$, $CD27^-$, $CD21^-$ and $CD38^-$.

5. The isolated cell population of claim 1, wherein less than 30% of the human Breg cells in the cell population express IL-10.

6. The isolated cell population of claim 1, wherein at least 50% of the cells in the population are human Breg cells having the phenotype $CD19^+CD73^-CD71^+CD25^+TIM-1^+$ or $CD19^+CD73^-CD71^+CD25TIM-1^+CD154^+$.

7. A pharmaceutical composition comprising the isolated population of cells according to claim 1 and a pharmaceutically acceptable carrier.

8. The pharmaceutical composition of claim 7 wherein the isolated population of cells comprises at least 50% of the composition.

9. A method for producing a human Breg cell population comprising:
   isolating human $CD19^+$ B cells;
   culturing said $CD19^+$ B cells in the presence of CD154, or peptide fragments thereof, and/or cells expressing CD154, and at least one cytokine or growth factor for at least 3 days;
   harvesting the Breg cells so produced.

10. The method according to claim 9, wherein culturing said $CD19^+$ B cells in the presence of a CD40 agonist comprises culturing the $CD19^+$ B cells in the presence of cells expressing CD154 and wherein the cells expressing CD154 and the $CD19^+$ B cells are cultured at a ratio of 1:1.

11. The method according to claim 9, wherein the at least one cytokine is selected from the group consisting of IL-2, IL-4 and IL-10, and combinations thereof.

12. The method according to claim 9, wherein the at least one cytokine comprises IL-21; or (ii) wherein IL-21 is not added during culturing of the human $CD19^+$ B cells.

13. The method according to claim 9, wherein the human $CD19^+$ B cells are cultured for between 3-60 days, optionally 3-7 days.

14. The method of claim 9, wherein the human Breg cells are expanded by at least 200 fold.

15. The method according to claim 9, wherein the human $CD19^+$ B cells are isolated from a patient sample.

16. The method according to claim 9, wherein the human $CD19^+$ B cells are isolated from a patient sample, and wherein the patient sample is a blood sample.

17. The method according to claim 9, wherein the Breg cells produced have the phenotype $CD19^+CD73^-CD71^+CD25^+TIM-1^+$ or $CD19^+CD73^-CD71^+CD25^+TIM-1^+CD154^+$.

18. The method according to claim 9, wherein the harvested cells comprise at least 80% human Breg cells.

19. An expanded human Breg cell population obtained by isolating human CD19$^+$ B cells,
culturing said CD19$^+$ B cells in the presence of cells expressing CD154 at a ratio of 1:1, and at least one cytokine or growth factor for at least 3 days, and
harvesting the Breg cells so produced.

20. The method according to claim 9 further comprising genetically modifying said human CD19$^+$ B cells prior to expansion, to express a target antigen, wherein the target antigen is associated with an immune-mediated disorder.

* * * * *